United States Patent
Niitsu et al.

(10) Patent No.: US 10,000,447 B2
(45) Date of Patent: Jun. 19, 2018

(54) COMPOUNDS FOR TARGETING DRUG DELIVERY AND ENHANCING SIRNA ACTIVITY

(71) Applicant: Nitto Denko Corporation, Osaka (JP)

(72) Inventors: Yoshiro Niitsu, Hokkaido (JP); Joseph E. Payne, Oceanside, CA (US); John A. Gaudette, Poway, CA (US); Zheng Hou, San Diego, CA (US); Victor Knopov, Oceanside, CA (US); Richard P. Witte, San Diego, CA (US); Mohammad Ahmadian, Carlsbad, CA (US); Loren A. Perelman, San Diego, CA (US); Yasunobu Tanaka, Osaka (JP); Violetta Akopian, Oceanside, CA (US)

(73) Assignee: Nitto Denko Corporation, Osaka (JP)

(*) Notice: Subject to any disclaimer, the term of this patent is extended or adjusted under 35 U.S.C. 154(b) by 0 days. days.

(21) Appl. No.: 15/177,269

(22) Filed: Jun. 8, 2016

(65) Prior Publication Data
US 2017/0000893 A1    Jan. 5, 2017

Related U.S. Application Data

(62) Division of application No. 13/492,424, filed on Jun. 8, 2012, now Pat. No. 9,393,315.

(60) Provisional application No. 61/494,840, filed on Jun. 8, 2011.

(51) Int. Cl.
| | |
|---|---|
| C07C 237/22 | (2006.01) |
| C07F 9/10 | (2006.01) |
| A61K 9/127 | (2006.01) |
| A61K 31/713 | (2006.01) |
| C12N 15/113 | (2010.01) |
| C07C 233/21 | (2006.01) |
| C07C 235/08 | (2006.01) |
| C07C 235/48 | (2006.01) |
| A61K 47/55 | (2017.01) |
| A61K 31/07 | (2006.01) |

(52) U.S. Cl.
CPC ............ *C07C 237/22* (2013.01); *A61K 9/127* (2013.01); *A61K 9/1271* (2013.01); *A61K 31/713* (2013.01); *A61K 47/551* (2017.08); *C07C 233/21* (2013.01); *C07C 235/08* (2013.01); *C07C 235/48* (2013.01); *C07F 9/10* (2013.01); *C12N 15/113* (2013.01); *A61K 31/07* (2013.01); *C07C 2601/16* (2017.05); *C12N 2310/14* (2013.01); *C12N 2320/32* (2013.01); *Y10S 977/773* (2013.01); *Y10S 977/906* (2013.01); *Y10S 977/907* (2013.01)

(58) Field of Classification Search
None
See application file for complete search history.

(56) References Cited

U.S. PATENT DOCUMENTS

| | | | |
|---|---|---|---|
| 4,830,858 A | 5/1989 | Payne et al. | |
| 5,958,894 A | 9/1999 | Heath et al. | |
| 6,270,806 B1* | 8/2001 | Liversidge | A61K 9/145 424/497 |
| 6,372,714 B1 | 4/2002 | Tanaka et al. | |
| 6,468,551 B1 | 10/2002 | Diec et al. | |
| 6,635,683 B1 | 10/2003 | Taira et al. | |
| 7,799,565 B2 | 9/2010 | MacLachlan et al. | |
| 7,803,397 B2 | 9/2010 | Heyes et al. | |
| 7,807,815 B2 | 10/2010 | MacLachlan et al. | |
| 7,811,602 B2 | 10/2010 | Cullis et al. | |
| 7,901,708 B2 | 3/2011 | MacLachlan et al. | |
| 8,003,621 B2* | 8/2011 | Niitsu | A61K 31/337 424/497 |
| 8,173,170 B2 | 5/2012 | Niitsu et al. | |
| 8,664,376 B2* | 3/2014 | Niitsu | C12N 15/111 536/24.5 |
| 8,741,867 B2* | 6/2014 | Niitsu | C12N 15/111 514/44 A |
| 9,393,315 B2 | 7/2016 | Niitsu et al. | |
| 2001/0038851 A1* | 11/2001 | Allen | A61K 9/127 424/450 |
| 2003/0077829 A1 | 4/2003 | MacLachlan | |
| 2004/0142025 A1 | 7/2004 | MacLachlan et al. | |
| 2004/0247624 A1* | 12/2004 | Unger | A61K 9/19 424/400 |
| 2006/0121105 A1* | 6/2006 | Barenholz | A61K 9/1271 424/450 |

(Continued)

FOREIGN PATENT DOCUMENTS

| | | |
|---|---|---|
| DE | 19641672 | 4/1998 |
| EP | 1842557 | 10/2007 |

(Continued)

OTHER PUBLICATIONS

Abu Lila et al., "Oxaliplatin encapsulated in PEG-coated cationic liposomes induces significant tumor growth suppression via a dual-targeting approach in a murine solid tumor model," Journal of Controlled Release, Jul. 1, 2009, 137(1), 8-14.

(Continued)

*Primary Examiner* — Isaac Shomer
(74) *Attorney, Agent, or Firm* — Baker & Hostetler LLP

(57) ABSTRACT

Here described are compounds consisting of the structure (targeting molecule)$_m$-linker-(targeting molecule)$_n$, wherein the targeting molecule is a retinoid or a fat soluble vitamin having a specific receptor on the target cell; wherein m and n are independently 0, 1, 2 or 3; and wherein the linker comprises a polyethylene glycol (PEG) or PEG-like molecule, as well as compositions and pharmaceutical formulations including these compounds which are useful for the targeting and delivery of therapeutic agents; and methods of using these compositions and pharmaceutical formulations.

16 Claims, 9 Drawing Sheets

(56) References Cited

U.S. PATENT DOCUMENTS

| | | | |
|---|---|---|---|
| 2006/0134189 A1 | 6/2006 | MacLachlan et al. | |
| 2006/0240093 A1 | 10/2006 | MacLachlan et al. | |
| 2007/0042031 A1 | 2/2007 | MacLachlan et al. | |
| 2007/0128118 A1 | 6/2007 | Yu et al. | |
| 2008/0193512 A1* | 8/2008 | Niitsu ................. | A61K 9/0019 424/450 |
| 2008/0253969 A1 | 10/2008 | Yu et al. | |
| 2008/0274116 A1 | 11/2008 | Keil et al. | |
| 2008/0279778 A1 | 11/2008 | Van et al. | |
| 2008/0279782 A1 | 11/2008 | Van et al. | |
| 2009/0105179 A1 | 4/2009 | Yu et al. | |
| 2009/0163705 A1 | 6/2009 | Manoharan et al. | |
| 2009/0226393 A1 | 9/2009 | Wang et al. | |
| 2009/0247608 A1 | 10/2009 | Manoharan et al. | |
| 2010/0028416 A1 | 2/2010 | Yu et al. | |
| 2010/0130588 A1 | 5/2010 | Yaworski et al. | |
| 2010/0233275 A1 | 9/2010 | Saulnier et al. | |
| 2010/0266676 A1 | 10/2010 | Saulnier et al. | |
| 2010/0297247 A1 | 11/2010 | Anton et al. | |
| 2010/0330166 A1 | 12/2010 | Ishida et al. | |
| 2010/0331234 A1 | 12/2010 | Mahon et al. | |
| 2011/0040113 A1 | 2/2011 | Wu et al. | |
| 2011/0104255 A1 | 5/2011 | Niitsu et al. | |
| 2012/0269886 A1 | 10/2012 | Niitsu et al. | |
| 2013/0022665 A1 | 1/2013 | Niitsu et al. | |
| 2013/0071467 A1 | 3/2013 | Niitsu et al. | |

FOREIGN PATENT DOCUMENTS

| | | |
|---|---|---|
| JP | 61-089286 | 5/1986 |
| JP | 61-136584 | 6/1986 |
| JP | 61-254634 | 11/1986 |
| JP | 1-232250 | 9/1989 |
| JP | 4-001239 | 1/1992 |
| JP | 4-108536 | 4/1992 |
| JP | 4-315042 | 11/1992 |
| JP | 2001-501639 A | 2/2001 |
| JP | 2005-507934 A | 3/2005 |
| JP | 2006-254877 | 9/2006 |
| JP | 2006-522140 A | 9/2006 |
| JP | 2009-013145 | 1/2009 |
| JP | 2010-539245 A | 12/2010 |
| WO | WO 98/13025 | 4/1998 |
| WO | WO 98/45463 | 10/1998 |
| WO | WO 2000/007004 | 2/2000 |
| WO | WO 2003/037385 | 5/2003 |
| WO | WO 2003/037385 A1 | 5/2003 |
| WO | WO 2004/089311 A2 | 10/2004 |
| WO | WO 2005/054486 | 6/2005 |
| WO | WO 2006/068232 A1 | 6/2006 |
| WO | WO 2007/099650 | 9/2007 |
| WO | WO 2008/055628 | 5/2008 |
| WO | WO 2009/004214 | 1/2009 |
| WO | WO 2009/036368 A2 | 3/2009 |
| WO | WO 2009/037310 | 3/2009 |
| WO | WO 2009/046974 | 4/2009 |
| WO | WO 2009/046975 | 4/2009 |
| WO | WO 2009/095226 | 8/2009 |
| WO | WO 2009/096487 | 8/2009 |
| WO | WO 2009/116257 | 9/2009 |
| WO | WO 2010/014117 A1 | 2/2010 |
| WO | WO 2010/029760 A1 | 3/2010 |
| WO | WO 2010/061880 | 6/2010 |
| WO | WO 2012/170957 | 12/2012 |

OTHER PUBLICATIONS

Abu Lila et al., "Oxaliplatin targeting to angiogenic vessels by PEGylated cationic liposomes suppresses the angiogenesis in a dorsal air sac mouse model," Journal of Controlled Release, Feb. 20, 2009, 134(1), 18-25.

Almofti et al., "Cationic liposome-mediated gene delivery: Biophysical study and mechanism of internalization," Archives of Biochemistry and Biophysics, Feb. 15, 2003, 410(2), 246-253.

Almofti et al., "Lipoplex size determines lipofection efficiency with or without serum," Molecular Membrane Biology, Jan.-Mar. 2003, 20(1), 35-43.

Brigelius-Flohe and Traber, "Vitamin E: function and metabolism," The FASEB Journal, Jul. 1999, 13(10), 1145-1155.

Feril et al., "Ultrasound enhances liposome-mediated gene transfection," Ultrasonics Sonochemistry, Aug. 2005, 12(6), 489-493.

Fingl et al., "The Pharmacological Basis of Therapeutics," Fourth Edition, 1975, Ch. 1, p. 1.

Hao et al., "Phorbol ester-potentiated liposomal transfection to monocytic PLB-985 cells," Journal of Biochemistry, Dec. 2000, 128(6), 989-998.

Ishiwata et al., "Characteristics and biodistribution of cationic liposomes and their DNA complexes," Journal of Controlled Release, Oct. 2000, 69(1), 139-148.

Jaster, R., "Molecular regulation of pancreatic stellate cell function," Mol. Cancer, Oct. 2004, 3: 26, 1-8.

Justus et al., "Synthesis, Liposomal Preparation, and in Vitro Toxicity of Two Novel Dodecaborate Cluster Lipids for Boron Neutron Capture Therapy," Bioconjugate Chemistry, Jul.-Aug. 2007, 18(4),1287-1293.

Kikuchi et al., "Development of novel cationic liposomes for efficient gene transfer into peritoneal disseminated tumor," Human Gene Therapy, Apr. 1999, 10(6), 947-955.

Kusumoto et al., "Gene transfer effects on various cationic amphiphiles in CHO cells," Cytotechnology, Jun. 2006, 51(2), 57-66.

Madro et al., "The role of pancreatic stellate cells and cytokines in the development of chronic pancreatitis," Med. Sci. Monit., Jul. 2004, 10(7), RA166-170.

Nakashima et al., "Design of a Lipid Bilayer Electrical Device. Strong Chemical Structure Dependence and Molecular Mechanisms on the Phase Transition-Dependent Electrical Impedance Responses of the Device in Air," Journal of Physical Chemistry B, Jan. 1997, 101(2), 215-220.

Pinzani et al., "Liver fibrosis: from the bench to clinical targets," Dig. Liver Dis., Apr. 2004, 36(4), 231-242.

Sato et al., "Resolution of liver cirrhosis using vitamin A—coupled liposomes to deliver siRNA against a collagen-specific chaperone," Nat. Biotechnol., Apr. 2008, 26(4), 431-442.

Scatchard, G., "The attractions of proteins for small molecules and ions," Ann. NY Acad. Sci., May 1949, 51, Molecular Interaction, 660-672.

Serikawa et al., "A new cationic liposome for efficient gene delivery with serum into cultured human cells: a quantitative analysis using two independent fluorescent probes," Biochimica et Biophysica Acta, Biomembranes, Aug. 25, 2000, 1467(2), 419-430.

Serikawa et al., "Enhancement of Gene Expression Efficiency Using Cationic Liposomes on Ovarian Cancer Cells," Drug Delivery, Nov. 2008, 15(8), 523-529.

Tachibana et al., "An assessment of relative transcriptional availability from nonviral vectors," International Journal of Pharmaceutics, Feb. 11, 2004, 270(1-2), 315-321.

Tachibana et al., "Effect of cationic liposomes in an in vitro transcription and translation system," Biological & Pharmaceutical Bulletin, Apr. 2002, 25(4), 529-531.

Tagami et al., "Effect of siRNA in PEG-coated siRNA-lipoplex on anti-PEG IgM production," Journal of Controlled Release, Aug. 4, 2009, 137(3), 234-240.

Umebayashi et al., "Inhibitory effects of three-component hybrid liposomes containing cationic lipids without drugs on the growth of human renal tumor cells in vitro," Biological & Pharmaceutical Bulletin, Sep. 2008, 31(9), 1816-1817.

Hada et al., "The first synthesis of PEG-carotenoid conjugates," Chemical Abstracts Services, XP002690323, Apr. 2011, 8 pages.

International Patent Application No. PCT/US2012/041753: International Search Report dated Jan. 30, 2013, 8 pages.

Li et al., "Synthesis of polyethylene glycol (PEG) derivatives and PEGylated-peptide biopolymer conjugates," Biomacromolecules, Jul.-Aug. 2003, 4(4), 1055-1067.

(56) References Cited

OTHER PUBLICATIONS

Moon et al., "Regulation of adipocyte differentiation by PEGylated all-trans retinoic acid: reduced cytotoxicity and attenuated lipid accumulation," J. Nutr. Biochemistry, May 2007, 18(5), 322-331.
Schreiber et al., "Disperse multiphase systems linked by covalent bonds into a network," Chemical Abstracts Services, XP002690325, 1999, 1 page.
Bentley et al.; "Water-soluble polymer conjugates of retinoic acid"; XP002690324; Database Accession No. 2003:356296; CAPLUS © 2016; 5 pages.
Diec et al.; "Cosmetic or dermatological crosslinked microemulsions"; XP002690326; Database Accession No. 1998:239092; CAPLUS © 2016; 4 pages.
Schreiber et al.; "Crosslinked structures with double lipid membranes or based on peptides"; XP002690327; Database Accession No. 1998:208404; CAPLUS © 2016; 6 pages.
Niitsu et al.; "Retinoid-Liposomes for enhancing modulation of human hsp47 expression for treatment of fibrosis"; XP002690328; Database Accession No. 2012:1819002; CAPLUS © 2016; 14 pages.
European Patent Application No. 15181729.3; Extended Search Report; dated Feb. 18, 2016; 12 pages.
Hada et al.; "The first synthesis of PEG-carotenoid conjugates"; Tetrahedron Letters; vol. 52; 2011; p. 3195-3197.
Horimoto et al.; "Liquid Crystal Compostions"; XP002684897; Database Accession No. 1987:11469; CAPLUS; accessed 2012; one page.
Tagami et al.; "Effect of siRNA in PEG-coated siRNA-lipoplex on anti-PEG IgM productions"; XP002684899; Database Accession No. 2009:776119; CAPLUS; accessed 2012; one page.
European Patent Application No. 15181729.3; Office Action—Article 94(3); dated Nov. 7, 2016; 6 pages.
Pedersen et al.; "Liposomal Formulation of Retinoids Designed for Enzyme Triggered Release"; Journal of Medicinal Chemistry; vol. 53 No. 9; 2010; p. 3782-3792.
Japan Patent Application No. 2016-006249; Office Action—Reason for Refusal; dated Nov. 17, 2016; 13 pages (contains English Translation).

* cited by examiner

COMPOUNDS FOR TARGETING DRUG DELIVERY AND ENHANCING SIRNA ACTIVITY

CROSS REFERENCE TO RELATED APPLICATIONS

This application is a divisional of patent application Ser. No. 13/492,424 filed on Jun. 8, 2012, now U.S. Pat. No. 9,393,315, issued on Jul. 19, 2016, which claims the benefit of U.S. Provisional Application No. 61/494,840 filed Jun. 8, 2011, the entire contents of which are incorporated herein by reference in their entirety.

The instant application contains a Sequence Listing which has been submitted in ASCII format via EFS-Web and is hereby incorporated by reference in its entirety. Said ASCII copy, created on Jul. 20, 2012, is named Sequence_Listing_CRF_NITT0022.txt and is 1,833 bytes in size.

TECHNICAL FIELD

The description is directed to the use of fat-soluble vitamin compounds to target and enhance activity of therapeutic molecules, including siRNA.

BACKGROUND

Fibrosis of the liver can be caused by activated hepatic stellate cells (HSC), resulting in a plurality of types of collagen molecules and fibronectin being deposited on interstitial tissue. This can lead to hepatic cirrhosis, hepatic failure, and/or hepatocellular carcinoma. Further, chronic pancreatitis develops as a result of pancreatic fibrosis by the same mechanism as that for hepatic fibrosis (Madro, 2004, *Med Sci Monit*, 10:RA166-70; Jaster, 2004, *Mol Cancer*, 6:26). Furthermore, stellate cells are present in the vocal cord disorders of the vocal cord and larynx such as vocal cord scarring, vocal cord mucosal fibrosis, and laryngeal fibrosis. To prevent or treat fibrosis in these organs and elsewhere in the body, there is a desire for the development of a drug carrier.

Stellate cells are one of the important target candidates for treating fibrosis (Fallowfield, 2004, *Expert Opin Ther Targets*, 8:423-35; Pinzani, 2004, *Dig Liver Dis*, 36:231-42). During fibrosis, stellate cells are activated by cytokines from nearby cells and are activated. Stellate cells are known as storage cells for vitamin A, and belong to the myofibroblast family, and produce many factors that cause hepatic fibrosis. Therapeutic methods to prevent or treat fibrosis attempt to control collagen metabolism, promotion of the collagen degradation system, and inhibition of activation of stellate cells. However, in all cases, since the specificity of action and/or the organ specificity are low, there are problems with the limited efficacy and with adverse side effects.

Inhibition of collagen protein synthesis has not been established as a therapeutic method. The potency of molecules targeting collagen production is limited because of the possibility of causing side effects. Inhibiting collagen production directly would be an obvious therapeutic method to prevent or treat fibrosis. To do this would require control of one or more of the various types of collagen Types I to IV. A method for accomplishing this may be through HSP47, a collagen-specific molecular chaperone that is essential for intracellular transport and molecular maturation necessary for various types of collagen. Therefore, if in stellate cells the function of HSP47 can be controlled specifically, there is a possibility of inhibiting hepatic fibrosis.

SUMMARY

In one aspect, the description herein provides a compound for facilitating drug delivery to a target cell, consisting of the structure (targeting molecule)$_m$-linker-(targeting molecule)$_n$, wherein the targeting molecule is a retinoid having a specific receptor or activation/binding site on the target cell; wherein m and n are independently 0, 1, 2 or 3; and wherein the linker comprises one or more elements selected from a polyethylene glycol (PEG), a PEG-like molecule, glutarate (Glu), hexyl, glycine$_3$ (Gly$_3$), and 4-aminobutanoate (GluNH).

One embodiment, the retinoid is selected from vitamin A (VA), retinoic acid, tretinoin, adapalene, 4-hydroxy(phenyl)retinamide (4-HPR), retinyl palmitate, retinal, saturated retinoic acid, and saturated, demethylated retinoic acid.

In another embodiment, the linker is selected from bis-amido-PEG, tris-amido-PEG, tetra-amido-PEG, Lys-bis-amido-PEG Lys, Lys-tris-amido-PEG-Lys, Lys-tetr-amido-PEG-Lys, Lys-PEG-Lys, PEG2000, PEG1250, PEG1000, PEG750, PEG550, PEG-Glu, Glu, C6, Gly3, and GluNH.

In another embodiment, the compound is selected from retinoid-PEG-retinoid, (retinoid)$_2$-PEG-(retinoid)$_2$, VA-PEG2000-VA, (retinoid)$_2$-bis-amido-PEG-(retinoid)$_2$, and (retinoid)$_2$-Lys-bis-amido-PEG-Lys-(retinoid)$_2$.

In another embodiment, the compound is a compound of the formula

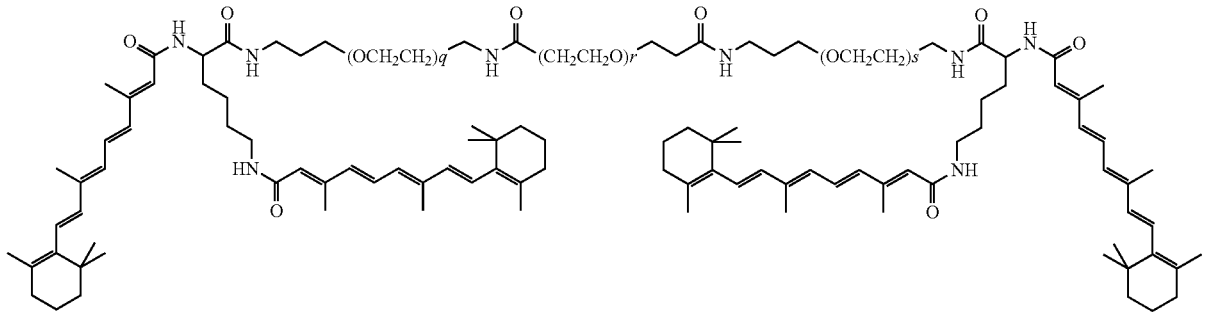

wherein q, r, and s are each independently 1, 2, 3, 4, 5, 6, 7, 8, 9, or 10.

In another embodiment, the formula of the compound comprises

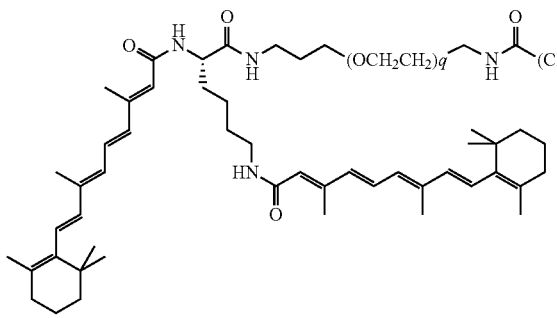 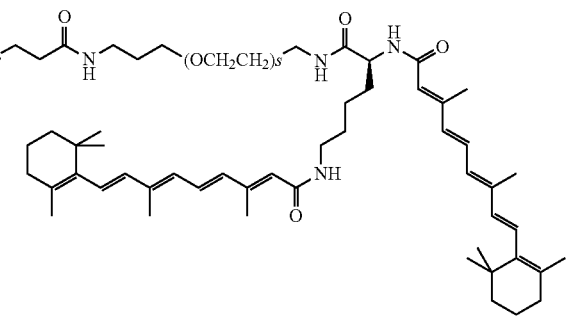

In another aspect, the description herein provides a stellate-cell-specific drug carrier comprising a stellate cell specific amount of a retinoid molecule consisting of the structure (retinoid)$_m$-linker-(retinoid)$_n$, wherein m and n are independently 0, 1, 2 or 3; and wherein the linker comprises a PEG or PEG-like molecule.

In another embodiment, the description herein provides a composition comprising a liposomal composition. In other embodiments, the liposomal composition comprises a lipid vesicle comprising a bilayer of lipid molecules.

In certain embodiments, the retinoid molecule is at least partially exposed on the exterior of the drug carrier before the drug carrier reaches the stellate cell.

In another embodiment, the retinoid is 0.1 mol % to 20 mol % of the lipid molecules. The retinoid will be present in a concentration of about 0.3 to 30 weight percent, based on the total weight of the composition or formulation, which is equivalent to about 0.1 to about 10 mol %.

The description herein also provides embodiments where the lipid molecules comprise one or more lipids selected from HEDC, DODC, HEDODC, DSPE, DOPE, and DC-6-14 (shown below). In another embodiment, the lipid molecules further comprise S104.

In certain embodiments, the drug carrier comprises a nucleic acid.

In other embodiments, the nucleic acid is an siRNA that is capable of knocking down expression of hsp47 mRNA in the stellate cell.

In another aspect, the description herein provides a compound for facilitating drug delivery to a target cell, consisting of the structure (lipid)$_m$-linker-(targeting molecule)$_n$, wherein the targeting molecule is a retinoid or a fat soluble vitamin having a specific receptor or activation/binding site on the target cell; wherein m and n are independently 0, 1, 2 or 3; and wherein the linker comprises a PEG molecule.

In one embodiment, the lipid of the compound is selected from DODC, HEDODC, 1,2-distearoyl-sn-glycero-3-phosphoethanolamine (DSPE), 1,2-dioleoyl-sn-glycero-3-phosphoethanolamine (DOPE), DC, DC-6, and DC-6-14.

In another embodiment, the retinoid is selected from vitamin A, retinoic acid, tretinoin, adapalene, 4-HPR, retinyl palmitate, retinal, saturated retinoic acid, and saturated, demethylated retinoic acid.

In another embodiment of the description herein, the fat-soluble vitamin is vitamin A, vitamin D, vitamin E, or vitamin K.

In another embodiment, the linker is selected from a bond, bis-amido-PEG, tris-amido-PEG, tetra-amido-PEG, Lys-bis-amido-PEG Lys, Lys-tris-amido-PEG-Lys, Lys-tetr-amido-PEG-Lys, Lys-PEG-Lys, PEG2000, PEG1250, PEG1000, PEG750, PEG550, PEG-Glu, Glu, C6, Gly3, and GluNH.

In another embodiment the compound is selected from DSPE-PEG-VA, DSPE-PEG2000-Glu-VA, DSPE-PEG550-VA, DOPE-VA, DOPE-Glu-VA, DOPE-Glu-NH-VA, DOPE-Gly3-VA, DC-VA, and DC-6-VA.

DETAILED DESCRIPTION OF ILLUSTRATIVE EMBODIMENTS

Figure 1:
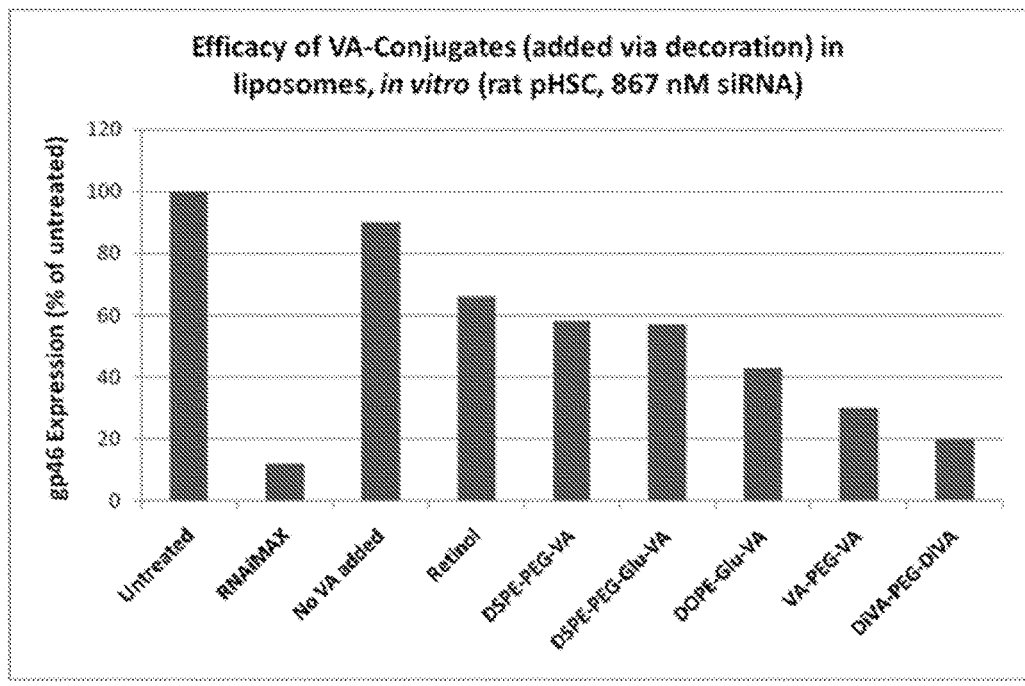
FIG. 1 shows efficacy of VA-conjugates added to liposomes via decoration enhances siRNA activity in vitro in rat primary hepatic stellate cells ("pHSC"). "No VA added" are liposomes without any vitamin A conjugates. "RNAiMAX" is LIPOFECTAMINE® RNAiMAX Transfection Reagent.

Within the scope of the description herein is a compound for facilitating drug delivery to a target cell, consisting of the structure (targeting molecule)$_m$-linker-(targeting molecule)$_n$, wherein the targeting molecule is a retinoid or a fat soluble vitamin having a specific receptor or activation/binding site on the target cell; and wherein m and n are independently 0, 1, 2, or 3; and wherein the linker comprises a bond, a PEG or PEG-like molecule, and is designated "Formula A".

The description herein also includes a compound for facilitating drug delivery to a target cell, consisting of the structure (lipid)$_m$-linker-(targeting molecule)$_n$, wherein the targeting molecule is a retinoid or a fat soluble vitamin having a specific receptor on the target cell; wherein m and n are independently 0, 1, 2, or 3; and wherein the linker comprises a bond, a PEG or PEG-like molecule and is designated "Formula B".

It has heretofore been discovered that the compounds of Formula A or Formula B impart properties to the formulations of the description herein not previously seen. Formulations including the compounds of Formula A or Formula B result in superior reduction in gene expression, as compared to formulations that do not include these compounds. Particularly surprising is the ability of formulations of the description herein that include compounds of Formula A to reduce the expression of HSP47.

In certain preferred embodiments, the retinoid is selected from the group consisting of vitamin A, retinoic acid, tretinoin, adapalene, 4-HPR, retinyl palmitate, retinal, saturated retinoic acid, and saturated, demethylated retinoic acid.

Preferred embodiments include compounds where the linker is selected from a bond, bis-amido-PEG, tris-amido-PEG, tetra-amido-PEG, Lys-bis-amido-PEG Lys, Lys-tris-amido-PEG-Lys, Lys-tetra-amido-PEG-Lys, Lys-PEG-Lys, PEG2000, PEG1250, PEG1000, PEG750, PEG550, PEG-Glu, Glu, C6, Gly3, and GluNH. In other embodiments, the PEG is mono disperse.

Another embodiment provides a compound where Formula A is selected from retinoid-PEG-retinoid, (retinoid)$_2$-PEG-(retinoid)$_2$, VA-PEG2000-VA, (retinoid)$_2$-bis-amido-PEG-(retinoid)$_2$, and (retinoid)$_2$-Lys-bis-amido-PEG-Lys-(retinoid)$_2$.

In another preferred embodiment, the compound is the formula

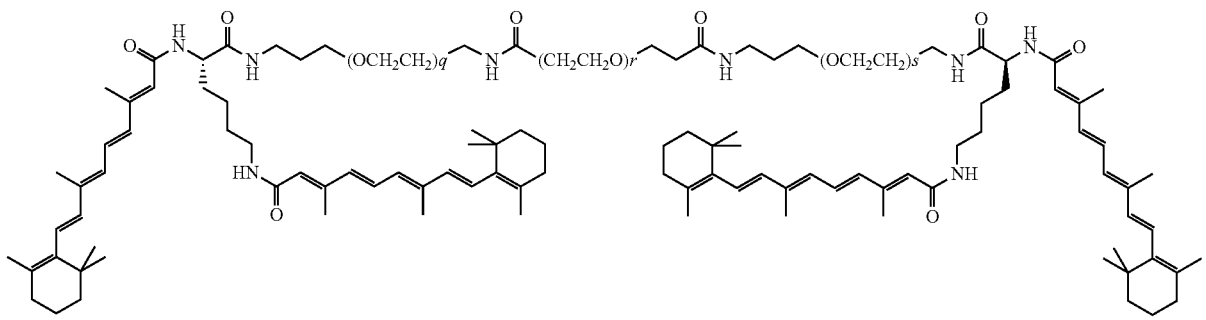

wherein q, r, and s are each independently 1, 2, 3, 4, 5, 6, 7, 8, 9, or 10.

In other preferred embodiments, the formula of the compound comprises

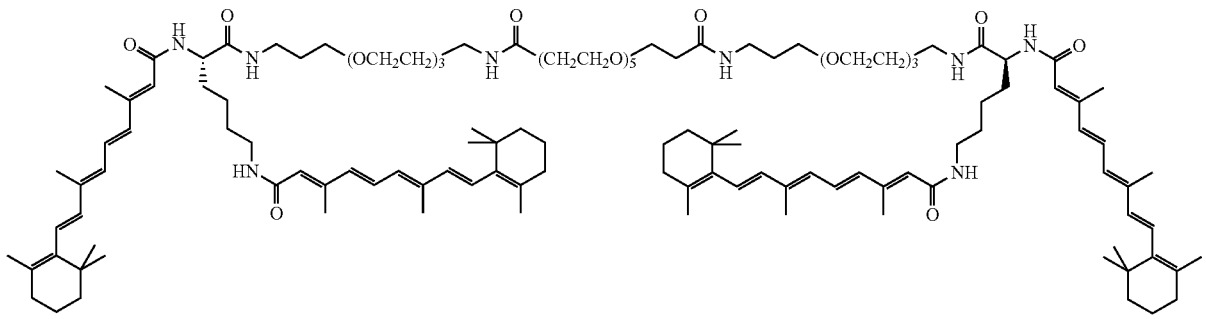

Other embodiments of the description herein include the structures shown in Table 1, below

TABLE 1

| Lipid Name | Compound Structure |
|---|---|
| SatDiVA | (structure shown) |
| SimDiVA | (structure shown) |

TABLE 1-continued
| Lipid Name | Compound Structure |
|---|---|
| DiVA-PEG18 | 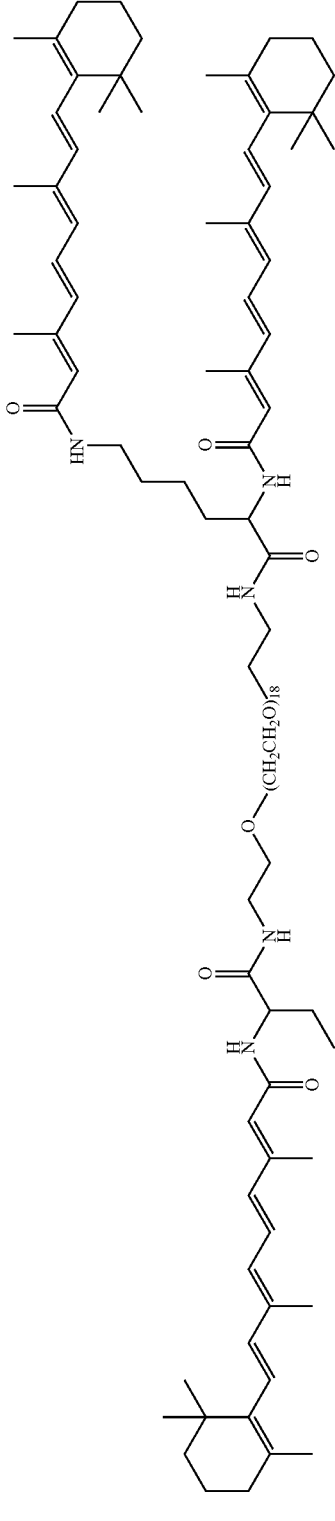 |
| TriVA | 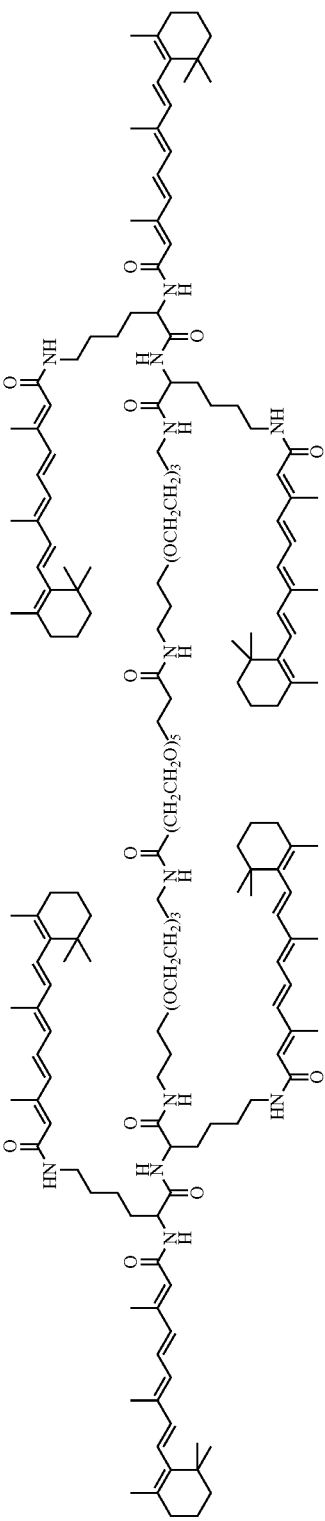 |

TABLE 1-continued

| Lipid Name | Compound Structure |
|---|---|
| 4TTNPB | 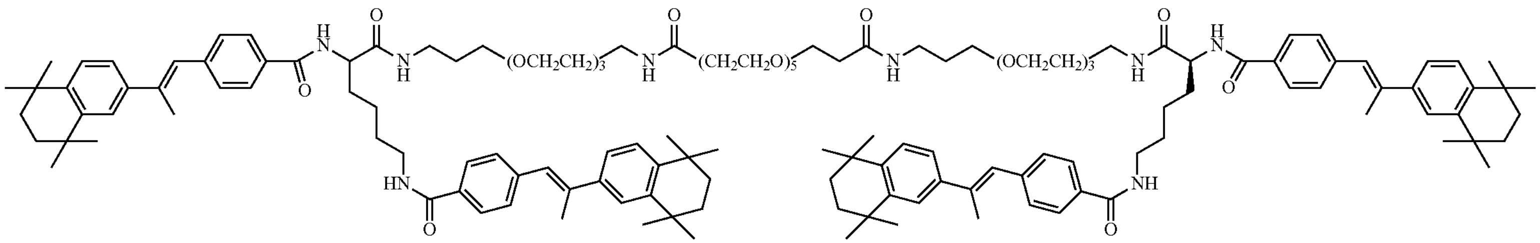 |
| 4MYR | 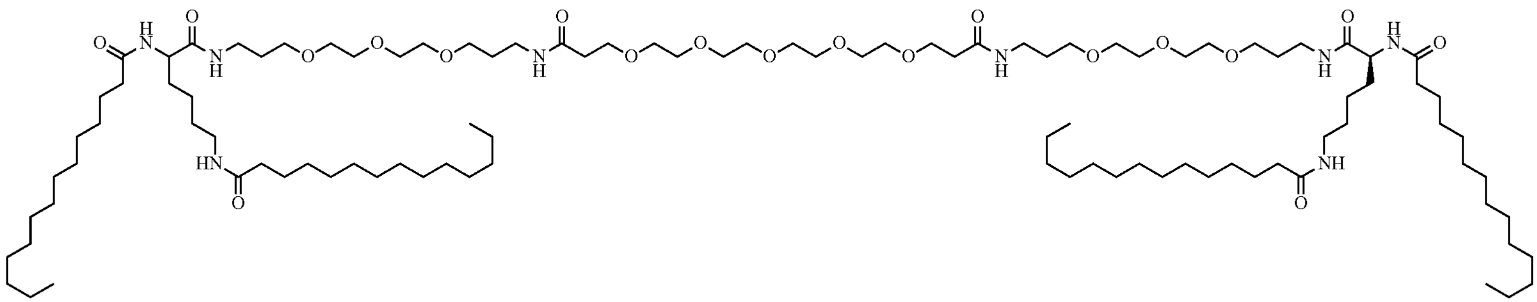 [SMILES: CCCCCCCCCCCCCC(=O)NCCCCC(NC(=O)CCCCCCCCCCCCC)C(=O)NCCCOCCOCCOCCCNC(=O)CCOCCOCCOCCOCCOCCC(=O)NCCCOCCOCCOCCCNC(=O)[C@H](CCCCNC(=O)CCCCCCCCCCCCC)NC(=O)CCCCCCCCCCCCC] |
| DiVA-242 | 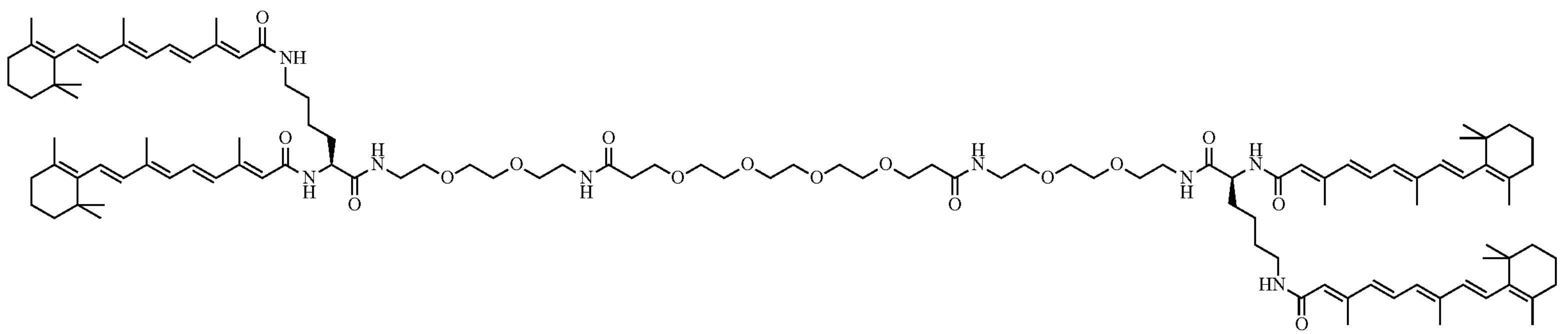 [SMILES: CC1=C(/C=C/C(C)=C/C=C/C(C)=C/C(=O)NCCCC[C@H](NC(=O)/C=C(C)/C=C/C=C(C)/C=C/C2=C(C)CCCC2(C)C)C(=O)NCCOCCOCCNC(=O)CCOCCOCCOCCOCCC(=O)NCCOCCOCCNC(=O)[C@H](CCCCNC(=O)/C=C(C)/C=C/C=C(C)/C=C/C2=C(C)CCCC2(C)C)NC(=O)/C=C(C)/C=C/C=C(C)/C=C/C2=C(C)CCCC2(C)C)C(C)(C)CCC1] |

Also within the scope of the description herein are formulations comprising at least one compound of Formula A or B and siRNA. It is envisioned that any siRNA molecule can be used with the compound described herein. Examples of siRNA include the following.

```
                                         (SEQ. ID. NO. 1)
Sense (5'->3') GGACAGGCCUCUACAACUATT (SEQ. ID. NO. 2)
Antisense (3'->5') TTCCUGUCCGGAGAUGUUGAU
and
                                         (SEQ. ID. NO. 3)
Sense (5'->3') GGACAGGCCUGUACAACUATT (SEQ. ID. NO. 4)
Antisense (3'->5') TTCCUGUCCGGACAUGUUGAU
```

Other embodiments include a stellate-cell-specific drug carrier comprising a liposomal composition. The liposomal composition can comprise a lipid vesicle comprising a bilayer of lipid molecules. In certain embodiments it may preferred that the retinoid molecule is at least partially exposed on the exterior of the drug carrier before the drug carrier reaches the stellate cell.

Certain embodiments of the description herein provide that the lipid molecules comprise one or more lipids selected from the group consisting of HEDC, DODC, HEDODC, DSPE, DOPE, and DC-6-14. In other embodiments, the lipid molecules further comprise S104.

HEDC

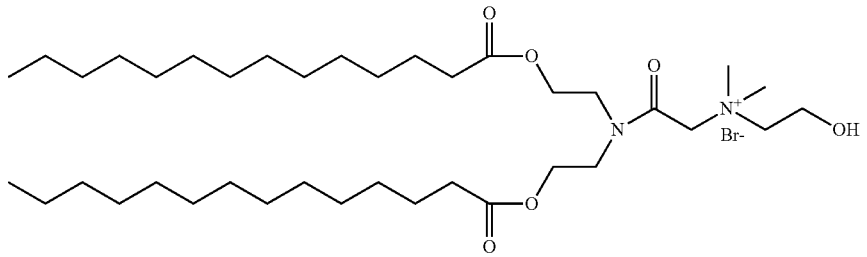

S104

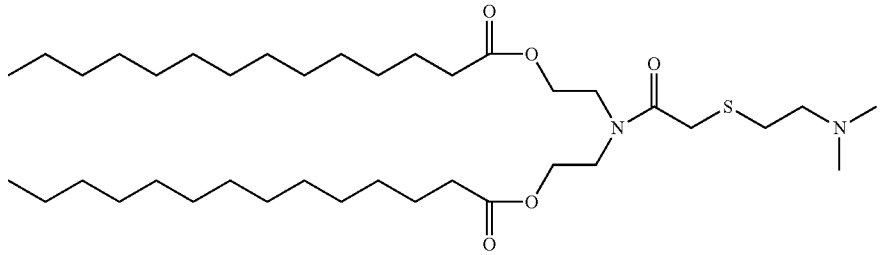

DODC

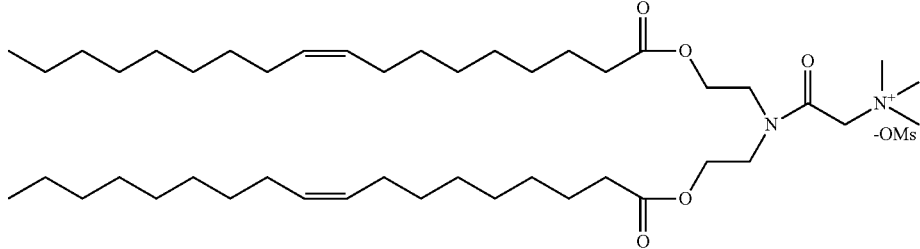

HEDODC

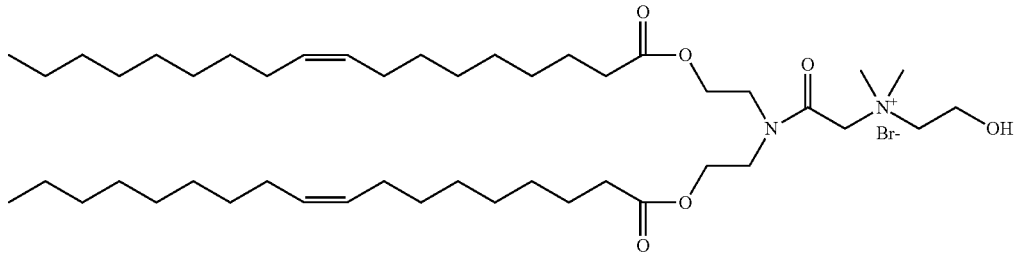

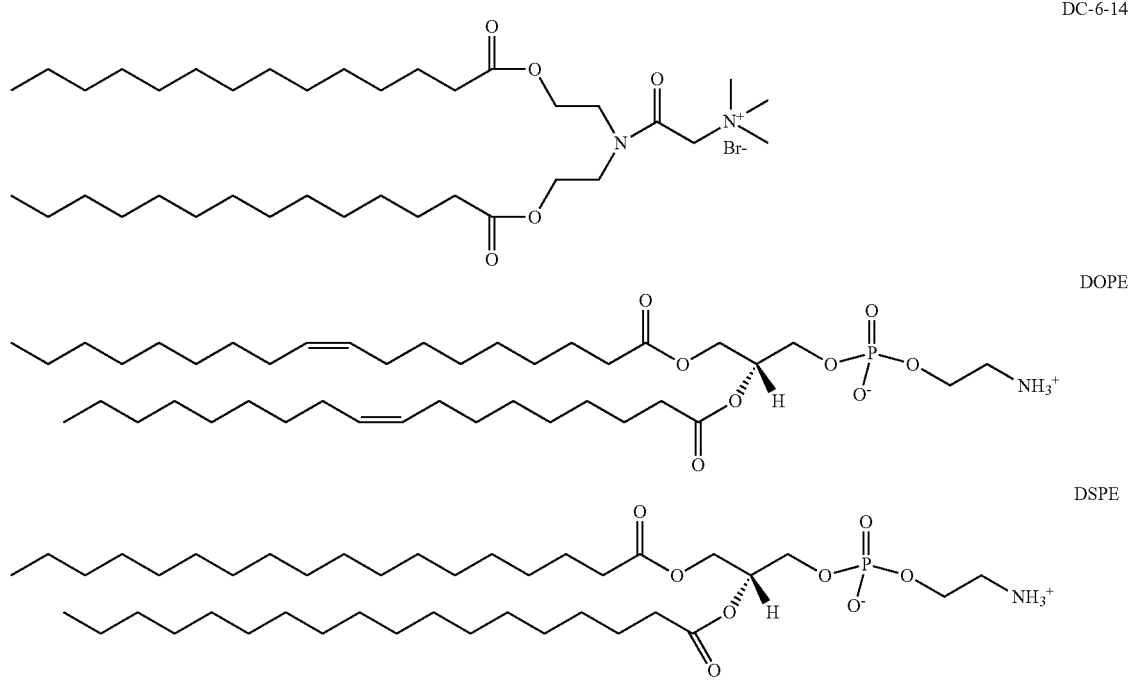

In some embodiments, the siRNA will be encapsulated by the liposome so that the siRNA is inaccessible to the aqueous medium. In other embodiments, the siRNA will not be encapsulated by the liposome. In such embodiments, the siRNA can be complexed on the outer surface of the liposome. In these embodiments, the siRNA is accessible to the aqueous medium.

Other embodiments include stellate-cell-specific drug carrier comprising a liposomal composition. The liposomal composition can comprise a lipid vesicle comprising a bilayer of lipid molecules. In other embodiments, the retinoid molecule is at least partially exposed on the exterior of the drug carrier before the drug carrier reaches the stellate cell.

In certain preferred embodiments, the retinoid is 0.1 mol % to 20 mol % of the lipid molecules.

In some embodiments, the compositions include PEG-conjugated lipids, which are known in the art per se, including PEG-phospholipids and PEG-ceramides, or one or more molecules selected from PEG2000-DSPE, PEG2000-DPPE, PEG2000-DMPE, PEG2000-DOPE, PEG1000-DSPE, PEG1000-DPPE, PEG1000-DMPE, PEG1000-DOPE, PEG550-DSPE, PEG550-DPPE, PEG-550DMPE, PEG-1000DOPE, PEG-cholesterol, PEG2000-ceramide, PEG1000-ceramide, PEG750-ceramide, and PEG550-ceramide.

In some embodiments, the compositions include one or more phospholipids, e.g., selected from 1,2-distearoyl-sn-glycero-3-phosphocholine ("DSPC"), dipalmitoylphosphatidylcholine ("DPPC"), 1,2-dipalmitoyl-sn-glycero-3-phosphoethanolamine ("DPPE"), and 1,2-dioleoyl-sn-glycero-3-phosphoethanolamine ("DOPE"). Preferably, the helper phospholipid is DOPE.

Also within the scope of the description herein are pharmaceutical formulations that include any of the aforementioned compounds in addition to a pharmaceutically acceptable carrier or diluent. Pharmaceutical formulations will include at least one therapeutic agent. Preferably, the therapeutic agent is an siRNA. It is envisioned that any siRNA molecule can be used as described herein. siRNA, e.g., include SEQ ID NO: 1, SEQ ID NO: 2, SEQ ID NO: 3, and SEQ ID NO: 4.

In preferred formulations comprising siRNA, the siRNA is encapsulated by the liposome. In other embodiments, the siRNA is outside of the liposome. In those embodiments, the siRNA can be complexed to the outside of the liposome.

A useful range of cationic lipid:siRNA (lipid nitrogen to siRNA phosphate ratio, "N:P") is 0.2 to 5.0. A particularly preferred range of N:P is 1.5 to 2.5 for compositions and formulations of the description.

Preferred formulations include those comprising HEDC:S104:DOPE:cholesterol:PEG-DMPE:DiVA-PEG-DiVA (20:20:30:25:5:2 molar ratio) and HEDC:S104:DOPE:cholesterol:PEG-DMPE:DiVA-PEG-DiVA (20:20:30:25:5:2 molar ratio) wherein the DiVA-PEG-DiVA is co-solubilized; as well as DODC:DOPE:cholesterol:PEG-lipid:DiVA-PEG-DiVA (50:10:38:2:5 molar ratio) and DODC:DOPE:cholesterol:PEG-lipid:DiVA-PEG-DiVA formulations, wherein the DiVA-PEG-DiVA is co-solubilized.

Other preferred formulations include those comprising HEDODC:DOPE:cholesterol-PEG-lipid:DiVA-PEG-DiVA (50:10:38:2:5 molar ratio) and HEDODC:DOPE:cholesterol-PEG-lipid:DiVA-PEG-DiVA formulations, wherein the DiVA-PEG-DiVA is co-solubilized.

Other preferred formulations include those comprising DC-6-14:DOPE:cholesterol: DiVA-PEG-DiVA (40:30:30:5, molar ratios) and DC-6-14:DOPE:cholesterol: DiVA-PEG-DiVA, wherein the DiVA-PEG-DiVA is co-solubilized.

Also within the scope of the description herein are methods of delivering a therapeutic agent to a patient. These methods comprise providing a pharmaceutical formulation including any of the foregoing compositions and a pharmaceutically acceptable carrier or diluent, and administering the pharmaceutical formulation to the patient.

Definitions

As referred to herein, "alkyl" refers to a straight or branched fully saturated (no double or triple bonds) hydrocarbon group, for example, a group having the general formula $-C_nH_{2n+1}$. The alkyl group may have 1 to 50 carbon atoms (whenever it appears herein, a numerical range such as "1 to 50" refers to each integer in the given range; e.g., "1 to 50 carbon atoms" means that the alkyl group may consist of 1 carbon atom, 2 carbon atoms, 3 carbon atoms, etc., up to and including 50 carbon atoms, although the present definition also covers the occurrence of the term "alkyl" where no numerical range is designated). The alkyl group may also be a medium size alkyl having 1 to 30 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl and the like.

As referred to herein, "alkenyl" refers to an alkyl group that contains in the straight or branched hydrocarbon chain one or more double bonds. An alkenyl group may be unsubstituted or substituted. When substituted, the substituent(s) may be selected from the same groups disclosed above with regard to alkyl group substitution unless otherwise indicated.

As referred to herein, "alkynyl" refers to an alkyl group that contains in the straight or branched hydrocarbon chain one or more triple bonds. An alkynyl group may be unsubstituted or substituted. When substituted, the substituent(s) may be selected from the same groups disclosed above with regard to alkyl group substitution unless otherwise indicated.

As referred to herein, "halogen" refers to F, Cl, Br, and I.

As referred to herein, "mesylate" refers to $-OSO_2CH_3$.

As referred to herein, the term "pharmaceutical formulation" refers to a mixture of a composition disclosed herein with one or more other chemical components, such as diluents or additional pharmaceutical carriers. The pharmaceutical formulation facilitates administration of the composition to an organism. Multiple techniques of administering a pharmaceutical formulation exist in the art including, but not limited to injection and parenteral administration.

As referred to herein, the term "pharmaceutical carrier" refers to a chemical compound that facilitates the incorporation of a compound into cells or tissues. For example dimethyl sulfoxide (DMSO) is a commonly utilized carrier as it facilitates the uptake of many organic compounds into the cells or tissues of an organism As referred to herein, the term "diluent" refers to chemical compounds diluted in water that will dissolve the formulation of interest (e.g., the formulation that can include a compound, a retinoid, a second lipid, a stabilizing agent, and/or a therapeutic agent) as well as stabilize the biologically active form of the formulation. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of the formulation. As referred to herein, an "excipient" refers to an inert substance that is added to a formulation to provide, without limitation, bulk, consistency, stability, binding ability, lubrication, disintegrating ability, etc., to the composition. A "diluent" is a type of excipient.

As referred to herein, "therapeutic agent" refers to a compound that, upon administration to a mammal in a therapeutically effective amount, provides a therapeutic benefit to the mammal. A therapeutic agent may be referred to herein as a drug. Those skilled in the art will appreciate that the term "therapeutic agent" is not limited to drugs that have received regulatory approval. A "therapeutic agent" can be operatively associated with a compound as described herein, a retinoid, and/or a second lipid. For example, a second lipid as described herein can form a liposome, and the therapeutic agent can be operatively associated with the liposome, e.g., as described herein.

As referred to herein, "lipoplex formulations" refer to those formulations wherein the siRNA is outside of the liposome. In preferred lipoplex formulations, the siRNA is complexed to the outside of the liposome. Other preferred lipoplex formulations include those wherein the siRNA is accessible to any medium present outside of the liposome.

As referred to herein, "liposome formulations" refer to those formulations wherein the siRNA is encapsulated within the liposome. In preferred liposome formulations, the siRNA is inaccessible to any medium present outside of the liposome.

As referred to herein, the term "co-solubized" refers to the addition of a component to the cationic lipid mixture before the empty vesicle is formed.

As referred to herein, the term "decorated" refers to the addition of a component after vesicle formation.

As referred to herein, "DC-6-14" refers to the following cationic lipid compound:

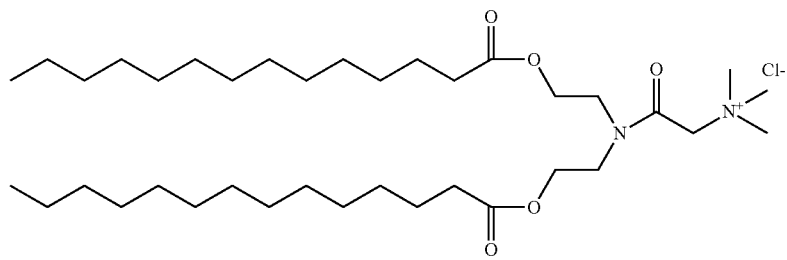

DC-6-14

As referred to herein, "DODC" refers to the following cationic lipid compound:

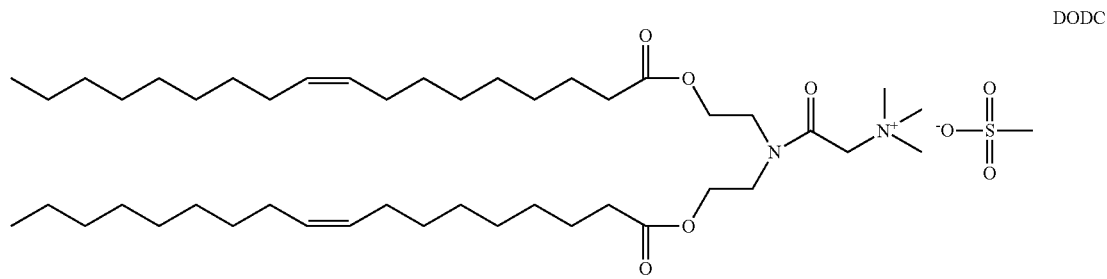

DODC

As referred to herein, "HEDODC" refers to the following cationic lipid compound:

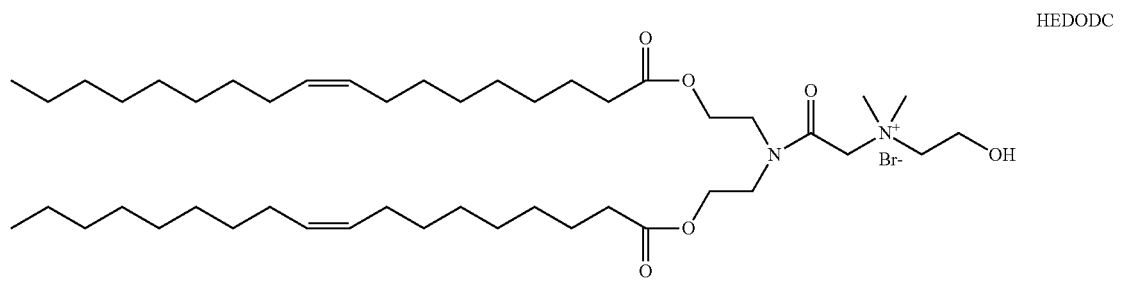 [SMILES: CCCCCCCC/C=C\CCCCCCCC(=O)OCCN(CCOC(=O)CCCCCCC/C=C\CCCCCCCC)C(=O)C[N+](C)(C)CCO ; [Br-]]

HEDODC

As referred to herein, a "retinoid" is a member of the class of compounds consisting of four isoprenoid units joined in a head-to-tail manner, see Moss, BIOCHEMICAL NOMENCLATURE AND RELATED DOCUMENTS, 2nd Ed. Portland Press, pp. 247-251 (1992). "Vitamin A" is the generic descriptor for retinoids exhibiting qualitatively the biological activity of retinol. As referred to herein, retinoid refers to natural and synthetic retinoids including first generation, second generation, and third generation retinoids. Examples of naturally occurring retinoids include, but are not limited to, (1) 11-cis-retinal, (2) all-trans retinol, (3) retinyl palmitate, (4) all-trans retinoic acid, and (5) 13-cis-retinoic acids. Furthermore, the term "retinoid" encompasses retinols, retinals, retinoic acids, rexinoids, demethylated and/or saturated retinoic acids, and derivatives thereof.

As referred to herein, "Vitamin D" is a generic descriptor for a group of vitamins having antirachitic activity. The vitamin D group includes: vitamin $D_2$ (calciferol), vitamin $D_3$ (irradiated 22-dihydroergosterol), vitamin $D_4$ (irradiated dehydrositosterol) and vitamin $D_5$ (irradiated dehydrositosterol).

As referred to herein, "Vitamin E" is a generic descriptor for a group of molecules with antioxidant activity. The vitamin E family includes α-tocopherol, β-tocopherol, γ-tocopherol and δ-tocopherol, with α-tocopherol being the most prevalent. (Brigelius-Flohe, 1999, *FASEB J*, 13:1145-55).

As referred to herein, "Vitamin K" is generic descriptor for an anti-hemorrhagic factor and includes vitamin $K_1$ (phytonadione), vitamin $K_2$ (menaquinone), vitamin $K_3$, vitamin $K_4$ and vitamin $K_5$. Vitamins $K_1$ and $K_2$ are natural, while $K_{3-5}$ are synthetic.

As referred to herein, "retinoid-linker-lipid molecule" refers to a molecule that includes at least one retinoid moiety attached to at least one lipid moiety through at least one linker such as, for example, a PEG moiety.

As referred to herein, "retinoid linker-retinoid molecule" refers to a molecule that includes at least one retinoid moiety attached to at least one other retinoid moiety (which may be the same or different) through at least one linker such as, for example, a PEG moiety.

As referred to herein, the terms "lipid" and "lipophilic" are referred to herein in their ordinary meanings as understood by those skilled in the art. Non-limiting examples of lipids and lipophilic groups include fatty acids, sterols, $C_2$-$C_{50}$ alkyl, $C_2$-$C_{50}$ heteroalkyl, $C_2$-$C_{50}$ alkenyl, $C_2$-$C_{50}$ heteroalkenyl, $C_5$-$C_{50}$ aryl, $C_5$-$C_{50}$ heteroaryl, $C_2$-$C_{50}$ alkynyl, $C_2$-$C_{50}$ heteroalkynyl, $C_2$-$C_{50}$ carboxyalkenyl, and $C_2$-$C_{50}$ carboxyheteroalkenyl. A fatty acid is a saturated or unsaturated long-chain monocarboxylic acid that contains, for example, 12 to 24 carbon atoms A lipid is characterized as being essentially water insoluble, having a solubility in water of less than about 0.01% (weight basis). As referred to herein, the terms "lipid moiety" and "lipophilic moiety" refers to a lipid or portion thereof that has become attached to another group. For example, a lipid group may become attached to another compound (e.g., a monomer) by a chemical reaction between a functional group (such as a carboxylic acid group) of the lipid and an appropriate functional group of a monomer.

As referred to herein, "siRNA" refers to small interfering RNA, also known in the art as short interfering RNA or silencing RNA. siRNA is a class of double stranded RNA molecules that have a variety of effects known in the art, the most notable being the interference with the expression of specific genes and protein expression.

As referred to herein, "encapsulated by the liposome" refers to a component being substantially or entirely within the liposome structure.

As referred to herein, "accessible to the aqueous medium" refers to a component being able to be in contact with the aqueous medium.

As referred to herein, "inaccessible to the aqueous medium" refers to a component not being able to be in contact with the aqueous medium.

As referred to herein, "complexed on the outer surface of the liposome" refers to refers to a component being operatively associated with the outer surface of the liposome.

As referred to herein, "localized on the outer surface of the liposome" refers to a component being at or near the outer surface of the liposome.

As referred to herein, "charge complexed" refers to an electrostatic association.

As referred to herein, the term "operatively associated" refers to an electronic interaction between a compound as described herein, a therapeutic agent, a retinoid, and/or a second lipid. Such interaction may take the form of a chemical bond, including, but not limited to, a covalent bond, a polar covalent bond, an ionic bond, an electrostatic association, a coordinate covalent bond, an aromatic bond, a hydrogen bond, a dipole, or a van der Waals interaction. Those of ordinary skill in the art understand that the relative strengths of such interactions may vary widely.

The term "liposome" is referred to herein in its ordinary meaning as understood by those skilled in the art, and refers to a lipid bilayer structure that contains lipids attached to polar, hydrophilic groups which form a substantially closed structure in aqueous media. In some embodiments, the liposome can be operatively associated with one or more compounds, such as a therapeutic agent and a retinoid or retinoid conjugate. A liposome may be comprised of a single lipid bilayer (i.e., unilamellar) or it may comprised of two or more concentric lipid bilayers (i.e., multilamellar). Additionally, a liposome can be approximately spherical or ellipsoidal in shape.

The term "facilitating drug delivery to a target cell" refers the enhanced ability of the present retinoid or fat soluble vitamin compounds to enhance delivery of a therapeutic molecule such as siRNA to a cell. While not intending to be bound by theory, the retinoid or fat-soluble vitamin compound interacts with a specific receptor or [activation/binding site] on a target cell with specificity that can be measured. For example, binding is generally consider specific when binding affinity ($K_a$) of $10^6 M^{-1}$ or greater, preferably $10^7 M^{-1}$ or greater, more preferably $10^8 M^{-1}$ or greater, and most preferably $10^9 M^{-1}$ or greater. The binding affinity of an antibody can be readily determined by one of ordinary skill in the art, for example, by Scatchard analysis (Scatchard, 1949, *Ann NY Acad Sci*, 51:660).

In another aspect, the present disclosure relates to a pharmaceutical formulation comprising one or more physiologically acceptable surface active agents, pharmaceutical carriers, diluents, excipients, and suspension agents, or a combination thereof; and a formulation (e.g., the formulation that can include a compound, a retinoid, a second lipid, a stabilizing agent, and/or a therapeutic agent) disclosed herein. Acceptable additional pharmaceutical carriers or diluents for therapeutic use are well known in the pharmaceutical art, and are described, for example, in REMINGTON'S PHARMACEUTICAL SCIENCES, 18th Ed., Mack Publishing Co., Easton, Pa. (1990), incorporated herein by reference in its entirety. Preservatives, stabilizers, dyes, and the like may be provided in the pharmaceutical formulation. For example, sodium benzoate, ascorbic acid and esters of p-hydroxybenzoic acid may be added as preservatives. In addition, antioxidants and suspending agents may be used.

In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The pharmaceutical formulations described herein can be administered to a human patient per se, or in pharmaceutical formulations where they are mixed with other active ingredients, as in combination therapy, or suitable pharmaceutical carriers or excipient(s). Techniques for formulation and administration of the compounds of the instant application may be found in REMINGTON'S PHARMACEUTICAL SCIENCES.

Suitable routes of administration may include, for example, parenteral delivery, including intramuscular, subcutaneous, intravenous, intramedullary injections, as well as intrathecal, direct intraventricular, intraperitoneal, intranasal, or intraocular injections. The formulation (e.g., the formulation that can include a compound, a retinoid, a second lipid, a stabilizing agent, and/or a therapeutic agent) can also be administered in sustained or controlled release dosage forms, including depot injections, osmotic pumps, and the like, for prolonged and/or timed, pulsed administration at a predetermined rate. Additionally, the route of administration may be local or systemic.

The pharmaceutical formulations may be manufactured in a manner that is itself known, e.g., by means of conventional mixing, dissolving, granulating, dragee-making, levigating, emulsifying, encapsulating, entrapping or tableting processes.

Pharmaceutical formulations may be formulated in any conventional manner using one or more physiologically acceptable pharmaceutical carriers comprising excipients and auxiliaries which facilitate processing of the active compounds into preparations which can be used pharmaceutically. Proper formulation is dependent upon the route of administration chosen. Any of the well-known techniques, pharmaceutical carriers, and excipients may be used as suitable and as understood in the art; e.g., in REMINGTON'S PHARMACEUTICAL SCIENCES.

Injectables can be prepared in conventional forms, either as liquid solutions or suspensions, solid forms suitable for solution or suspension in liquid prior to injection, or as emulsions. Suitable excipients are, for example, water, saline, sucrose, glucose, dextrose, mannitol, lactose, lecithin, albumin, sodium glutamate, cysteine hydrochloride, and the like. In addition, if desired, the injectable pharmaceutical formulations may contain minor amounts of non-toxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations may be utilized.

Pharmaceutical formulations for parenteral administration, e.g., by bolus injection or continuous infusion, include aqueous solutions of the active formulation (e.g., the formulation that can include a compound, a retinoid, a second lipid, a stabilizing agent, and/or a therapeutic agent) in water-soluble form. Additionally, suspensions of the active compounds may be prepared as appropriate oily injection suspensions. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The formulations may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition to the preparations described previously, the formulations may also be formulated as a depot preparation. Such long acting formulations may be administered by intramuscular injection. Thus, for example, the formulations (e.g., the formulation that can include a compound, a retinoid, a second lipid, a stabilizing agent, and/or a therapeutic agent) may be formulated with suitable polymeric or hydrophobic materials (for example as an emulsion in an acceptable oil) or ion exchange resins, or as sparingly soluble derivatives, for example, as a sparingly soluble salt.

Some embodiments herein are directed to a method of delivering a therapeutic agent to a cell. For example, some embodiments are directed to a method of delivering a therapeutic agent such as siRNA into a cell. Suitable cells for use according to the methods described herein include prokaryotes, yeast, or higher eukaryotic cells, including plant and animal cells (e.g., mammalian cells). In some embodiments, the cells can be human fibrosarcoma cells (e.g., HT1080 cell line). In other embodiments, the cells can be cancer cells. Cell lines which are model systems for cancer may be used, including but not limited to breast cancer (MCF-7, MDA-MB-438 cell lines), U87 glioblastoma cell line, B16F0 cells (melanoma), HeLa cells (cervical cancer), A549 cells (lung cancer), and rat tumor cell lines GH3 and 9L. In these embodiments, the formulations described herein can be used to transfect a cell. These embodiments may include contacting the cell with a formulation described herein that includes a therapeutic agent, to thereby deliver a therapeutic agent to the cell.

Disclosed herein are methods for treating a condition characterized by abnormal fibrosis, which may include administering a therapeutically effective amount of a formulation described herein. Conditions characterized by abnormal fibrosis may include cancer and/or a fibrotic disease. Types of cancer that may be treated or ameliorated by a formulation described herein include, but are not limited to, lung cancer, pancreatic cancer, breast cancer, liver cancer, stomach cancer, and colon cancer. In an embodiment, the cancer that may be treated or ameliorated is pancreatic cancer. In another embodiment, the cancer that may be treated or ameliorated is lung cancer. Types of fibrotic disease that may be treated or ameliorated by a formulation described herein include, but are not limited to, hepatic fibrosis, hepatic cirrhosis, pancreatitis, pancreatic fibrosis, cystic fibrosis, vocal cord scarring, vocal cord mucosal fibrosis, laryngeal fibrosis, pulmonary fibrosis, idiopathic pulmonary fibrosis, cystic fibrosis, myelofibrosis, retroperitoneal fibrosis, and nephrogenic systemic fibrosis. In an embodiment, the condition that may be treated or ameliorated is hepatic fibrosis.

The formulations or pharmaceutical compositions described herein may be administered to the subject by any suitable means. Non-limiting examples of methods of administration include, among others, (a) administration via injection, subcutaneously, intraperitoneally, intravenously, intramuscularly, intradermally, intraorbitally, intracapsularly, intraspinally, intrasternally, or the like, including infusion pump delivery; (b) administration locally such as by injection directly in the renal or cardiac area, e.g., by depot implantation; as well as deemed appropriate by those of skill in the art for bringing the active compound into contact with living tissue.

Pharmaceutical compositions suitable for administration include formulations (e.g., the formulation that can include a compound, a retinoid, a second lipid, a stabilizing agent, and/or a therapeutic agent) where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of composition effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively dosages may be based and calculated upon the surface area of the patient, as understood by those of skill in the art.

The exact formulation, route of administration and dosage for the pharmaceutical compositions can be chosen by the individual physician in view of the patient's condition. (See e.g., GOODMAN & GILMAN'S THE PHARMACOLOGICAL BASIS OF THERAPEUTICS, hereby incorporated herein by reference in its entirety). Typically, the dose range of the composition administered to the patient can be from about 0.5 to about 1000 mg/kg of the patient's body weight.

The dosage may be a single one or a series of two or more given in the course of one or more days, as is needed by the patient. In instances where human dosages for compounds have been established for at least some condition, the dosages will be about the same, or dosages that are about 0.1% to about 500%, more preferably about 25% to about 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, a dose of about 0.1 mg to 2000 mg of each active ingredient, preferably about 1 mg to about 500 mg, e.g. 5 to 200 mg. In other embodiments, an intravenous, subcutaneous, or intramuscular dose of each active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free base. In some embodiments, the formulation is administered 1 to 4 times per day. Alternatively the formulations may be administered by continuous intravenous infusion, preferably at a dose of each active ingredient up to about 1000 mg per day. As will be understood by those of skill in the art, in certain situations it may be necessary to administer the formulations disclosed herein in amounts that exceed, or even far exceed, the above-stated, preferred dosage range in order to effectively and aggressively treat particularly aggressive diseases or infections. In some embodiments, the formulations will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of formulation administered may be dependent on the subject being treated, on the subject's weight, the severity of the affliction, the manner of administration and the judgment of the prescribing physician.

Formulations disclosed herein (e.g., the formulation that can include a compound, a retinoid, a second lipid, a stabilizing agent, and/or a therapeutic agent) can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The formulations may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound formulated in a compatible pharmaceutical carrier may also be prepared, placed in an appropriate container, and labeled for treatment of an indicated condition.

It is understood that, in any compound described herein having one or more stereocenters, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound having one or more double bond(s) generating geometrical isomers that can be defined as E or Z each double bond may independently be E or Z a mixture thereof. Likewise, all tautomeric forms are also intended to be included.

The description herein can be further exemplified by reference to the following examples. These examples are illustrative, only, and are not intended to limit the description herein.

EXAMPLES

Example 1 Synthesis of DOPE-Glu-VA

Preparation of DOPE-Glu-VA: (Z)-(2R)-3-(((2-(5-((((2E,4E,6E,8E)-3,7-dimethyl-9-(2,6,6-trimethylcyclohex-1-en-1-yl)nona-2,4,6,8-tetraen-1-yl)oxy)-5-oxopentanamido)ethoxy)(hydroxy)phosphoryl)oxy)propane-1,2-diyl dioleate

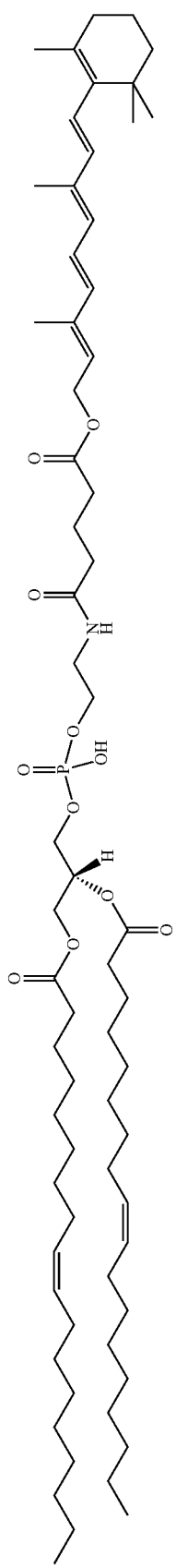

Preparation of Intermediate 1: 5-(((2E,4E,6E,8E)-3,7-dimethyl-9-(2,6,6-trimethylcyclohex-1-en-1-yl)nona-2,4,6,8-tetraen-1-yl)oxy)-5-oxopentanoic acid

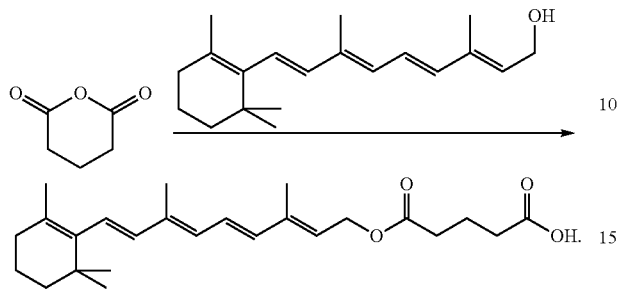

Glutaric anhydride (220 mg, 1.93 mmol) and retinol (500 mg, 1.75 mmol) were dissolved in dichloromethane (5 mL) in an amber-colored vial. Triethylamine (513 μl, 3.68 mmol) was added and the vial was flushed with argon. Reaction mixture was stirred at room temperature for 4 hours. The material was concentrated and purified by silica gel chromatography with a dichloromethane/methanol gradient. Fractions were pooled and concentrated to yield yellowish oil (700 mg). The product was verified by NMR.

Preparation of DOPE-Glu-VA: (Z)-(2R)-3-(((2-(5-(((2E,4E,6E,8E)-3,7-dimethyl-9-(2,6,6-trimethylcyclohex-1-en-1-yl)nona-2,4,6,8-tetraen-1-yl)oxy)-5-oxopentanamido)ethoxy)(hydroxy)phosphoryl)oxy)propane-1,2-diyl dioleate

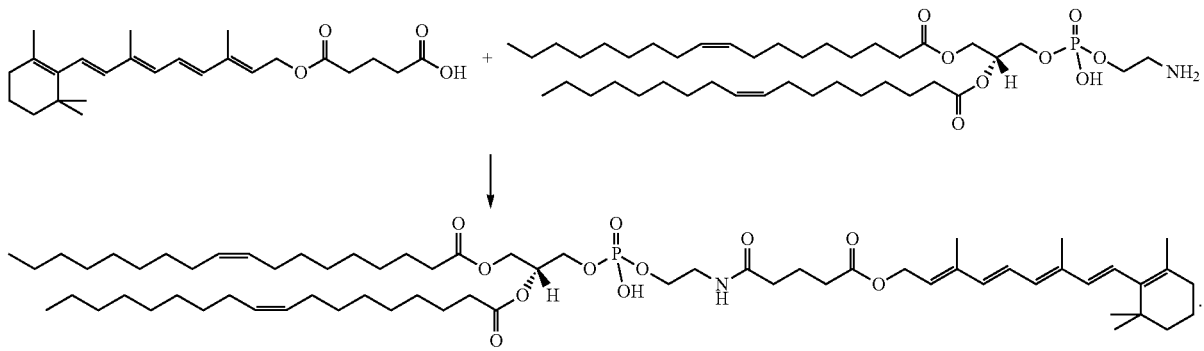

1,2-dioleoyl-sn-glycero-3-phosphoethanolamine (500 mg, 0.672 mmol), N,N,N',N'-Tetramethyl-O-(7-azabenzotriazol-1-yl)uronium hexafluorophosphate (306.5 mg, 0.806 mmol) and 5-(((2E,4E,6E,8E)-3,7-dimethyl-9-(2,6,6-trimethylcyclohex-1-en-1-yl)nona-2,4,6,8-tetraen-1-yl)oxy)-5-oxopentanoic acid (269 mg, 0.672 mmol) was dissolved in chloroform/DMF (10 mL, 1:1 mixture) in an amber-colored vial flushed with argon and N,N-Diisopropylethylamine (300 μL, 1.68 mmol) was added. Reaction mixture was stirred for 12 hours at room temperature. The reaction mixture was concentrated and then purified by silica gel chromatography using a dichloromethane/methanol gradient. The fractions were pooled and concentrated to yield yellowish oil (460 mg, 61%). Verified product by NMR. $^1$H NMR (400 MHz), $\delta_H$: 8.6 (d, 1H), 8.27 (d, 1H), 6.57-6.61 (dd, 1H), 6.08-6.25 (m, 4H), 5.57 (t, 1H), 5.30-5.34 (m, 4H), 5.18 (m, 1H), 4.68-4.70 (d, 2H), 4.28-4.35 (m, 1H), 4.05- 4.15 (m, 1H), 3.81-3.97 (m, 4H), 3.52-3.62 (m, 1H), 3.35-3.45 (m, 2H), 2.95-3.05 (m, 1H), 2.33-2.35 (t, 3H), 2.2-2.3 (m, 7H), 1.9-2.05 (m, 17H), 1.85 (s, 3H), 1.69 (s, 3H), 1.5-1.65 (m, 6H), 1.4-1.5 (m, 2H), 1.18-1.38 (m, ~40H), 1.01 (s, 3H), 0.84-0.88 (m, 12H).

Example 2

DOPE-Glu-NH-VA

Preparation of DOPE-Glu-NH-VA: (Z)-(2R)-3-(((2-(4-((2E,4E,6E,8E)-3,7-dimethyl-9-(2,6,6-trimethylcyclohex-1-en-1-yl)nona-2,4,6,8-tetraenamido)butanamido)ethoxy)(hydroxy)phosphoryl)oxy)propane-1,2-diyl dioleate

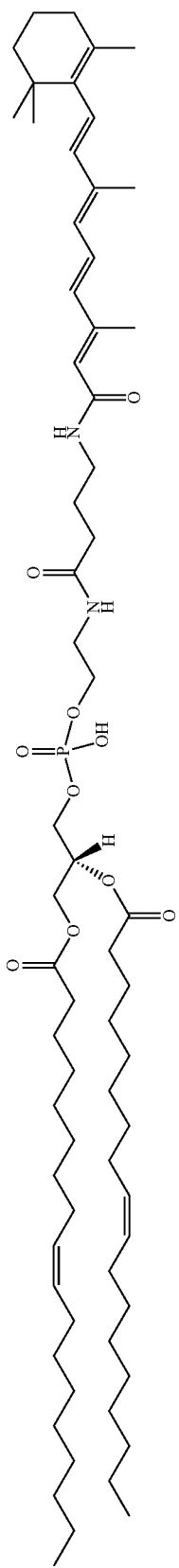

Preparation of Intermediate 1: (Z)-(2R)-3-(((2-(4-aminobutanamido)ethoxy)(hydroxy)phosphoryl)oxy)propane-1,2-diyl dioleate

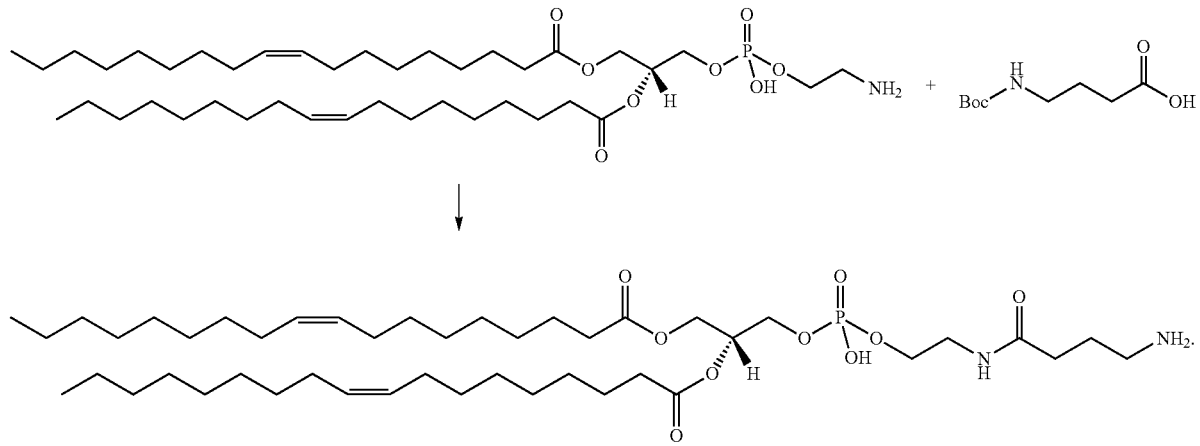

1,2-dioleoyl-sn-glycero-3-phosphoethanolamine (2500 mg, 3.36 mmol), Boc-GABA-OH (751 mg, 3.70 mmol) and N,N,N',N'-tetramethyl-O-(7-azabenzotriazol-1-yl)uronium hexafluorophosphate (1531 mg, 4.03 mmol) were dissolved in a DMF/chloroform (25 mL, 1:1 mixture). N,N-Diisopropylethylamine (880 µL, 5.05 mmol) was added and the mixture was stirred at room temperature for 12 hours under a blanket of argon. The reaction mixture was diluted with ~200 mL H$_2$O and product was extracted with dichloromethane (3×100 ml). The product was washed with ~75 mL pH 4.0 PBS buffered water, dried with sodium sulfate, filtered and concentrated. Material was then purified via silica gel chromatography with a dichloromethane/methanol gradient, and concentrated to yield colorless oil (2.01 g, 64%). The product was verified by NMR. Material was then taken up in 30 mL of 2 M HCl/diethyl ether. Reaction was allowed to stir at room temperature in a water bath. After 2 hours, the solution was concentrated to yield (Z)-(2R)-3-(((2-(4-aminobutanamido)ethoxy)(hydroxy)phosphoryl)oxy)propane-1,2-diyl dioleate.

Preparation of DOPE-Glu-NH-VA: (Z)-(2R)-3-(((2-(4-((2E,4E,6E,8E)-3,7-dimethyl-9-(2,6,6-trimethylcyclohex-1-en-1-yl)nona-2,4,6,8-tetraenamido)butanamido)ethoxy)(hydroxy)phosphoryl)oxy)propane-1,2-diyl dioleate (Z)-(2R)-3-(((2-(4-aminobutanamido)ethoxy)(hydroxy)phosphoryl)oxy)propane-1,2-diyl dioleate (1200 mg, 1.45 mmol), retinoic acid (500 mg, 1.66 mmol) and N,N,N',N'-tetramethyl-0-(7-azabenzotriazol-1-yl)uronium hexafluorophosphate (689 mg, 1.81 mmol) was suspended in DMF/chloroform (10 mL, 1:1 mixture). N,N-Diisopropylethylamine (758 µL, 4.35 mmol) was added. The reaction mixture was flushed with argon, covered with aluminum foil, and stirred at room temperature for 4 hours, then partitioned in dichloromethane (75 mL) and water (75 mL), extracted with dichloromethane, dried (sodium sulfate), filtered and concentrated. Purification by silica gel chromatography using a dichloromethane/methanol gradient yielded (Z)-(2R)-3-(((2-(4-((2E,4E,6E,8E)-3,7-dimethyl-9-(2,6,6-trimethylcyclohex-1-en-1-yl)nona-2,4,6,8-tetraenamido)butanamido)ethoxy)(hydroxy)phosphoryl)oxy)propane-1,2-diyl dioleate (292 mg, 18%). The product was characterized by LCMS and NMR. $^1$H NMR (400 MHz), $\delta_H$: 8.55 (s, 1H), 8.2 (d, 1H), 7.3 (s, 1H), 6.6 (dd, 1H), 6.10-6.27 (m, 5H), 5.5 (t, 1H), 5.31 (s, 4H), 5.1-5.2 (m, 2H), 4.68 (d, 2H), 4.3 (d, 2H), 4.1 (m, 2H), 3.9 (m, 8H), 3.58 (q, 4H), 3.4 (s, 4H), 3.0 (q, 4H), 2.33-2.35 (t, 3H), 2.2-2.3 (m, 7H), 1.9-2.05 (m, 17H), 1.85 (s, 3H), 1.69 (s, 3H), 1.5-1.65 (m, 6H), 1.4-1.5 (m, 2H), 1.18-1.38 (m, ~40H), 1.01 (s, 3H), 0.84-0.88 (m, 12H). MS: m/z 1112.44 (M+H$^+$).

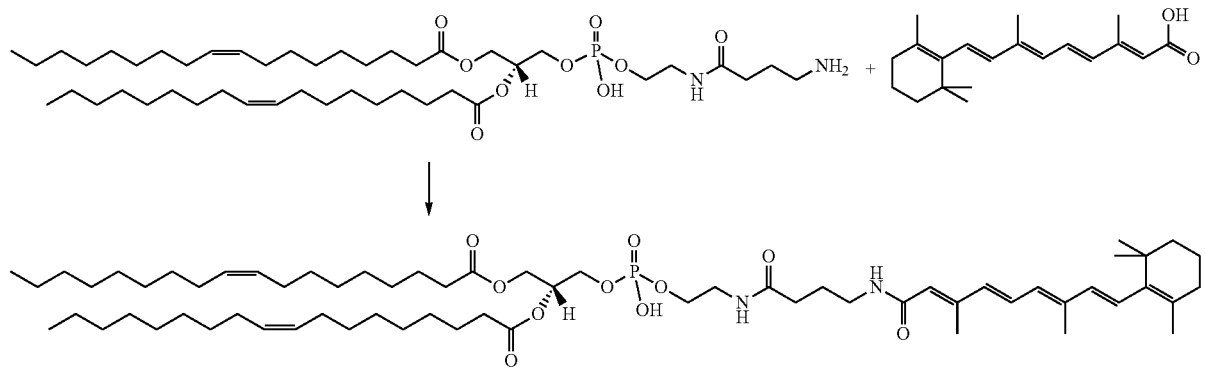 [SMILES: CCCCCCCC/C=C\CCCCCCCC(=O)OC[C@H](COP(=O)(O)OCCNC(=O)CCCN)OC(=O)CCCCCCC/C=C\CCCCCCCC ; CC1=C(/C=C/C(C)=C/C=C/C(C)=C/C(=O)O)C(C)(C)CCC1 ; CCCCCCCC/C=C\CCCCCCCC(=O)OC[C@H](COP(=O)(O)OCCNC(=O)CCCNC(=O)/C=C(C)/C=C/C=C(C)/C=C/C1=C(C)CCCC1(C)C)OC(=O)CCCCCCC/C=C\CCCCCCCC]

Example 3 DSPE-PEG550-VA

Preparation of DSPE-PEG550-VA: (2R)-3-(((((45E,47E,49E,51E)-46,50-dimethyl-4,44-dioxo-52-(2,6,6-trimethylcyclohex-1-en-1-yl)-7,10,13,16,19,22,25,28,31,34,37,40-dodecaoxa-3,43-diazadopentaconta-45,47,49,51-tetraen-1-yl)oxy)(hydroxy)phosphoryl)oxy)propane-1,2-diyl distearate

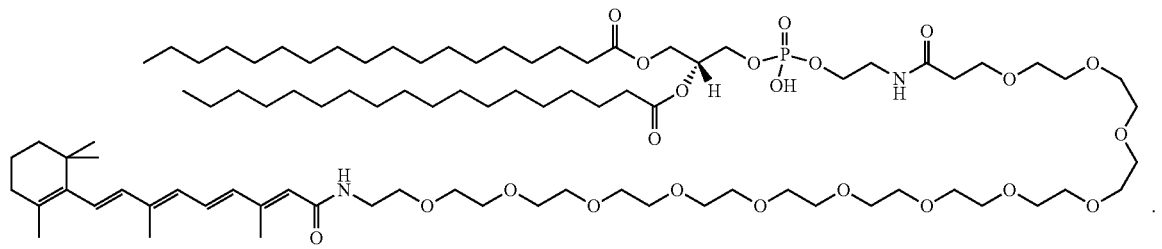 [SMILES: CCCCCCCCCCCCCCCCCC(=O)OC[C@H](COP(=O)(O)OCCNC(=O)CCOCCOCCOCCOCCOCCOCCOCCOCCOCCOCCOCCOCCNC(=O)/C=C(C)/C=C/C=C(C)/C=C/C1=C(C)CCCC1(C)C)OC(=O)CCCCCCCCCCCCCCCCC]

Preparation of Intermediate 1: (2R)-3-((((2,2-dimethyl-4,44-dioxo-3,8,11,14,17,20,23,26,29,32,35,38,41-tridecaoxa-5,45-diazaheptatetracontan-47-yl)oxy)(hydroxy)phosphoryl)oxy)propane-1,2-diyl distearate

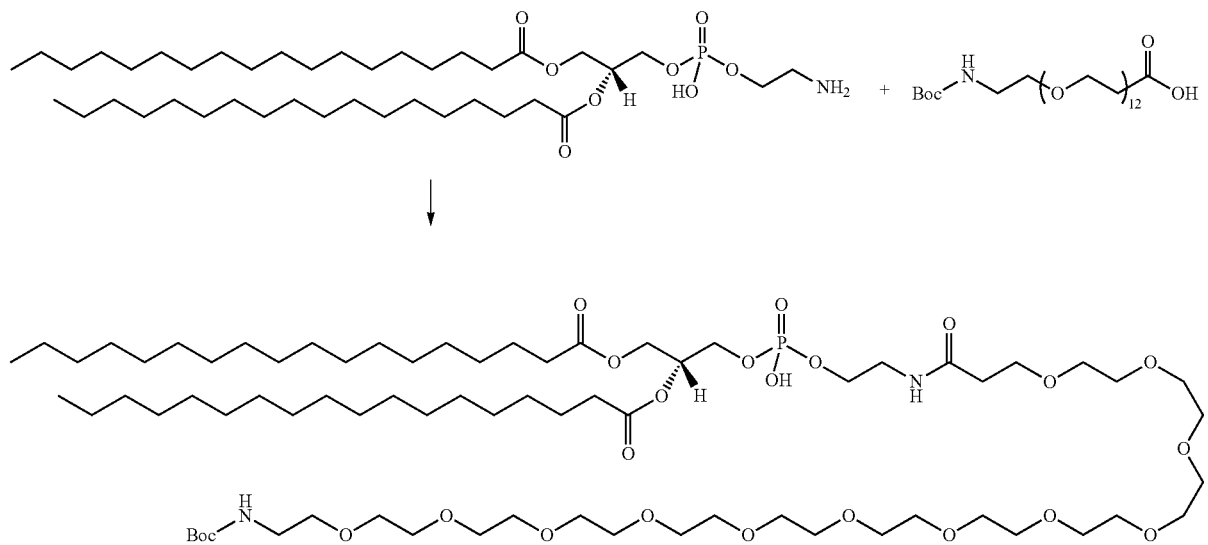

1,2-distearoyl-sn-glycero-3-phosphoethanolamine (200 mg, 0.267 mmol), t-Boc-N-amido-dPEG$_{12}$-acid (211 mg, 0.294 mmol) and N,N,N',N'-tetramethyl-O-(7-azabenzotriazol-1-yl)uronium hexafluorophosphate (122 mg, 0.320 mmol) were dissolved in a chloroform/methanol/H$_2$O (6 mL, 65:35:8) in a 20 mL scintillation vial flushed with argon. N,N-Diisopropylethylamine (116 µL, 0.668 mmol) was added. Reaction was stirred at 25° C. for 4 hours and concentrated. Material was then purified via silica gel chromatography with a dichloromethane/methanol gradient to yield (2R)-3-((((2,2-dimethyl-4,44-dioxo-3,8,11,14,17,20,23,26,29,32,35,38,41-tridecaoxa-5,45-diazaheptatetracontan-47-yl)oxy)(hydroxy)phosphoryl)oxy)propane-1,2-diyl distearate as an oil (252 mg, 65%).

Preparation of DSPE-PEG550-VA: (2R)-3-(((((45E, 47E,49E,51E)-46,50-dimethyl-4,44-dioxo-52-(2,6,6-trimethylcyclohex-1-en-1-yl)-7,10,13,16,19,22,25, 28,31,34,37,40-dodecaoxa-3,43-diazadopentaconta-45,47,49,51-tetraen-1-yl)oxy)(hydroxy)phosphoryl) oxy)propane-1,2-diyl distearate concentrated. Material was then purified via silica gel chromatography with a dichloromethane/methanol gradient to yield (2R)-3-(((((45E,47E,49E,51E)-46,50-dimethyl-4,44-dioxo-52-(2,6,6-trimethylcyclohex-1-en-1-yl)-7,10,13,16, 19,22,25,28,31,34,37,40-dodecaoxa-3,43-diazadopenta-conta-45,47,49,51-tetraen-1-yl)oxy)(hydroxy)phosphoryl)

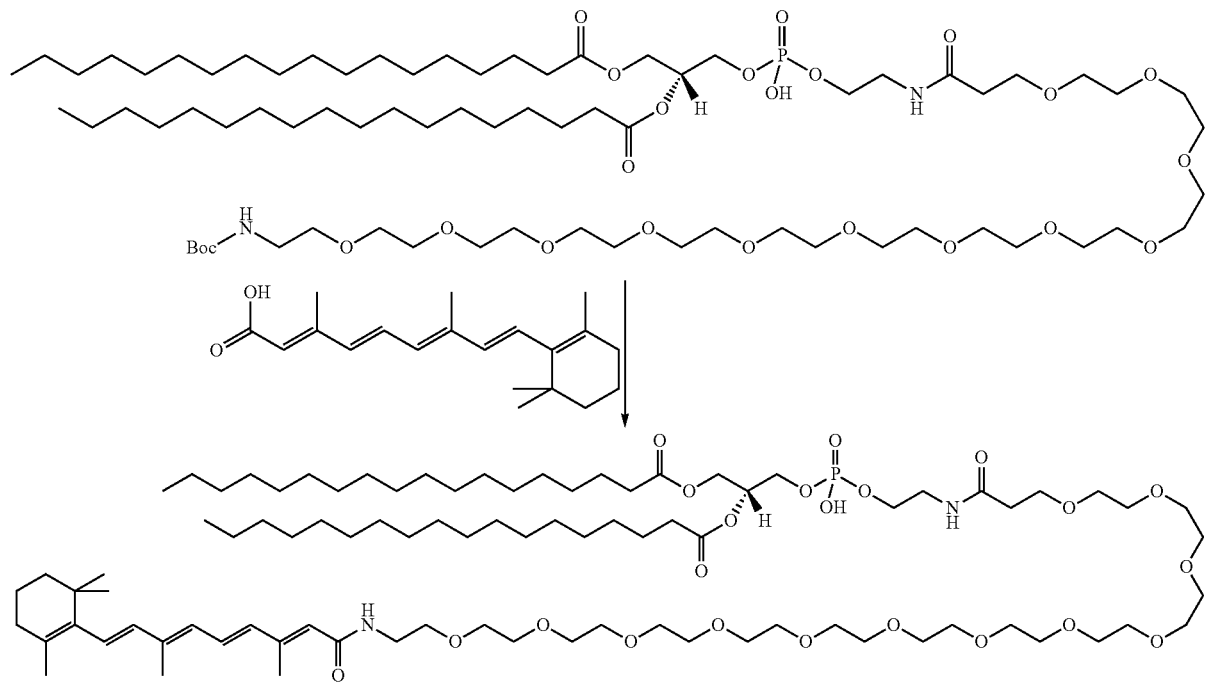

(2R)-3-((((2,2-dimethyl-4,44-dioxo-3,8,11,14,17,20,23,26, 29,32,35,38,41-tridecaoxa-5,45-diazaheptatetracontan-47-yl)oxy)(hydroxy)phosphoryl)oxy)propane-1,2-diyl distearate (252 mg, 0.174 mmol) was dissolved in diethyl ether (5 mL). Reaction was placed in a water bath at room temperature. 2 M HCl/diethyl ether (2 mL, 4 mmol) was added and the mixture was stirred for 1 hour. Afterwards, solvent and excess HCl were removed in vacuo. Suspended material in 2 mL N,N-Dimethylformamide in a flask flushed with argon. Retinoic acid (57.5 mg, 0.191 mmol), N,N,N',N'-tetramethyl-O-(7-azabenzotriazol-1-yl)uronium hexafluorophosphate (79 mg, 0.209 mmol) and N,N-Diisopropylethylamine (106 μL, 0.609 mmol) were added. More chloroform/methanol/$H_2O$ was added (1 mL, 65:35:8 v:v:v mixture) to dissolve the reactants. After 3.5 hours, the reaction mixture was oxy)propane-1,2-diyl distearate as a tan solid (210 mg, 74%). Verified product by NMR and LCMS. $^1$H NMR (400 MHz), $\delta_H$: 8.6 (s, 1H), 8.25 (d, 1H), 6.8-6.9 (dd, 1H), 6.3-6.4 (m, 1H), 6.12-6.25 (dd, 5H), 5.71 (s, 1H), 5.18 (m, 2H), 4.33 (dd, 2H), 4.13 (m, 2H), 3.95 (m, 2H), 3.74 (m, 8H), 3.63 (s, ~48H), 3.0 (q, 2H), 2.5 (t, 3H), 2.35 (s, 3H), 2.25 (t, 8H), 1.97 (m, 7H), 1.7 (3, 3H), 1.5 (m, 2H), 1.36 (m, 12H), 1.23 (m, ~56H), 1.01 (s, 6H), 0.86 (t, 12H). MS: m/z 1630.28 (M+H$^+$).

Example 4 DSPE-PEG2000-Glu-VA

Preparation of DSPE-PEG2000-Glu-VA

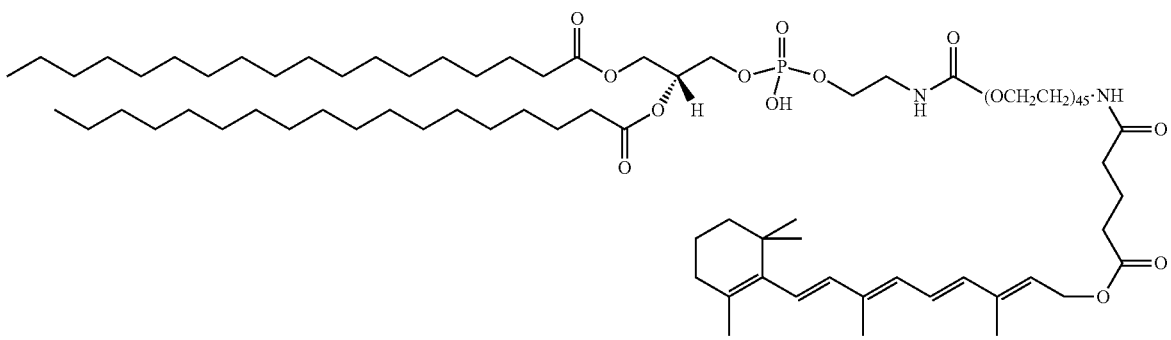

Preparation of Intermediate 1: 5-(((2E,4E,6E,8E)-3,7-dimethyl-9-(2,6,6-trimethylcyclohex-1-en-1-yl)nona-2,4,6,8-tetraen-1-yl)oxy)-5-oxopentanoic acid

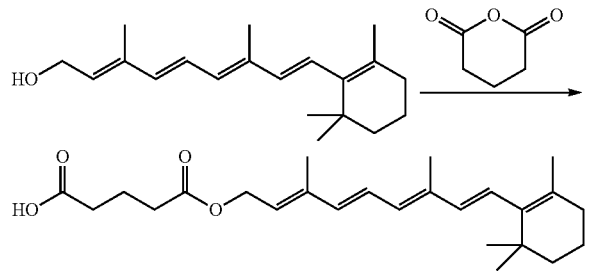

Glutaric anhydride (115 mg, 1.01 mmol) and retinol (240 mg, 0.838 mmol) were dissolved in dichloromethane (3 mL) in an amber-colored vial. Triethylamine (257 ul, 1.84 mmol) was added and the vial was flushed with argon. Reaction was stirred at room temperature for 12 hours. The reaction mixture was concentrated and then purified via silica gel chromatography with a dichloromethane/methanol gradient to yield 5-(((2E,4E,6E,8E)-3,7-dimethyl-9-(2,6,6-trimethylcyclohex-1-en-1-yl)nona-2,4,6,8-tetraen-1-yl)oxy)-5-oxopentanoic acid as a yellowish oil (700 mg, 78%). Material characterized by NMR.

Preparation of DSPE-PEG2000-Glu-VA 5-(((2E,4E,6E,8E)-3,7-dimethyl-9-(2,6,6-trimethylcyclohex-1-en-1-yl)nona-2,4,6,8-tetraen-1-yl)oxy)-5-oxopentanoic acid (43 mg, 0.108 mmol), DSPE-PEG2000-NH$_2$ (250 mg, 0.090 mmol) and N,N,N',N'-tetramethyl-O-(7-azabenzotriazol-1-yl)uronium hexafluorophosphate (45 mg, 0.117 mmol) were dissolved in N,N-dimethylformamide (2 mL) in an amber-colored scintillation vial flushed with argon gas. N,N-diisopropylethylamine (47 µL, 0.270 mmol) was added and the reaction stirred for 12 hours at room temperature, then purified via silica gel chromatography with a dichloromethane/methanol gradient to yield yellowish oil (59 mg, 20.7%). Verified product by NMR. $^1$H NMR (400 MHz), $\delta_H$: 706 (m, 1H), 6.59-6.66 (dd, 1H), 6.06-6.30 (m 5H), 5.56-5.60 (t, 1H), 5.17-5.23 (m, 2H), 4.35-4.42 (dd, 2H), 4.12-4.25 (m, 5H), 3.96-3.97 (m, 6H), 3.79-3.81 (t, 1H), 3.66 (m, ~180H), 3.51-3.58 (m, 2H), 3.4-3.48 (m, 4H), 3.3-3.38 (m, 2H), 2.25-2.45 (m, 14H), 1.5-2.0 (m, 15H), 1.23-1.32 (m, ~56H), 1.01 (s, 3H), 0.85-0.88 (t, 12H).

Example 5 DOPE-Gly$_3$-VA

Preparation of DOPE-Gly$_3$-VA: (Z)-(2R)-3-(((((14E,16E,18E,20E)-15,19-dimethyl-4,7,10,13-tetraoxo-21-(2,6,6-trimethylcyclohex-1-en-1-yl)-3,6,9,12-tetraazahenicosa-14,16,18,20-tetraen-1-yl)oxy)(hydroxy)phosphoryl)oxy)propane-1,2-diyl dioleate

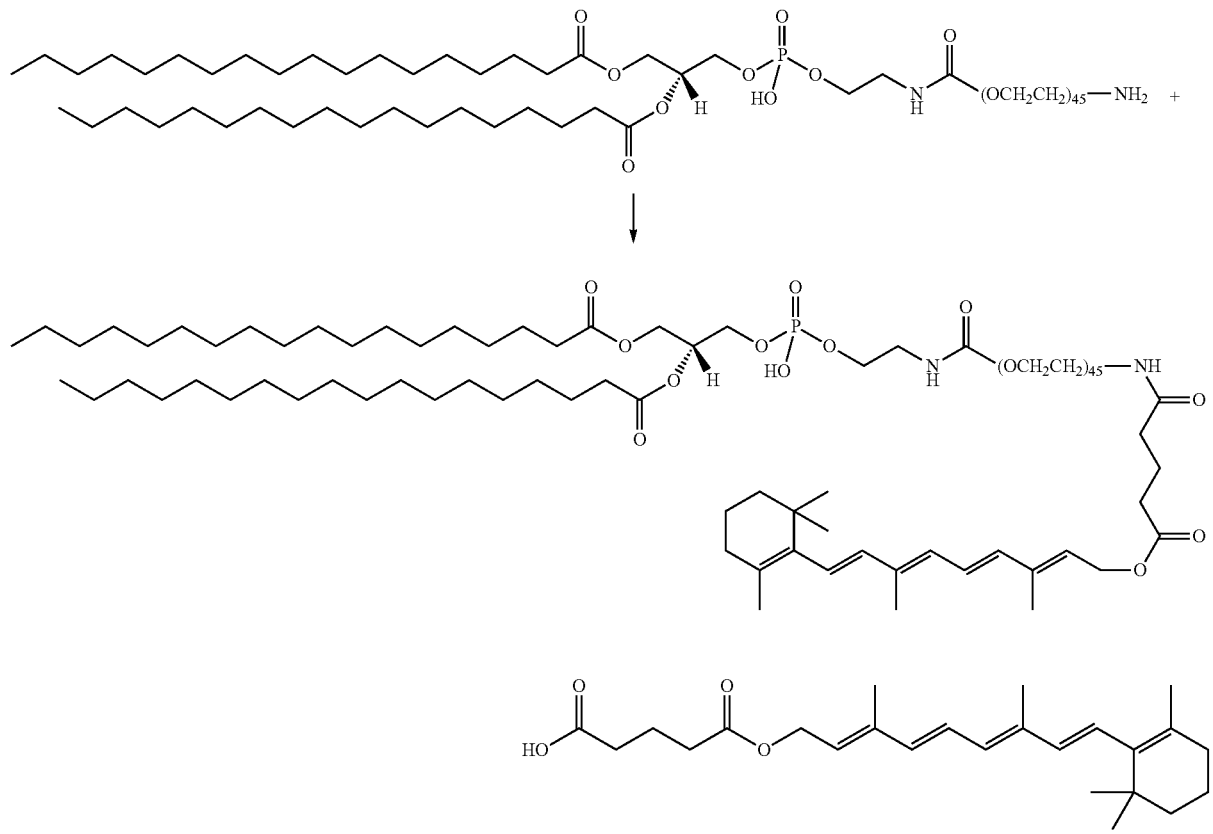

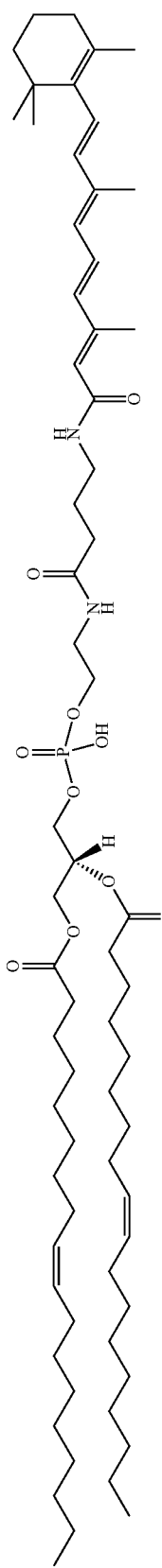

Preparation of Intermediate 1: (Z)-(2R)-3-(((2-(2-(2-(2-aminoacetamido)acetamido)acetamido)ethoxy)(hydroxy)phosphoryl)oxy)propane-1,2-diyl dioleate

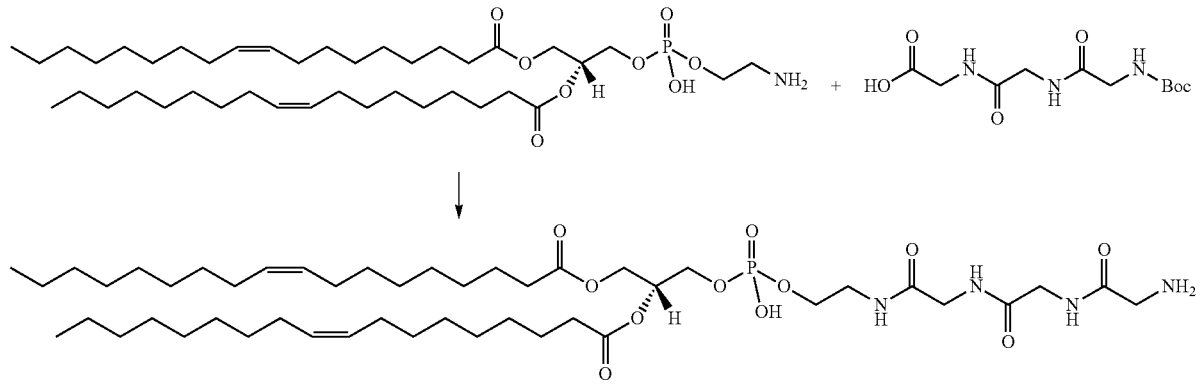

Boc-Gly-Gly-Gly-OH (382 mg, 1.34 mmol) and N,N,N',N'-tetramethyl-O-(7-azabenzotriazol-1-yl)uronium hexafluorophosphate (532 mg, 1.4 mmol) were dissolved in DMF (5 mL). N,N-Diisopropylethylamine (488 μL, 2.8 mmol) was added and the mixture was allowed to stir at room temperature for 10-15 minutes. Afterwards, a solution of 1,2-dioleoyl-sn-glycero-3-phosphoethanolamine (833 mg, 1.12 mmol) in chloroform (5 mL) was added and the reaction vessel was flushed with argon. After 16 hours at room temperature, the reaction mixture was concentrated and partitioned between dichloromethane (50 mL) and water (50 mL), extracted with dichloromethane (3×50 mL), dried with sodium sulfate, filtered and concentrated. Material was purified via silica gel chromatography using a dichloromethane/methanol gradient to yield colorless oil residue. To this, 2 M HCl/diethyl ether (5 mL) was added and the reaction mixture was allowed to stir in a water bath for approximately 2 hours. The reaction mixture was concentrated and the residue was taken up in dichloromethane (75 mL), washed with saturated sodium bicarbonate solution (75 mL), extracted product with dichloromethane (3×75 mL), dried with sodium sulfate, filtered and concentrated to yield (Z)-(2R)-3-(((2-(2-(2-(2-aminoacetamido)acet-amido)ethoxy)(hydroxy)phosphoryl)oxy)propane-1,2-diyl dioleate as a semi-solid (765 mg, 90%). Verified by NMR.

Preparation of DOPE-Gly$_3$-VA: (Z)-(2R)-3-(((((14E,16E,18E,20E)-15,19-dimethyl-4,7,10,13-tetraoxo-21-(2,6,6-trimethylcyclohex-1-en-1-yl)-3,6,9,12-tetraazahenicosa-14,16,18,20-tetraen-1-yl)oxy)(hydroxy)phosphoryl)oxy)propane-1,2-diyl dioleate

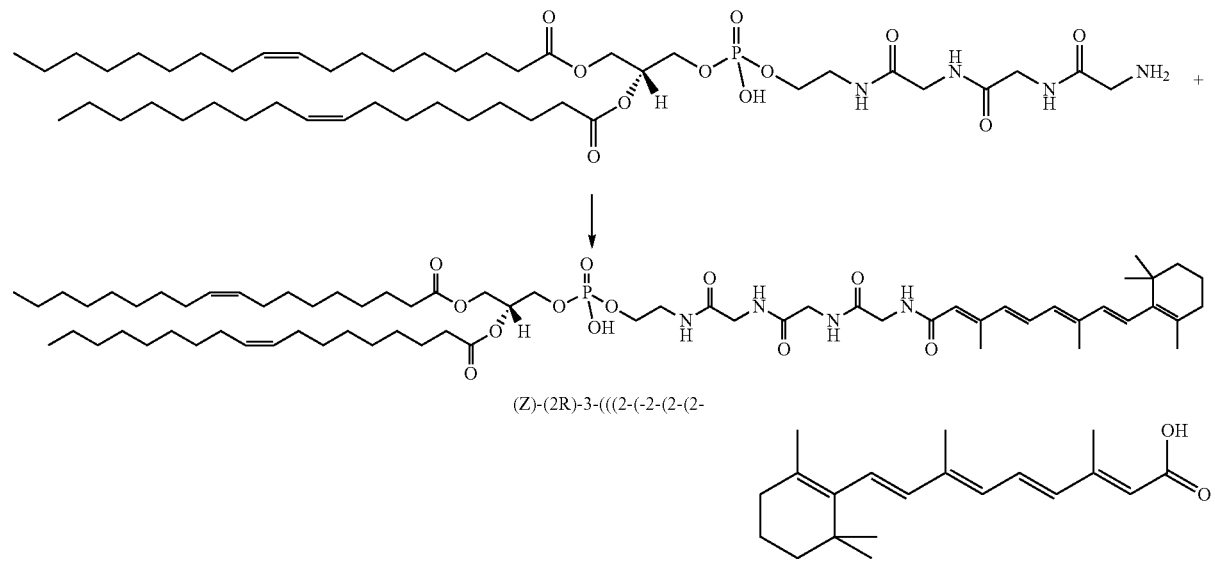

(Z)-(2R)-3-(((2-(-2-(2-(2-aminoacetamido)acetamido)acetamido)ethoxy)(hydroxy)phosphoryl)oxy)propane-1,2-diyl dioleate (765 mg, 0.836 mmol), retinoic acid (301 mg, 1.00 mmol), and N,N,N',N'-tetramethyl-0-(7-azabenzotriazol-1-yl)uronium hexafluorophosphate (413 mg, 1.09 mmol) were suspended in N,N-Dimethylformamide (5 mL). N,N-Diisopropylethylamine (437 μL, 2.51 mmol) was added and the reaction vessel was flushed with argon gas. Added chloroform (5 mL) to aid in the solvation of materials. Reaction was stirred for ~4 hours at room temperature in a round bottom flask covered with aluminum foil. Partitioned material between water (100 mL) and dichloromethane (100 mL). Extracted with dichloromethane (3×100 mL), dried with sodium sulfate, filtered and concentrated. Material was then purified via silica gel chromatography using a dichloromethane/methanol gradient to yield (Z)-(2R)-3-(((((14E,16E,18E,20E)-15,19-dimethyl-4,7,10,13-tetraoxo-21-(2,6,6-trimethylcyclohex-1-en-1-yl)-3,6,9,12-tetraazahenicosa-14,16,18,20-tetraen-1-yl)oxy)(hydroxy)phosphoryl)oxy)propane-1,2-diyl dioleate as an orange oil (704 mg, 70%). Verified product by LCMS and NMR. $^1$H NMR (400 MHz), $\delta_H$: 6.90 (t, 1H), 6.21 (q, 2H), 6.08-6.12 (d, 2H), 5.83 (s, 1H), 5.31 (s, 4H), 5.30 (s, 2H), 4.37 (d, 1H), 4.15 (m, 1H), 3.91 (m, 8H), 3.59 (m, 2H), 3.29 (m, 2H), 3.01 (m, 2H), 2.28 (m, 6H), 1.95-1.98 (m, 12H), 1.44 (s, 3H), 1.5-1.6 (m, 2H), 1.44 (m, 6H), 1.24 (m, ~48H), 1.00 (s, 6H), 0.86 (t, 3H). MS: m/z 1198.42 (M+H$^+$).

Example 6 VA-PEG-VA

Preparation of VA-PEG-VA: N1,N19-bis(((16E,18E,20E,22E)-17,21-dimethyl-15-oxo-23-(2,6,6-trimethylcyclohex-1-en-1-yl)-4,7,10-trioxa-14-azatricosa-16,18,20,22-tetraen-1-yl)-4,7,10,13,16-pentaoxanonadecane-1,19-diamide

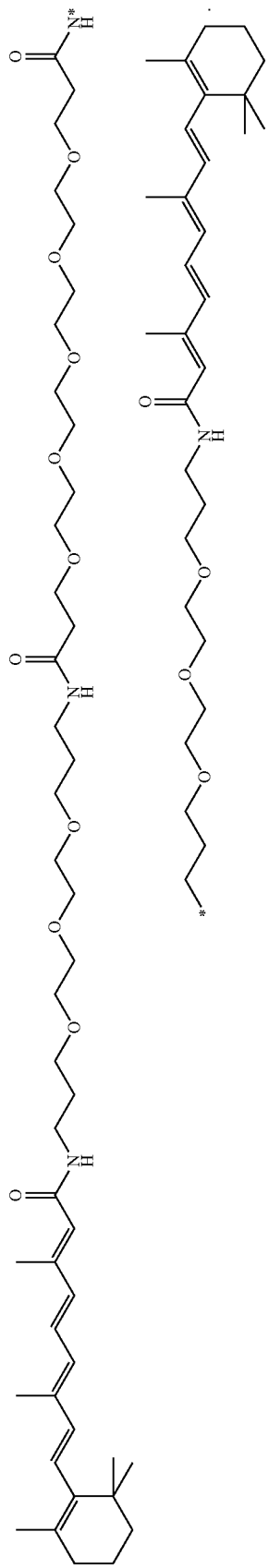

Preparation of VA-PEG-VA: N1,N19-bis((16E,18E,20E,22E)-17,21-dimethyl-15-oxo-23-(2,6,6-trimethylcyclohex-1-en-1-yl)-4,7,10-trioxa-14-azatricosa-16,18,20,22-tetraen-1-yl)-4,7,10,13,16-pentaoxanonadecane-1,19-diamide

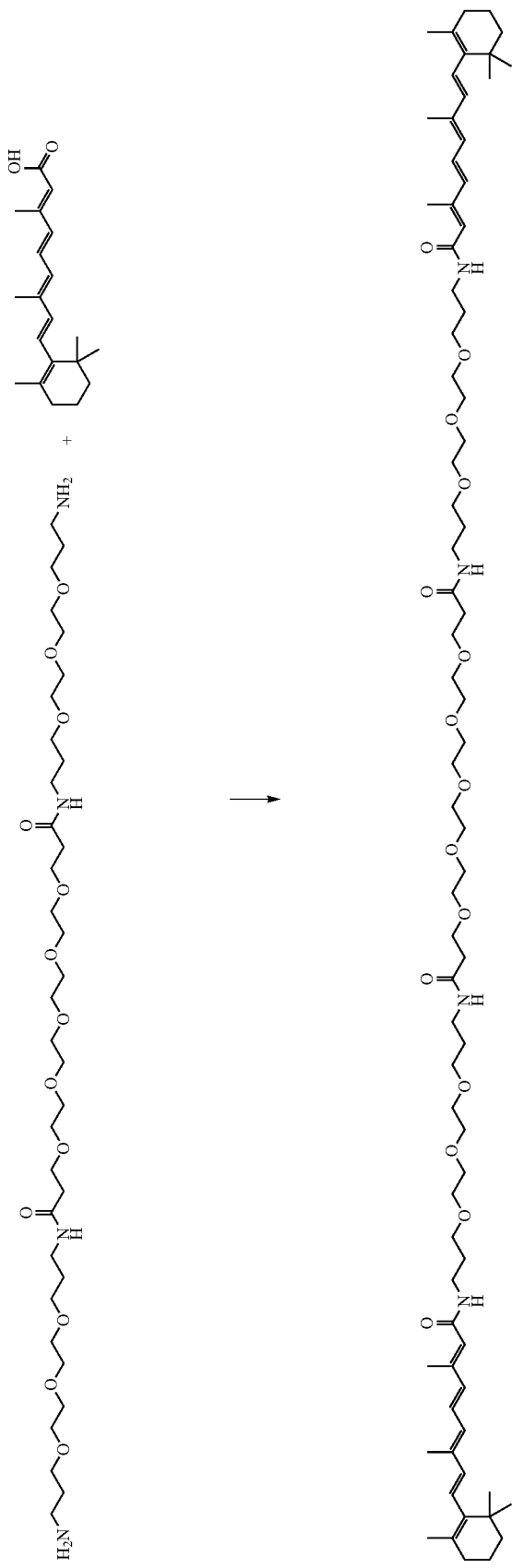

Retinoic acid (2913 mg, 9.70 mmol), N,N,N',N'-tetramethyl-O-(7-azabenzotriazol-1-yl)uronium hexafluorophosphate (3992 mg, 10.50 mmol) and diamido-dPEG$_{11}$-diamine (3000 mg, 4.04 mmol) were suspended in N,N-dimethylformamide (10 mL). N,N-Diisopropylethylamine (4222 µL, 24.24 mmol) was added and the vessel was flushed with argon. Reaction was stirred at room temperature 12 hours in a round bottom flask covered with aluminum foil. Partitioned material between ethyl acetate (125 mL) and water (125 mL). Extracted with ethyl acetate (3×125 mL), dried with sodium sulfate, filtered and concentrated. Material was then purified via silica gel chromatography with a dichloromethane/methanol gradient. Pooled fractions and concentrated to yield yellow oil (2900 mg, 54.9%). Verified product by LCMS and NMR. $^1$H NMR (400 MHz), $\delta_H$: 7.1 (s, 2H), 6.87 (t, 2H), 6.51 (t, 2H), 6.12-6.20 (dd, 8H), 5.66 (s, 2H), 3.6-3.8 (m, ~44H), 3.4 (q, 4H), 3.3 (q, 4H), 2.46 (t, 4H), 2.32 (s, 6H), 1.9-2.05 (m, 10H), 1.7-1.85 (m, 15H), 1.6 (m, 4H), 1.3-1.5 (m, 6H), 1.01 (s, 12H). QTOF MS: m/z 1306 (M+H$^+$).

Example 7 VA-PEG2000-VA

Preparation of (2E,2'E,4E,4'E,6E,6'E,8E,8'E)-N,N'-(3,6,9,12,15,18,21,24,27,30,33,36,39,42,45,48,51,54, 57,60,63,66,69,72,75,78,81,84,87,90,93,96,99,102, 105,108,111,114,117,120,123,126,129,132,135,138-hexatetracontaoxatetracontahectane-1,140-diyl)bis(3, 7-dimethyl-9-(2,6,6-trimethylcyclohex-1-en-1-yl) nona-2,4,6,8-tetraenamide) (VA-PEG2000-VA)

Retinoic acid (109 mg, 0.362 mmol), N,N,N',N'-tetramethyl-O-(7-azabenzotriazol-1-yl)uronium hexafluorophosphate (149 mg, 0.392 mmol) and amine-PEG$_{2K}$-amine (333 mg, 0.151 mmol) were suspended in N,N-Dimethylformamide (3 mL). N,N-Diisopropylethylamine (158 µL, 0.906 mmol) was added and the vessel was flushed with argon. Reaction was allowed to stir at room temperature for 12 hours in a round bottom flask covered with aluminum foil. Partitioned material between ethyl acetate (30 mL) and water (30 mL). Extracted with ethyl acetate (3×30 mL), dried with sodium sulfate, filtered and concentrated. Material was then purified via silica gel chromatography with a dichloromethane/methanol gradient. Pooled fractions and concentrated to yield (2E,2'E,4E,4'E,6E,6'E,8E,8'E)-N,N'-(3,6,9,12,15,18,21,24,27,30,33,36,39,42,45,48,51,54,57,60, 63,66,69,72,75,78,81,84,87,90,93,96,99,102,105,108,111, 114,117,120,123,126,129,132,135,138-hexatetracontaoxatetracontahectane-1,140-diyl)bis(3,7-dimethyl-9-(2,6,6-trimethylcyclohex-1-en-1-yl)nona-2,4,6, 8-tetraenamide) as a yellow oil (97 mg, 23%). Verified product by LCMS and NMR. $^1$H NMR (400 MHz), $\delta_H$: 6.85-6.92 (t, 2h), 6.20-6.32 (M, 6H), 6.08-6.12 (d, 4H), 5.72 (s, 2H), 3.55-3.70 (m, ~180H), 3.4-3.5 (m, 4H), 2.79 (m, 4H), 2.78 (s, 6H), 2.33 (s, 6H), 2.05 (m, 4H), 1.97 (s, 6H), 1.80 (m, 2H), 1.79 (s, 6H), 1.69 (s, 6H), 1.60 (m, 4H), 1.45 (m, 4H), 1.01 (s, 12H). QTOF MS: m/z 2651 (M+H$^+$).

Example 8 DSPE-PEG2000-VA

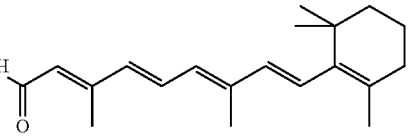

Preparation of VA-PEG2000-VA: (2E,2'E,4E,4'E, 6E,6'E,8E,8'E)-N,N'-(3,6,9,12,15,18,21,24,27,30,33, 36,39,42,45,48,51,54,57,60,63,66,69,72,75,78,81,84, 87,90,93,96,99,102,105,108,111,114,117,120,123, 126,129,132,135,138-hexatetracontaoxatetracontahectane-1,140-diyl)bis(3, 7-dimethyl-9-(2,6,6-trimethylcyclohex-1-en-1-yl) nona-2,4,6,8-tetraenamide)

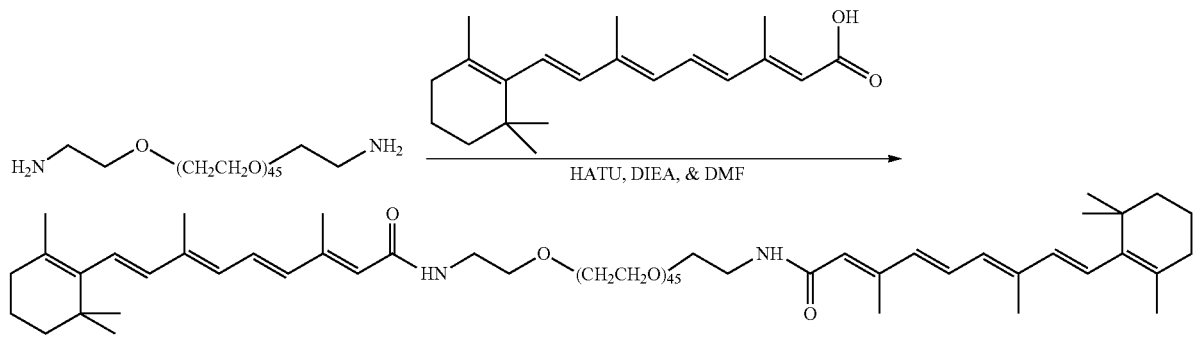

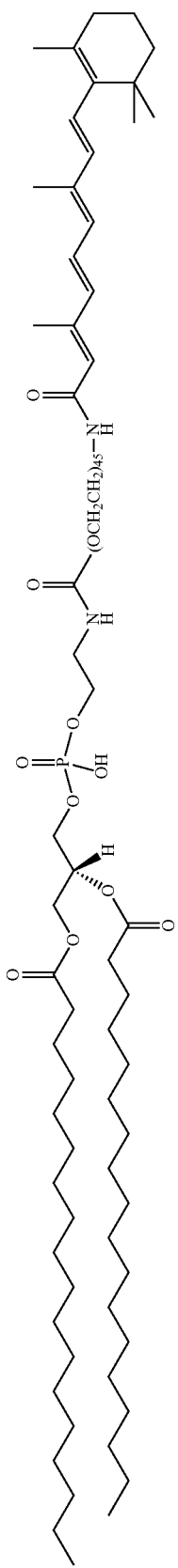

Preparation of DSPE-PEG2000-VA

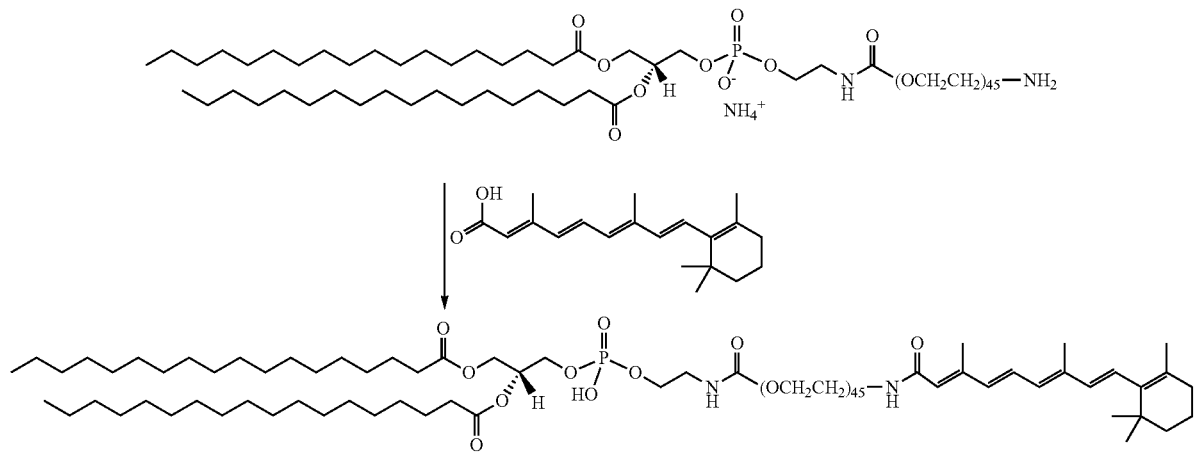

DSPE-PEG2000-NH$_2$ (250 mg, 0.090 mmol), retinoic acid (3.3 mg, 0.108 mmol) and N,N,N',N'-Tetramethyl-O-(7-azabenzotriazol-1-yl)uronium hexafluorophosphate (45 mg, 0.117 mmol) were dissolved in N,N-Dimethylformamide. N,N-Diisopropylethylamine (47 µL, 0.270 mmol) was added to the mixture. The amber colored scintillation vial was flushed with argon and allowed to stir 3 days at room temperature. Material was then purified silica gel chromatography using a dichloromethane/methanol gradient. Pooled fractions and concentrated to yield DSPE-PEG2000-VA as a yellow oil (245 mg, 89%). Verified product by NMR. $^1$H NMR (400 MHz), $\delta_H$: 6.86 (dd, 1H), 6.25 (m, 1H), 6.09-6.21 (dd, 4H), 5.71 (s, 1H), 5.1-5.2 (m, 1H), 4.3-4.4 (d, 1H), 4.1-4.2 (m, 3H), 3.85-4.0 (m, 4H), 3.8 (t, 1H), 3.5-3.75 (m, ~180H), 3.4-3.5 (m, 8H), 3.3 (m, 2H), 2.35 (s, 3H), 2.26 (m, 4H), 1.70 (s, 3H), 1.55-1.65 (m, 6H), 1.47 (m, 2H), 1.23 (s, ~60H), 1.01 (s, 6H), 0.85 (t, 6H).

Example 9 diVA-PEG-diVA, Referred to Herein as "DiVA"

Preparation of DiVA: N1,N19-bis((S,23E,25E,27E,29E)-16-((2E,4E,6E,8E)-3,7-dimethyl-9-(2,6,6-trimethylcyclo-hex-1-en-1-yl)nona-2,4,6,8-tetraenamido)-24,28-dimethyl-15,22-dioxo-30-(2,6,6-trimethylcyclohex-1-en-1-yl)-4,7,10-trioxa-14,21-diazatriaconta-23,25,27,29-tetraen-1-yl)-4,7,10,13,16-pentaoxanonadecane-1,19-diamide

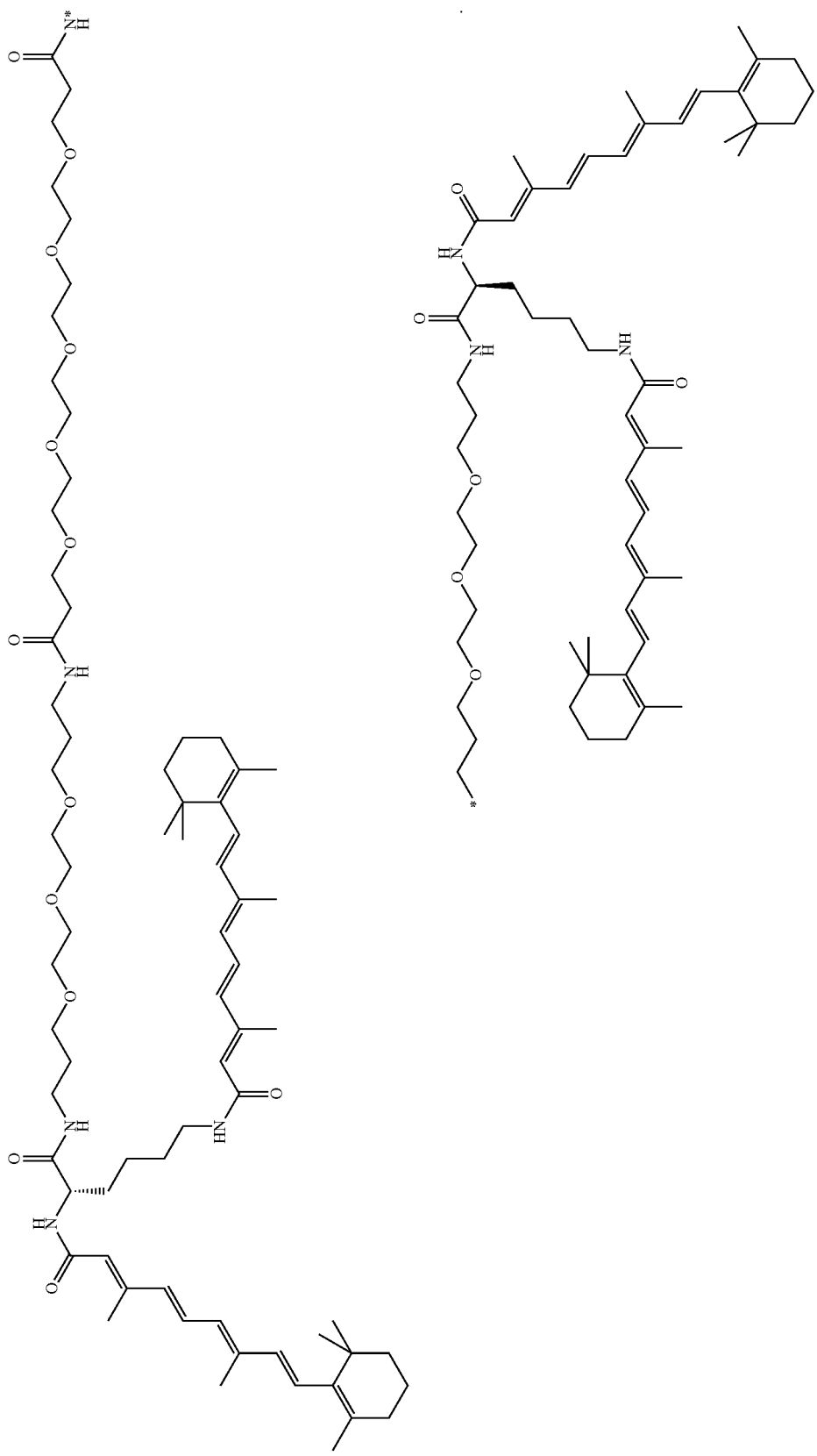

Preparation of Intermediate 1: tetrabenzyl ((5S,57S)-6,22,40,56-tetraoxo-11,14,17,25,28,31,34,37,45,48,51-undecaoxa-7,21,41,55-tetraazahenhexacontane-1,5,57,61-tetrayl) tetracarbamate, Z-DiVA-PEG-DiVA-IN 5

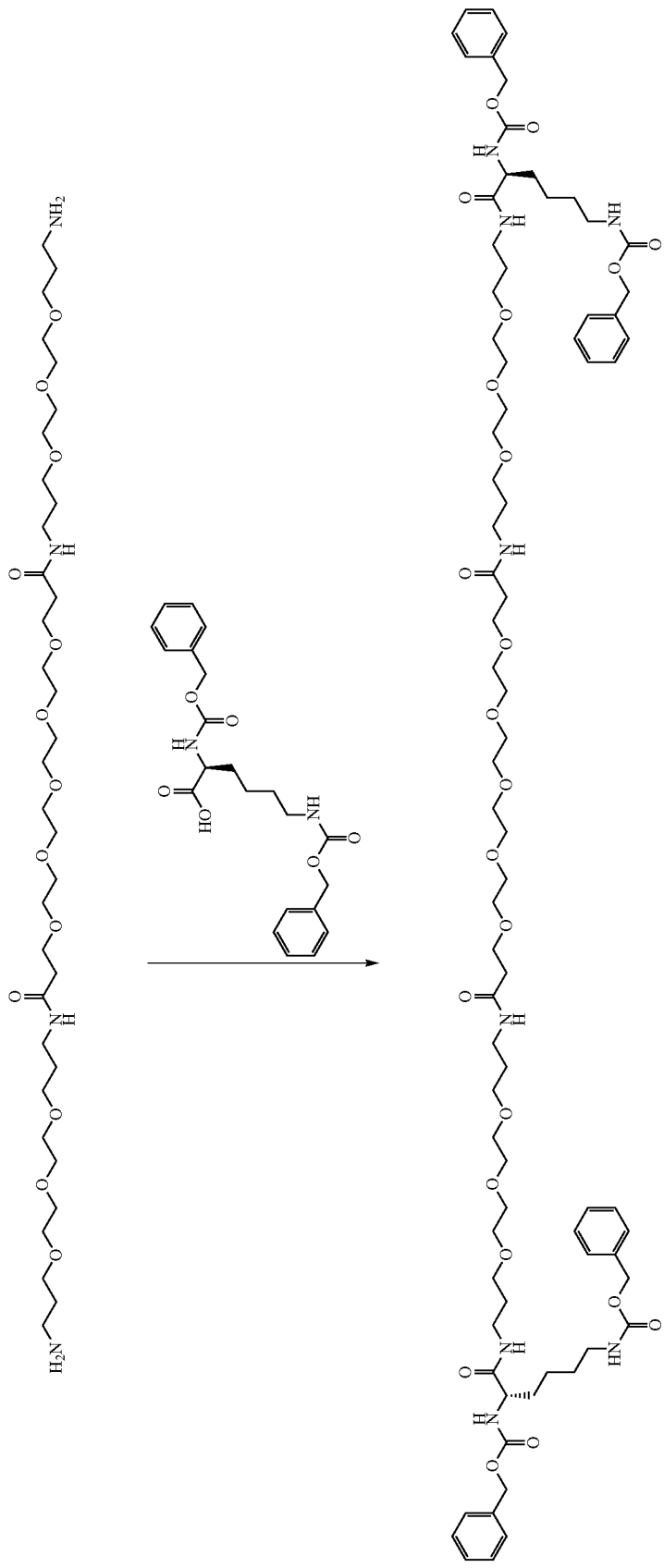

A 1 L reaction flask cooled to 5-10° C. was purged with nitrogen and charged with dichloromethane (300 mL), d-PEG-11-diamine (Quanta lot EK1-A-1100-010, 50.0 g, 0.067 mol), Z-(L)-Lys(Z)—OH (61.5 g, 0.15 mol), and HOBt hydrate (22.5 g, 0.15 mol). 4-Methylmorpholine (4-MMP) (15.0 g, 0.15 mol) was added to the suspension and a light exothermic reaction was observed. A suspension of EDC hydrochloride (43.5 g, 0.23 mol) and 4-MMP (20.0 g, 0.20 mol) in dichloromethane (150 mL) was added over a period of 30 minutes, and moderate cooling was required in order to maintain a temperature of 20-23° C. The slightly turbid solution was stirred for 12 hours at ambient temperature, and HPLC indicates completion of reaction. Deionized water (300 mL) was added and after having stirred for 10 minutes, a quick phase separation was observed. The aqueous phase was extracted with dichloromethane (150 mL)—with a somewhat slower phase separation. The combined organic extracts are washed with 6% sodium bicarbonate (300 mL) and dried with magnesium sulphate (24 g). Evaporation from a 40-45° C. water bath under reduced pressure gives 132 g of crude product. A solution of crude product (131 g) in 8% methanol in ethyl acetate in loaded onto a column of silica gel 60 (40-63μ), packed with 8% methanol in ethyl acetate. The column was eluted with 8% methanol in ethyl acetate (7.5 L). The fractions containing sufficiently pure product (5.00-7.25 L) was evaporated from a 45° C. water bath under reduced pressure and 83.6 g of purified product. A solution of purified product (83.6 g) in dichloromethane (200 mL) was loaded onto a column of DOWEX® 650 C ($H^+$) (200 g), which has been washed with dichloromethane (250 mL). The column was eluted with dichloromethane (200 mL). The combined product containing fractions (300-400 mL) were dried with magnesium sulphate (14 g) and evaporated from a 45° C. water bath under reduced pressure to yield tetrabenzyl ((5S,57S)-6,22,40,56-tetraoxo-11,14,17,25,28,31,34,37,45,48,51-undecaoxa-7,21,41,55-tetraazahenhexacontane-1,5,57,61-tetrayl)tetracarbamate, referred to herein as Z-DiVA-PEG-DiVA-IN (77.9 g, HPLC purity 94.1%).

Preparation of Intermediate 2: N1,N19-bis((S)-16,20-diamino-15-oxo-4,7,10-trioxa-14-azaicosyl)-4,7,10,13,16-pentaoxanonadecane-1,19-diamide, referred to herein as DiVA-PEG-DiVA-IN

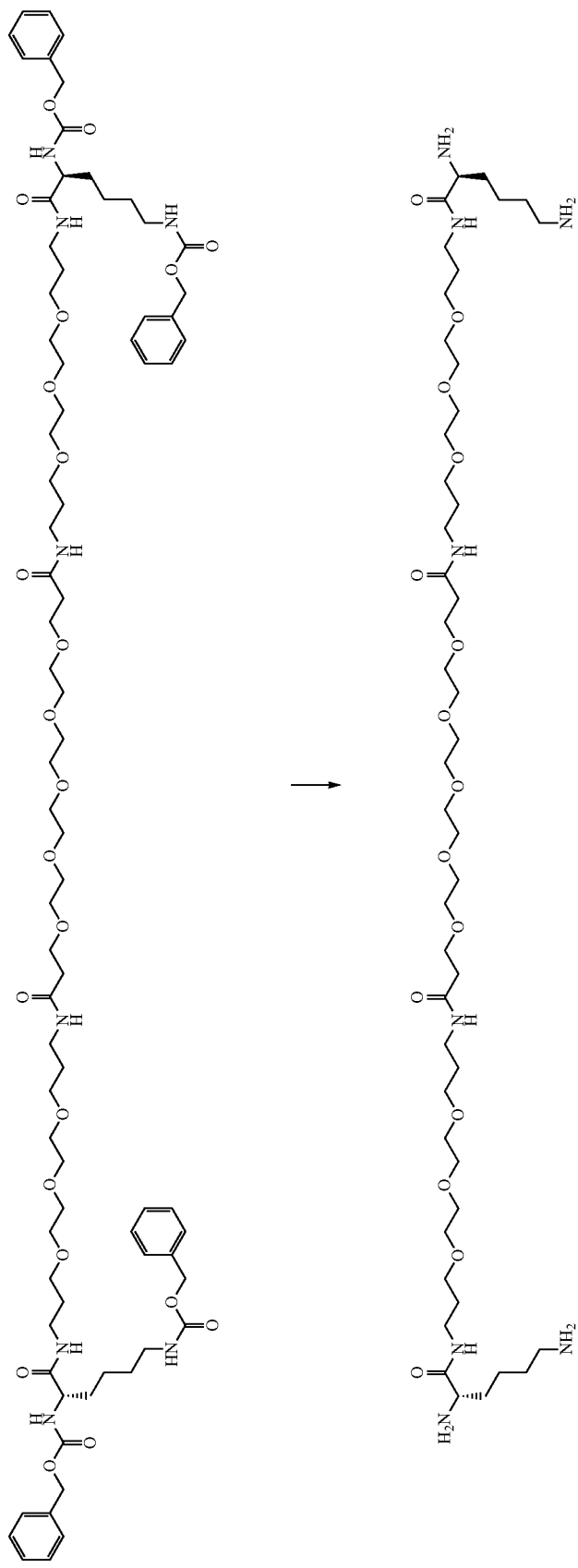

A 1 L reaction flask was purged with nitrogen and charged with methanol (600 mL) and Z-DiVA-PEG-DiVA-IN (92.9, 60.5 mmol). The mixture was stirred under nitrogen until a solution was obtained. The catalyst, 10% Pd/C/50% water (Aldrich, 10 g) was added. The mixture was evacuated, and then the pressure was equalized by nitrogen. The mixture was evacuated, and then the pressure was equalized by hydrogen. Ensuring a steady, low flow of hydrogen over the reaction mixture, the stirrer was started. Hydrogenation was continued in a flow of hydrogen for one hour. The system was then closed, and hydrogenation was continued at ~0.1 bar for one hour. The mixture was evacuated and then re-pressurized to ~0.1 bar with hydrogen. After another hour of hydrogenation, the mixture was evacuated and then re-pressurized to 0.1 bar with hydrogen. Stirring under hydrogen was continued for 15 hours after which time no starting material could be detected by HPLC. The mixture was evacuated, and then the pressure was equalized by nitrogen. The mixture was evacuated, and then the pressure was equalized by nitrogen. The reaction mixture was then filtered on a pad of CELITE® 545. The filter cake was washed with methanol (100 mL). The combined filtrate was concentrated, finally at 45° C. and at a pressure of less than 50 mbar. Toluene (100 mL) was added and the resulting mixture was again concentrated finally at 45° C. and at a pressure of less than 40 mbar to yield N1,N19-bis((S)-16,20-diamino-15-oxo-4,7,10-trioxa-14-azaicosyl)-4,7,10,13,16-pentaoxanonadecane-1,19-diamide, also referred to herein as DiVA-PEG-DiVA-IN (63.4 g), as an oil that solidifies upon standing.

Preparation of DiVA-PEG-DiVA: N1,N19-bis((S,23E,25E,27E,29E)-16-((2E,4E,6E,8E)-3,7-dimethyl-9-(2,6,6-trimethylcyclohex-1-en-1-yl)nona-2,4,6,8-tetraenamido)-24,28-dimethyl-15,22-dioxo-30-(2,6,6-tri-methylcyclohex-1-en-1-yl)-4,7,10-trioxa-14,21-diazatriaconta-23,25,27,29-tetraen-1-yl)-4,7,10,13,16-pentaoxanonadecane-1,19-diamide

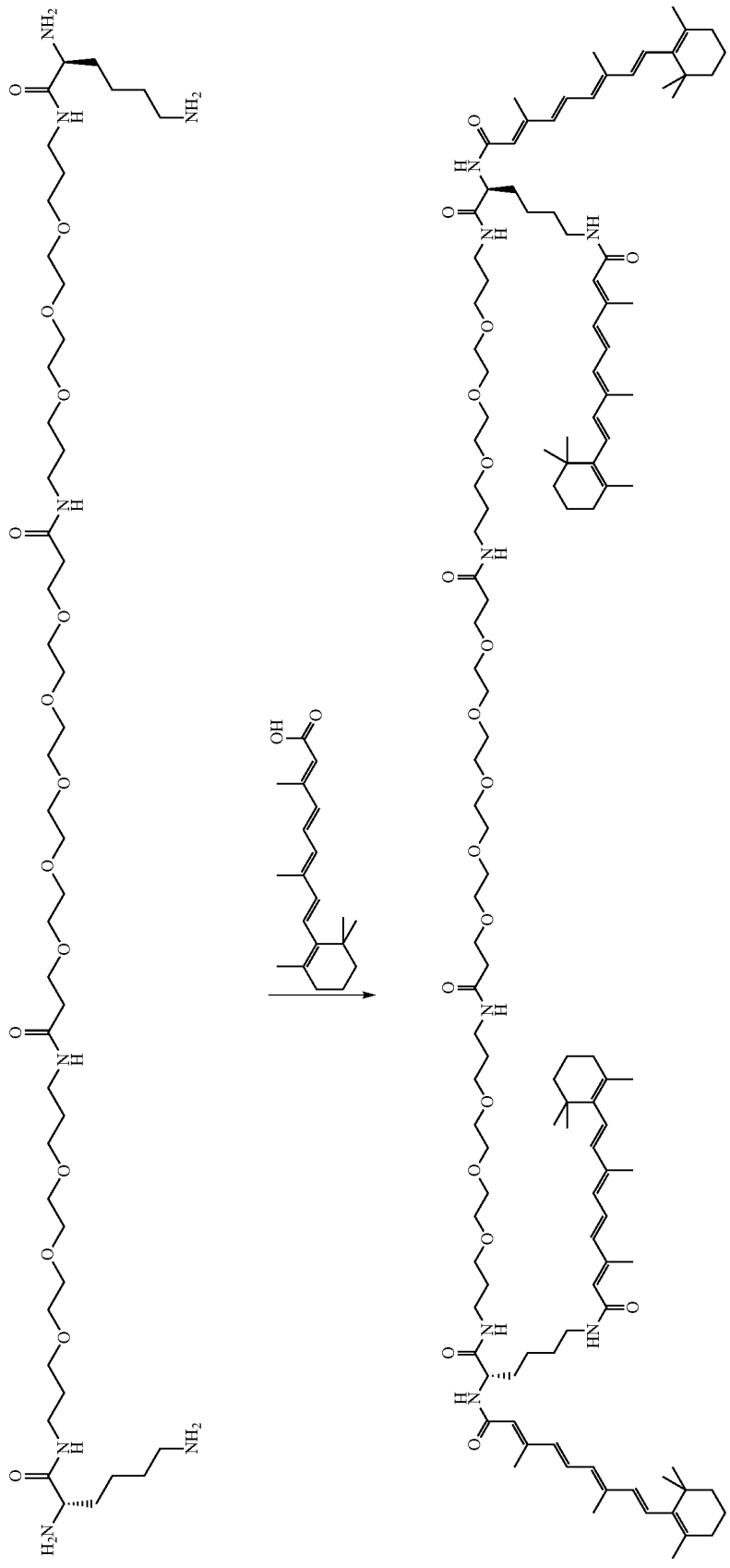

A 2 L reactor was filled with argon and charged with dichloromethane (500 mL), DiVA-PEG-DiVA-IN (52.3 g, 52.3 mmol), retinoic acid (70.6 g, 235 mmol) and 4-N,N-dimethylaminopyridine (2.6 g, 21.3 mmol). The mixture was stirred under argon until dissolved (~20 minutes). Keeping the temperature of the reaction at 10-20° C., 1-ethyl-3-(3-dimethylaminopropyl) carbodiimide) (EDCI) (70.6 g, 369 mmol) was added portion wise over a period of 10-15 minutes (the reaction was slightly exothermic for the first 30-60 minutes). The reactor was covered with aluminium foil and the mixture was stirred at 18-21° C. for 15-20 hours. Butylated hydroxytoluene (BHT) (25 mg) was added and the reaction mixture was then poured onto aqueous 6% sodium hydrogen carbonate (500 mL) while keeping an argon atmosphere over the mixture. The organic phase was separated. The aqueous phase was washed with dichloromethane (50 mL). The combined organic phase was dried with of magnesium sulphate (150 g) under inert atmosphere and protected from light. The drying agent was filtered off (pressure filter preferred) and the filter cake was washed with dichloromethane (500 mL). The filtrate was concentrated by evaporation at reduced pressure using a water bath of 35-40° C. The oily residue was added toluene (150 mL) and evaporated again to yield a semi-solid residue of 210 g. This residue was dissolved in dichloromethane (250 mL) and applied onto a column prepared from silica gel 60 (1.6 kg) and 0.5% methanol in dichloromethane) (4 L). The column was eluted with dichloromethane (7.2 L), 2), 3% methanol in dichloromethane (13 L), 5% methanol in dichloromethane (13 L), 10% methanol in dichloromethane (18 L). One 10 L fraction was taken, and then 2.5 L fractions were taken. The fractions, protected from light were sampled, flushed with argon and sealed. The fractions taken were analyzed by TLC (10% methanol in dichloromethane, UV). Fractions holding DiVA-PEG-DiVA were further analyzed by HPLC. Five fractions<85% pure (gave 32 g of evaporation residue) were re-purified in the same manner, using only 25% of the original amounts of silica gel and solvents. The fractions>85% pure by HPLC were combined and evaporated at reduced pressure, using a water bath of 35-40° C. The evaporation residue (120 g) was re-dissolved in dichloromethane (1.5 L) and slowly passed (approximately 1 hour) through a column prepared from ion exchanger Dowex 650 C, H+ form (107 g). The column was then washed with dichloromethane (1 L). The combined eluate (3277.4 g) was mixed well and a sample (25 mL, 33.33 g) was evaporated, finally at room temperature and a pressure of <0.1 mBar to afford 0.83 g of a foam. From this figure the total amount of solid material was thus calculated to a yield of 80.8 g (72.5%). The remaining 3.24 kg of solution was concentrated to 423 g. 266 g of this solution was concentrated further to yield a syrup and then re-dissolved in abs. ethanol (200 mL). Evaporation at reduced pressure, using a water bath of 35-40° C., was continued to yield a final ethanol solution of 94.8 g holding 50.8 g (53.6% w/w) of N1,N19-bis((S,23E,25E,27E,29E)-16-((2E,4E,6E,8E)-3,7-dimethyl-9-(2,6,6-trimethylcyclohex-1-en-1-yl)nona-2,4,6,8-tetraenamido)-24,28-dimethyl-15,22-dioxo-30-(2,6,6-trimethylcyclohex-1-en-1-yl)-4,7,10-trioxa-14,21-diazatriaconta-23,25,27,29-tetraen-1-yl)-4,7,10,13,16-pentaoxanonadecane-1,19-diamide, referred to herein as DiVA-PEG-DiVA, referred to herein as "DiVA". Characterized by NMR and QTOF. $^1$H NMR (400 MHz), $\delta_H$: 7.07 (t, 2H), 7.01 (t, 2H), 6.87-6.91 (m, 4.0H), 6.20-6.24 (m, 10H), 6.10-6.13 (m, 8H), 5.79 (s, 2H), 5.71 (s, 2H), 4.4 (q, 2H), 3.70 (t, 6H), 3.55-3.65 (m, ~34H), 3.59 (t, 6H), 3.4 (m, 2H), 3.25-3.33 (m, 10H), 3.16 (m, 2H), 2.44 (t, 4H), 2.33 (s, 12H), 1.97-2.01 (m, 12H), 1.96 (s, 6H), 1.7-1.9 (m, 12H), 1.69 (s, 12H), 1.5-1.65 (m, 12H), 1.35-1.5 (m, 24H), 1.01 (s, 24H). QTOF MS ESI+: m/z 2128 (M+H$^f$).

Example 10 DOPE-VA

Preparation of DOPE-VA: (Z)-(2R)-3-(((2-((2E,4E,6E,8E)-3,7-dimethyl-9-(2,6,6-trimethylcyclohex-1-en-1-yl)nona-2,4,6,8-tetraenamido)ethoxy)(hydroxy)phosphoryl)oxy)propane-1,2-diyl dioleate

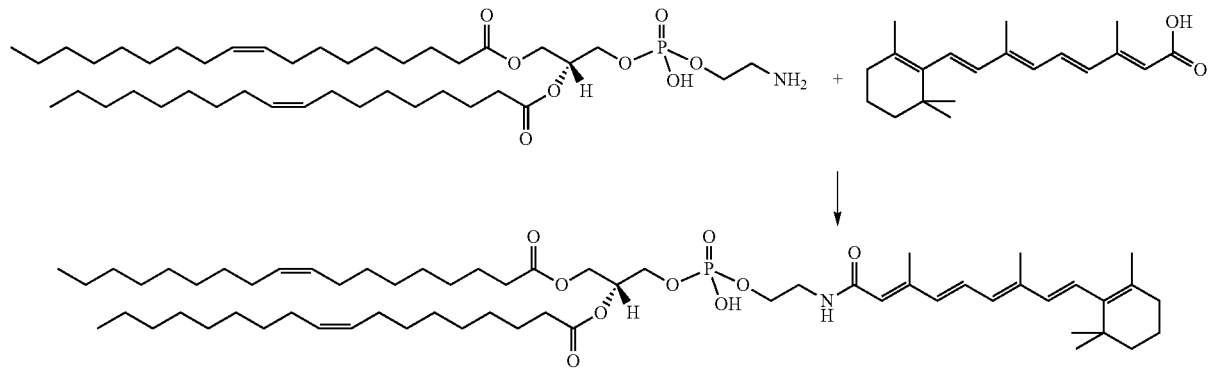

To a solution of retinoic acid (250 mg, 0.83 mmol) in diethyl ether stirring (20 mL) at −78° C., a solution of (diethylamino)sulfur trifluoride (130 µl, 0.90 mmol) in cold ether (20 mL) was added through a syringe. The reaction mixture was taken out of the cold bath and the stirring was continued at room temperature for an additional 2 hr. At the end, the solvent was removed by rotary evaporation. The residue was redissolved chloroform (50 mL) in the presence of solid Na$_2$CO$_3$ (50 mg). To this solution was added 1,2-dioleoyl-sn-glycero-3-phosphoethanolamine (600 mg, 0.81 mmol) and the reaction mixture was stirred at room temperature for an additional 24 hrs. The solvent was removed by rotary evaporation. The residue was purified by silica gel chromatography with a dichloromethane/methanol gradient to yield Z)-(2R)-3-(((2-((2E,4E,6E,8E)-3,7-dimethyl-9-(2,6,6-trimethylcyclohex-1-en-1-yl)nona-2,4,6,8-tetraenamido)ethoxy)(hydroxy)phosphoryl)oxy)propane-1,2-diyl dioleate (240 mg, 28%). 1H NMR (400 MHz, CDCl$_3$) δ 0.87 (t, 6H, CH$_3$), 1.01 (s, 6H, CH$_3$) 1.20-1.40 (m, 40H, CH$_2$), 1.40-1.60 (m, 8H, CH$_2$), 1.70 (s, 3H, CH$_3$—C═C), 1.80-2.10 (m, 8H), 2.32 (m, 4H, CH$_2$C(=O)), 3.50 (m, 2H), 3.92-4.18 (m, 5H), 4.35 (m, 2H), 5.20 (m, 1H, NHC(=O)), 5.31 (m, 4H, CH=CH), 5.80-6.90 (m, 6H, CH=CH).

Example 11 DC-VA

Preparation of DC-VA: (((2E,4E,6E,8E)-3,7-dimethyl-9-(2,6,6-trimethylcyclohex-1-en-1-yl)nona-2,4,6,8-tetraenoyl)azanediyl)bis(ethane-2,1-diyl) ditetradecanoate ( )

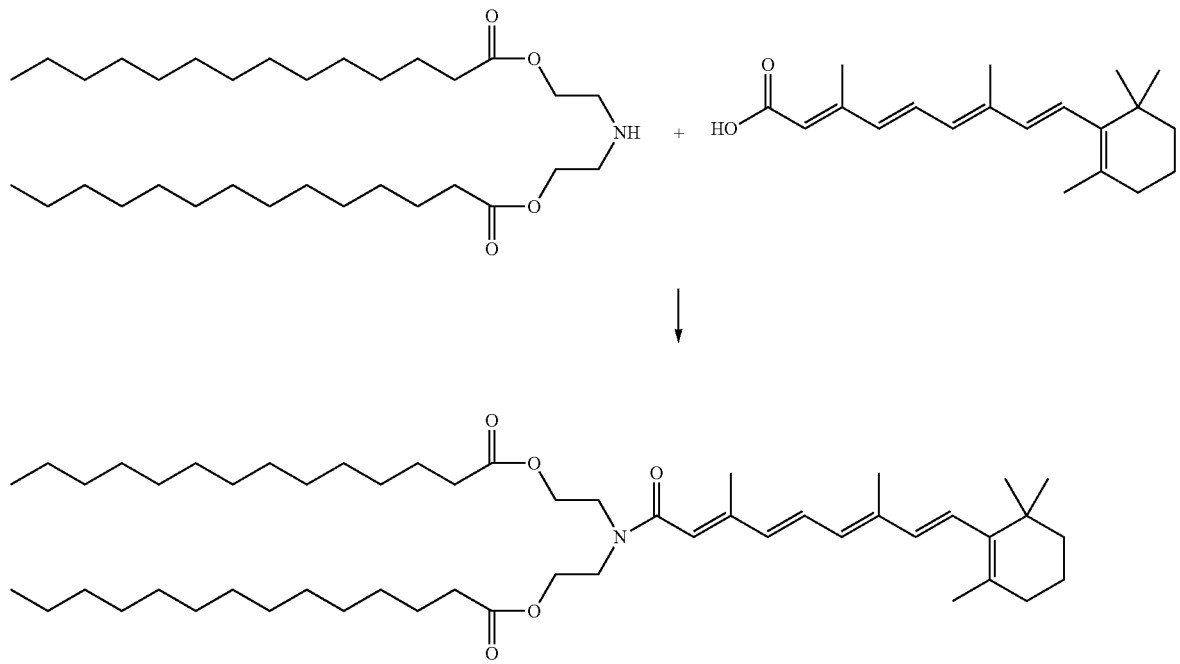

To a solution of retinoic acid (600 mg, 2.0 mmol) in diethyl ether (25 mL) stirring at −78° C., a solution of (diethylamino)sulfur trifluoride (0.3 ml, 2.1 mmol) in 5 mL of cold ether was added through a syringe. The reaction mixture was taken out of the cold bath and the stirring was continued at room temperature for an additional 1 hr. After the solvent was removed by rotary evaporation, the residue was re-dissolved in dichloromethane (20 mL) in the presence of 2 solid Na$_2$CO$_3$ (25 mg). To this solution was added the azanediylbis(ethane-2,1-diyl) ditetradecanoate (1.05 g, 2.0 mmol), and the reaction mixture was stirred at room temperature for an additional 24 hrs. The reaction mixture was diluted with dichloromethane (50 mL) and was dried over MgSO$_4$. After the solvent was removed by rotary evaporation, the residue was purified by silica gel chromatography with a dichloromethane/methanol gradient to yield (((2E,4E,6E,8E)-3,7-dimethyl-9-(2,6,6-trimethylcyclohex-1-en-1-yl)nona-2,4,6,8-tetraenoyl)azanediyl)bis(ethane-2,1-diyl) ditetradecanoate (800 mg, 50%). 1H NMR (400 MHz, CDCl$_3$) δ 0.87 (t, 6H, CH$_3$), 1.02 (s, 6H, CH$_3$) 1.20-1.40 (m, 40H, CH$_2$), 1.40-1.60 (m, 8H, CH$_2$), 1.70 (s, 3H, CH$_3$—C=C), 1.97 (s, 3H, CH$_3$—C=C), 2.05 (m, 2H, CH$_2$), 2.15 (s, 3H, CH$_3$—C=C), 2.32 (m, 4H, CH$_2$C(=O)), 3.67 (m, 4H, NCH$_2$CH$_2$O), 4.15-4.30 (m, 4H, NCH$_2$CH$_2$O), 5.80-6.90 (m, 6H, CH=CH).

Example 12 DC-6-VA

Preparation of DC-6-VA: ((6-((2E,4E,6E,8E)-3,7-dimethyl-9-(2,6,6-trimethylcyclohex-1-en-1-yl)nona-2,4,6,8-tetraenamido)hexanoyl)azanediyl)bis(ethane-2,1-diyl) ditetradecanoate ( )

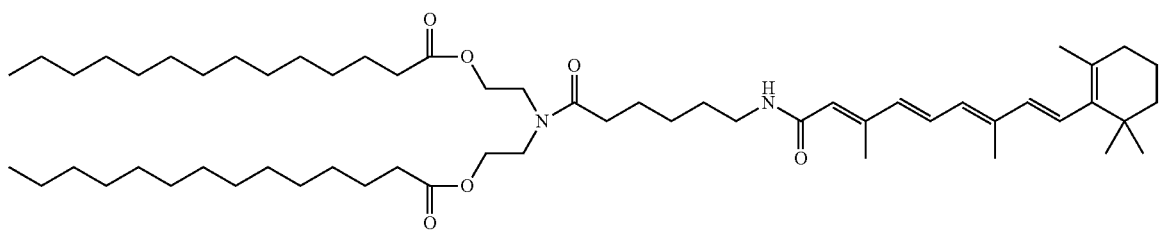

Preparation of Intermediate 1:
((6-aminohexanoyl)azanediyl)bis(ethane-2,1-diyl) ditetradecanoate TFA salt

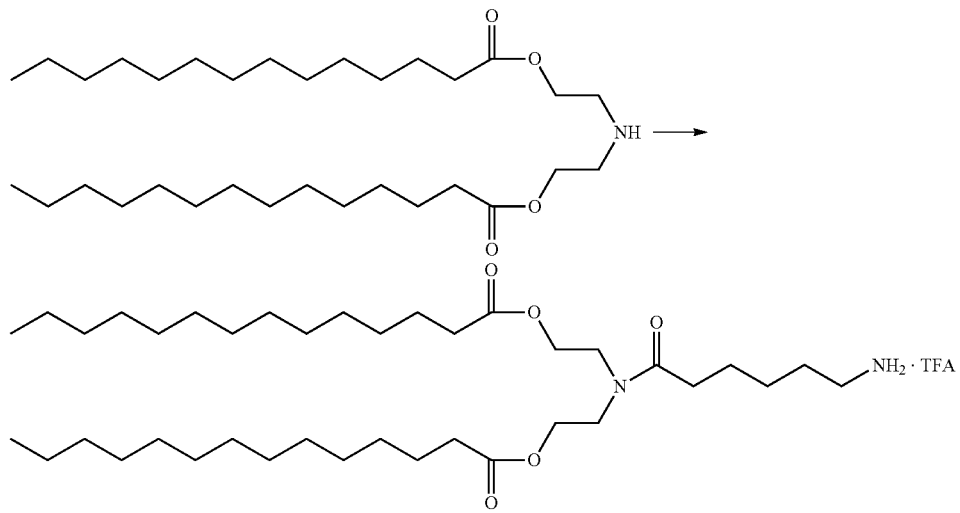

A mixture of azanediylbis(ethane-2,1-diyl) ditetradecanoate (2.5 g, 4.8 mmol), Boc-amino caproic acid (1.3 g, 5.6 mmol), N,N'-dicyclohexylcarbodiimide (1.3 g, 6.3 mmol) and N,N-diisopropylethylamine (2.6 mL, 0.015 mmol) were dissolved in pyridine (40 mL). The solution was stirred at 60° C. for 12 hours. The mixture was diluted with dichloromethane (50 mL) and washed with saline (3×50 mL). After being concentrated by rotary evaporation, the residue was treated with trifluoroacetic acid/dichloromethane (100 mL, 1:1). The mixture was concentrated and was re-dissolved in dichloromethane (50 mL) and washed with saline (3×50 mL). The organic layer was isolated and concentrated to yield ((6-aminohexanoyl)azanediyl)bis(ethane-2,1-diyl) ditetradecanoate TFA salt (1.5 g, 33%).

Preparation of DC-6-VA: ((6-((2E,4E,6E,8E)-3,7-dimethyl-9-(2,6,6-trimethylcyclohex-1-en-1-yl)nona-2,4,6,8-tetraenamido)hexanoyl)azanediyl)bis(ethane-2,1-diyl)

To a solution of retinoic acid (800 mg, 2.67 mmol) in diethyl ether (40 mL) stirring at −78° C., a solution of (diethylamino)sulfur trifluoride (0.4 mL, 22.80 mmol) in cold ether (7 mL) was added through a syringe. The reaction mixture was taken out of the cold bath and the stirring was continued at room temperature for an additional 1 hour. After the solvent was removed by rotary evaporation, the residue was re-dissolved in dichloromethane (25 mL) in the presence of solid Na$_2$CO$_3$ (40 mg). To this solution was added the 46-aminohexanoyl)azanediyl)bis(ethane-2,1-diyl) ditetradecanoate TFA salt (1.5 g, 1.6 mmol) and the reaction mixture was stirred at room temperature for an additional 24 hours The reaction mixture was diluted with dichloromethane (50 mL) and dried over MgSO$_4$. After the solvent was removed by rotary evaporation, the residue was purified by column chromatography using 5% methanol/dichloromethane as eluent to yield ((6-((2E,4E,6E,8E)-3,7-dimethyl-9-(2,6,6-trimethylcyclohex-1-en-1-yl)nona-2,4,6,8-tetraenamido)hexanoyl)azanediyl)bis(ethane-2,1-diyl) ditetradecanoate (360 mg, 24%). 1H NMR (400 MHz, CDCl$_3$) δ 0.87 (t, 6H, CH$_3$), 1.02 (s, 6H, CH$_3$) 1.20-1.40 (m, 42H, CH$_2$), 1.40-1.60 (m, 12H, CH$_2$), 1.70 (s, 3H, CH$_3$—

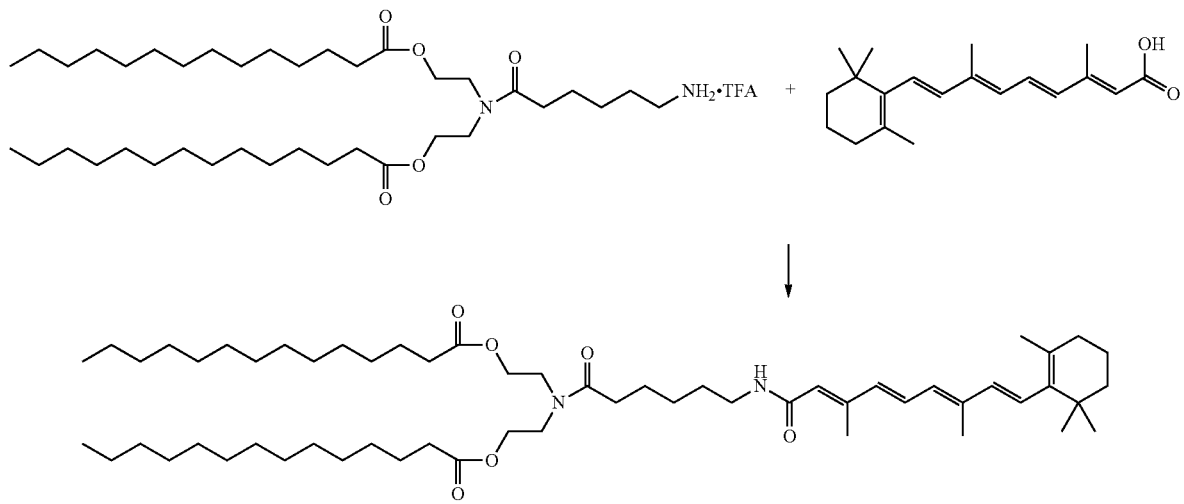

C═C), 1.97 (s, 3H, CH$_3$—C═C), 2.05 (m, 2H, CH$_2$), 2.15 (s, 3H, CH$_3$—C═C), 2.32 (m, 6H, CH$_2$C(═O)), 3.20 (m, 2H, CH$_2$NHC(═O)), 3.56 (m, 4H, NCH$_2$CH$_2$O), 4.15-4.30 (m, 4H, NCH$_2$CH$_2$O), 5.10 (m, 1H), 5.80-6.90 (m, 6H, CH═CH).

Example 13 In Vitro Evaluation of VA-siRNA-Liposome Formulations for Knockdown Efficiency in LX-2 Cell Line and Rat Primary Hepatic Stellate Cells (pHSCs)

LX2 cells (Dr. S. L. Friedman, Mount Sinai School of Medicine, NY) were grown in DMEM (Invitrogen) supplemented with 10% fetal bovine serum (Invitrogen) at 37° C. in the incubator with 5% CO$_2$. Cells were trypsinized using TryPLExpress solution (Invitrogen) for 3 minutes at 37° C. in the incubator. The cell concentration was determined by cell counting in hemocytometer and 3000 cells/well were seeded into the 96-well plates. The cells were grown for 24 h prior to transfection.

Rat primary hepatic stellate cells (pHSCs) were isolated from Sprague-Dawley rats according to the previously published method (Nat. Biotechnol. 2008, 26(4):431-42). pHSCs were grown in DMEM supplemented with 10% fetal bovine serum. Cells were grown up to two passages after isolation before using them for in vitro screening. Cells were seeded at the cell density of 1000 cells/well in 96-well plates and grown for 48 hours before using them for transfection.

Transfection with VA-siRNA-Liposome Formulations.

The transfection method is the same for LX-2 and pHSC cells. The VA-siRNA-Liposome or VA-siRNA-Lipoplex formulations were mixed with growth medium at desired concentrations. 100 μl of the mixture was added to the cells in 96-well plate and cells were incubated for 30 min at 37° C. in the incubator with 5% CO$_2$. After 30 min, medium was replaced with fresh growth medium after. After 48 h of transfection, cells were processed using Cell-to-Ct lysis reagents (Applied Biosystems) according to the manufacturer's instructions.

Quantitatve (q) RT-PCR for Measuring HSP47 mRNA Expression.

HSP47 and GAPDH TAQMAN® assays and One-Step RT-PCR master mix were purchased from Applied Biosystems. Each PCR reaction contained the following composition: One-step RT-PCR mix 5 μl, TAQMAN® RT enzyme mix 0.25 TAQMAN® gene expression assay probe (HSP47) 0.25 μl, TAQMAN® gene expression assay probe (GAPDH) 0.5 μl, RNase-free water 3.25 μl, Cell lysate 0.75 μl, total volume of 10 μl. GAPDH was used as endogenous control for the relative quantification of HSP47 mRNA levels. Quantitative RT-PCR was performed in VIIA™ 7 real time PCR system (Applied Biosciences) using an in-built Relative Quantification method. All values were normalized to the average HSP47 expression of the mock transfected cells and expressed as percentage of HSP47 expression compared to mock.

The siRNA referred to in the formulation protocols are double stranded siRNA sequence with 21-mer targeting HSP47/gp46 wherein HSP47 (mouse) and gp46 (rat) are homologs—the same gene in different species:

Rat HSP47-C double stranded siRNA used for in vitro assay (rat pHSCs)

```
                                          (SEQ. ID NO. 1)
    Sense (5'->3')  GGACAGGCCUCUACAACUAUU
```

```
                                          (SEQ. ID NO. 2)
    Antisense (3'->5')  TTCCUGUCCGGAGAUGUUGAU
```

Cationic Lipid Stock Preparation.

Stock solutions of cationic lipids were prepared by combining the cationic lipid with DOPE, cholesterol, and diVA-PEG-DiVA in ethanol at concentrations of 6.0, 5.1 and 2.7 and 2.4 mg/mL respectively. If needed, solutions were warmed up to about 50° C. to facilitate the dissolution of the cationic lipids into solution.

Empty Liposome Preparation.

A cationic lipid stock solution was injected into a rapidly stirring aqueous mixture of 9% sucrose at 40±1° C. through injection needle(s) at 1.5 mL/min per injection port. The cationic lipid stock solution to the aqueous solution ratio (v/v) is fixed at 35:65. Upon mixing, empty vesicles formed spontaneously. The resulting vesicles were then allowed to equilibrate at 40° C. for 10 minutes before the ethanol content was reduced to 12%.

Lipoplex Preparation.

The empty vesicle prepared according to the above method was diluted to the final volume of 1 mM concentration of cationic lipid by 9% sucrose. To the stirring solution, 100 μL of 5% glucose in RNase-free water was added for every mL of the diluted empty vesicle ("EV") and mixed thoroughly. 150 μL of 10 mg/mL siRNA solution in RNase-free water was then added at once and mixed thoroughly. The mixture was then diluted with 5% glucose solution with 1.750 mL for every mL of the EV used. The mixture was stirred at about 200 rpm at room temperature for 10 minutes. Using a semi-permeable membrane with ~100000 MWCO in a cross-flow ultrafiltration system using appropriately chosen peristaltic pump (e.g., Midgee Hoop, UFP-100-H24LA), the mixture was concentrated to about ⅓ of the original volume (or desired volume) and then diafiltered against 5 times of the sample volume using an aqueous solution containing 3% sucrose and 2.9% glucose. The product was then filtered through a combined filter of 0.8/0.2 micron pore size under aseptic conditions before use.

Formation of Non-diVA siRNA Containing Liposomes.

Cationic lipid, DOPE, cholesterol, and PEG conjugated lipids (e.g., Peg-Lipid) were solubilized in absolute ethanol (200 proof) at a molar ratio of 50:10:38:2. The siRNA was solubilized in 50 mM citrate buffer, and the temperature was adjusted to 35-40° C. The ethanol/lipid mixture was then added to the siRNA-containing buffer while stirring to spontaneously form siRNA loaded liposomes. Lipids were combined with siRNA to reach a final total lipid to siRNA ratio of 15:1 (wt:wt) The range can be 5:1 to 15:1, preferably 7:1 to 15:1. The siRNA loaded liposomes were diafiltered against 10× volumes of PBS (pH 7.2) to remove ethanol and exchange the buffer. Final product was filtered through 0.22 μm, sterilizing grade, PES filter for bioburden reduction. This process yielded liposomes with a mean particle diameter of 50-100 nm, PDI<0.2, >85% entrapment efficiency.

Formation of siRNA Containing Liposomes Co-Solubilized with diVA.

siRNA-diVA-Liposome formulations were prepared using the method described above. diVA-PEG-diVA was co-solubilized in absolute ethanol with the other lipids (cationic lipid, DOPE, cholesterol, and PEG-conjugated lipids at a ratio of 50:10:38:2) prior to addition to the siRNA containing buffer. Molar content of diVA-PEG-diVA ranged from 0.1 to 5 molar ratio. This process yielded liposomes with a mean particle diameter of 50-100 nm, PDI<0.2, >85% entrapment efficiency.

Formation of siRNA Containing Liposomes with Cationic Lipids.

siRNA-diVA-Liposome formulations and siRNA-Liposome formulations were prepared using the method described above. Cationic lipid can be, for example, DODC, HEDC, HEDODC, DC-6-14, or any combination of these cationic lipids.

Formation of siRNA Containing Liposomes Decorated with diVA.

siRNA-Liposome formulations were prepared using the method described above and diluted to a siRNA concentration of 0.5 mg/mL in PBS. Cationic lipid can be DODC, HEDC, HEDODC, DC-6-14, or any combination of these cationic lipids. diVA-PEG-diVA was dissolved in absolute ethanol (200 proof) to a final concentration ranging from 10 to 50 mg/mL. An appropriate amount of ethanol solution was added to the siRNA-Liposome solution to yield a final molar percentage between 2 to 10 mol %. Solution was plunged up and down repeatedly with a pipette to mix. diVA-PEG-diVA concentration and ethanol addition volume were adjusted to keep the addition volume>1.0 µL and the final ethanol concentration<3% (vol/vol). Decorated liposomes were then gently shaken at ambient temperature for 1 hr on an orbital shaker prior to in vitro or in vivo evaluation.

FIG. 1 shows that addition of the VA-conjugate to liposomes via decoration improved the knockdown efficacy of siRNA, enhancing siRNA activity. The dose for all samples was 867 nM siRNA HSP47-C. The results showed that in every instance where a VA-conjugate was added to liposomes, siRNA activity was enhanced compared to liposomes without a retinoid and compared to liposomes decorated with free (non-conjugated) retinol. RNAiMAX™ was a commercial transfection reagent.

Figure 2:
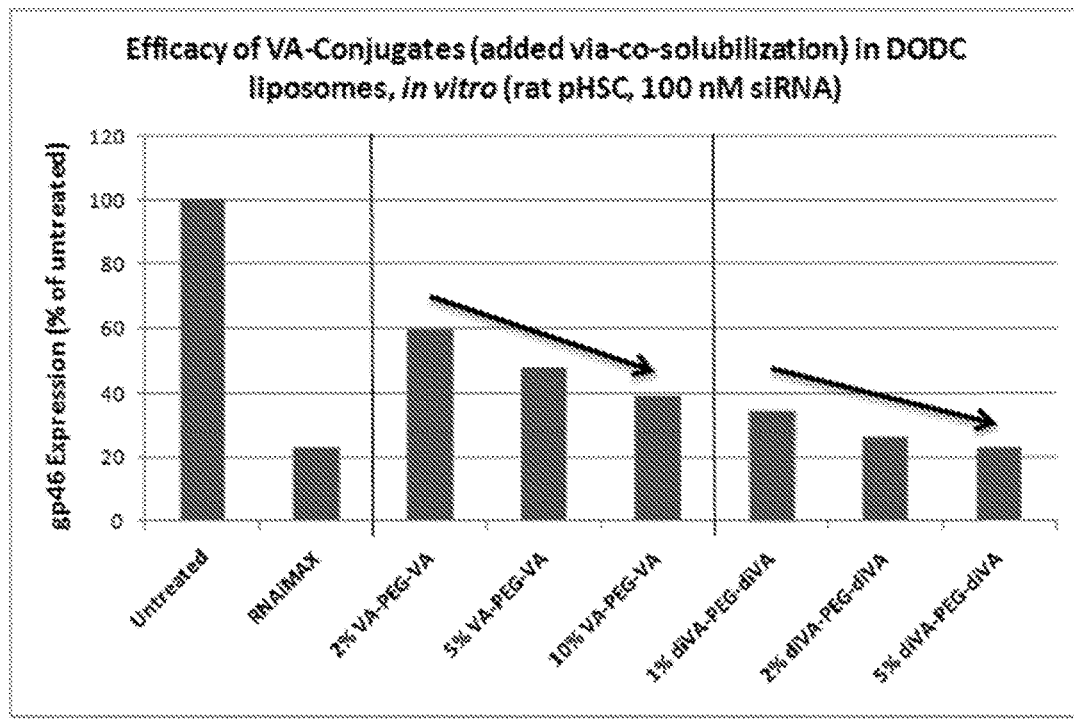
FIG. 2 shows VA-conjugate addition to liposomes via co-solubilization in DODC liposomes enhances siRNA activity under conditions similar to those in FIG. 1.

FIG. 2 shows that addition of VA-conjugates to liposomes via co-solubilization improves knockdown efficacy of siRNA. These were DODC containing liposomes with VA-conjugates added via co-solubilization. The formulation is 50:10:38:2:X, where X=1 to 10 (DODC:DOPE:cholesterol:PEG-Lipid:VA-conjugate, mole ratio). The concentration in every instance was 100 nM siRNA HSP47-C. The results show that addition of VA-conjugates to liposomes via cosolubilization enhances siRNA activity.

Figure 3:
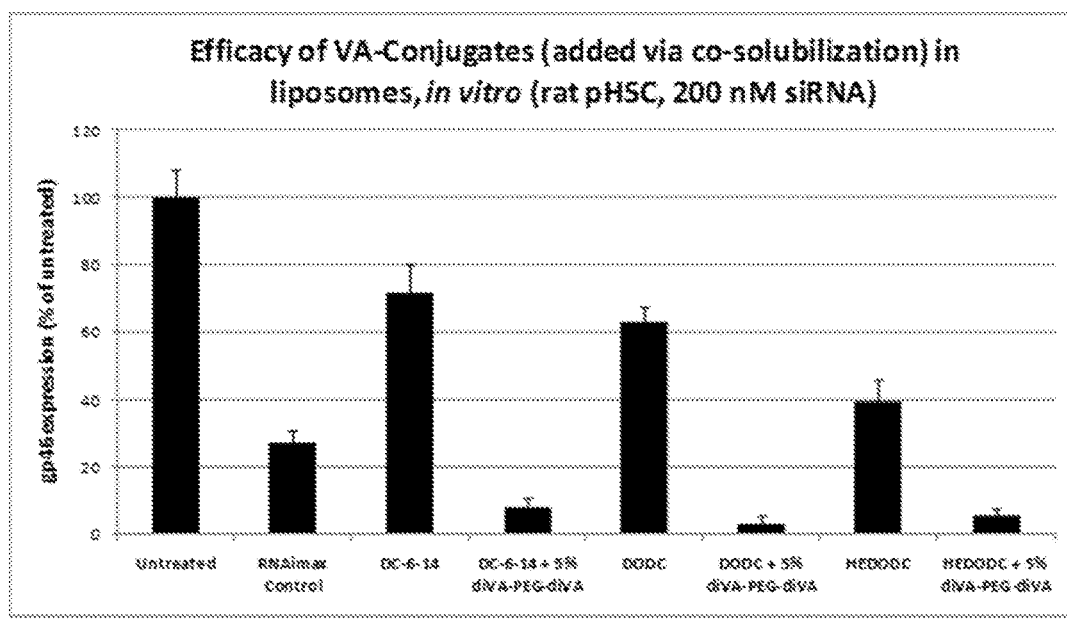
FIG. 3 shows VA-conjugate addition to liposomes via co-solubilization enhances siRNA activity under conditions similar to those in FIG. 2.

FIG. 3 shows that addition of VA-conjugate to liposomes via co-solubilization dramatically improves the knockdown efficacy of siRNA. Results include three different liposomes, DC-6-14, DODC, HEDODC with VA-conjugates added via co-solubilization. The formulation is the same for all, 50:10:38:2, cationic lipid:DOPE:cholesterol:Peg-Lipid, with only the cationic lipid varying. The concentration of siRNA is 200 nM siRNA HSP47-C is the same for all. The results show in that VA-conjugate addition to liposomes having different cationic lipids significantly enhanced siRNA activity, when prepared by co-solubilization.

Figure 4:
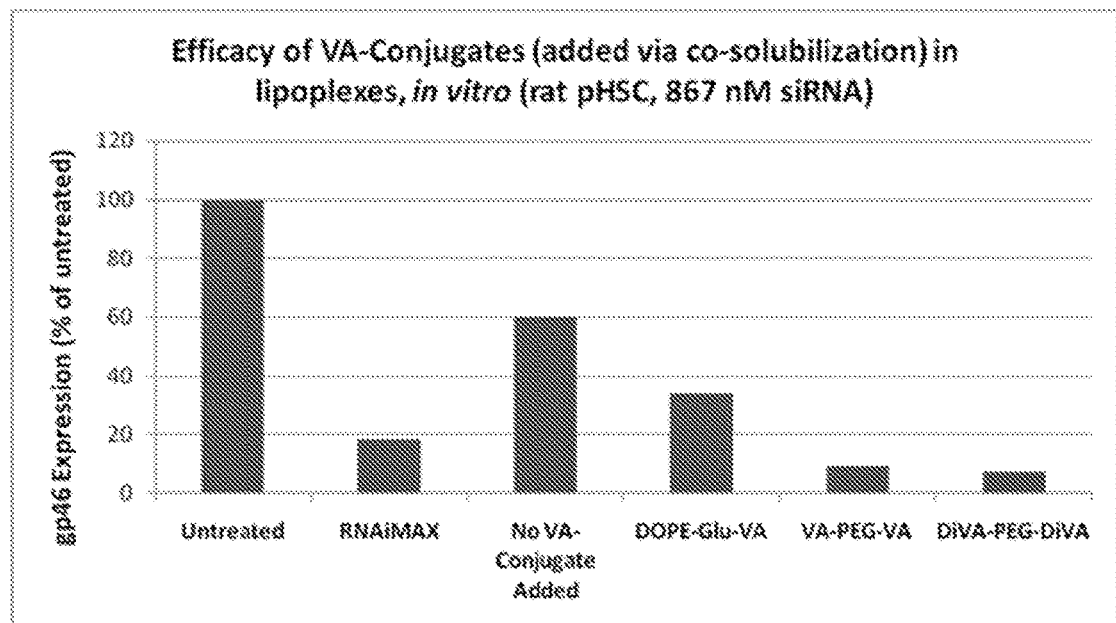
FIG. 4 shows VA-conjugate addition to lipoplexes via co-solubilization enhances siRNA activity under conditions similar to those in FIG. 1.

FIG. 4 shows that addition of VA-conjugates to lipoplexes having DC-6-14 cationic lipid via co-solubilization, and siRNA coating the exterior of the liposome enhances siRNA activity. The formulation is a 40% lipoplex formulation, 40:30:30, DC-6-14:DOPE:cholesterol. The concentration for all samples is 867 nM siRNA HSP47-C. The results show that VA-conjugate addition to lipoplexes via co-solubilization enhance siRNA activity.

Figure 5:
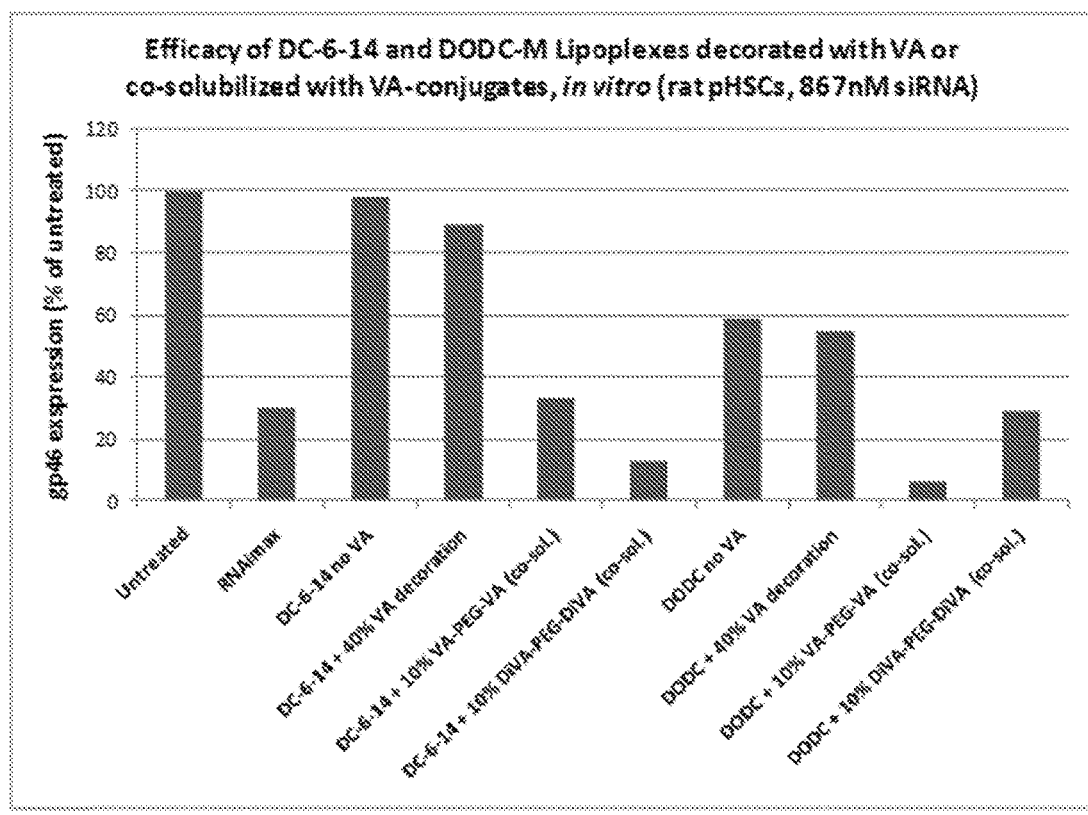
FIG. 5 shows VA-conjugate addition to lipoplexes via co-solubilization vs. decoration under conditions similar to those in FIG. 1.

FIG. 5 shows that addition of VA-conjugate to lipoplexes formed via co-solubilization compared to lipoplexes with VA-conjugate added via decoration. These results are from DC-6-14 and DODC lipoplexes. The formulation consists of 40:30:30, DC-6-14:DOPE:cholesterol. The concentration in each sample is 867 nM siRNA HSP47-C. VA-conjugate addition via co-solubilization significantly improves knockdown efficacy in vitro, relative to VA-conjugates added by decoration.

Example 14 In Vivo Experiments

Female C57Bl/6 retired breeder mice (Charles River) with a weight range of 24-30 grams were used. Animals were randomly distributed by weight into ten groups of ten animals each. All animal procedures were approved by Bio-Quant's IACUC and/or Attending Veterinarian as necessary and all animal welfare concerns were addressed and documented. Mice were anesthetized with Isoflurane and exsanguinated via the inferior vena cava.

Mouse HSP47-C double stranded siRNA used in formulations for in vivo assay (mouse CCl4 model)

```
                                        (SEQ. ID NO. 3)
    Sense (5'->3')  GGACAGGCCUGUACAACUAUU (SEQ. ID NO. 4)
    Antisense (3'->5')  TTCCUGUCCGGACAUGUUGAU
```

Upregulation of heat shock protein 47 (HSP47) was induced via intraperitoneal injection of $CCl_4$ ($CCl_4$ in olive oil, 1:7 (vol/vol), 1 µL per gram body weight) given every other day for 7 days (day 0, 2, 4, 6). On day 3 mice were treated for 4 consecutive days (day 3, 4, 5, 6) with liposome or lipoplex formulations of described herein or PBS by IV injection into the tail vein. One group of ten mice (naïve) received neither $CCl_4$ treatment nor IV injection and served as the control group for normal HSP47 gene expression.

| Experimental Timeline | | | | | | | | |
|---|---|---|---|---|---|---|---|---|
| | Day | | | | | | | |
| | 0 | 1 | 2 | 3 | 4 | 5 | 6 | 7 |
| $CCl_4$ IP Injection | X | X | X | X | X | X | X | |
| Test Article IV Injection | | | | X | X | X | X | |
| Sample Collection (n = 10) | | | | | | | | X |

On day 7 and 24 hours after final IV injection, all remaining mice were sacrificed and the livers were perfused with PBS prior to collecting liver samples for PCR analysis. An approximate 150 mg sample from each mouse liver was collected and placed in 1.5 mL RNALATER® stabilization reagent (Qiagen) and stored at 2-8° C. until analysis. Liver samples were not collected from areas of clear and marked liver damage and/or necrosis.

Figure 6:
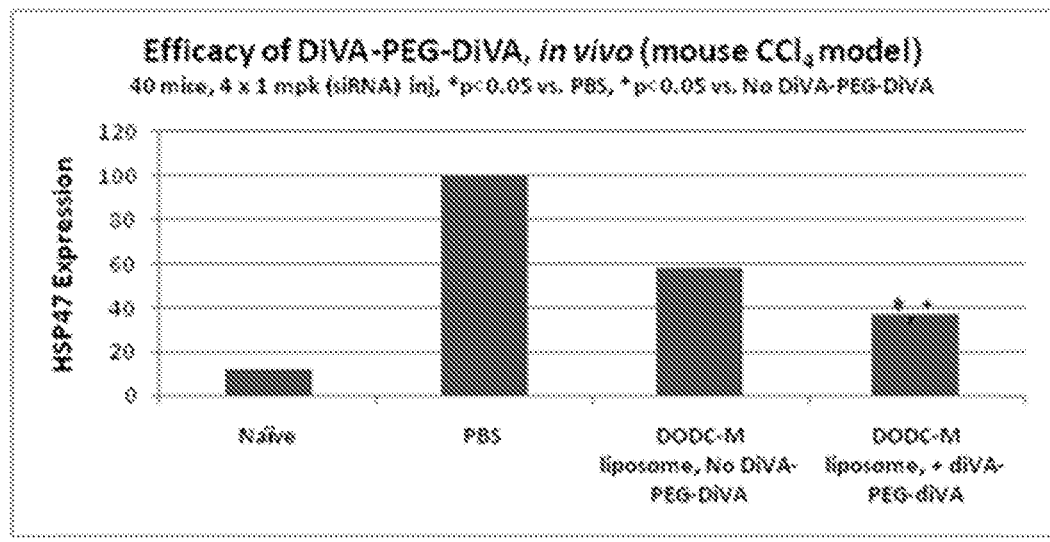
FIG. 6 shows in vivo efficacy in a murine, CCl4 model.
Figure 7:
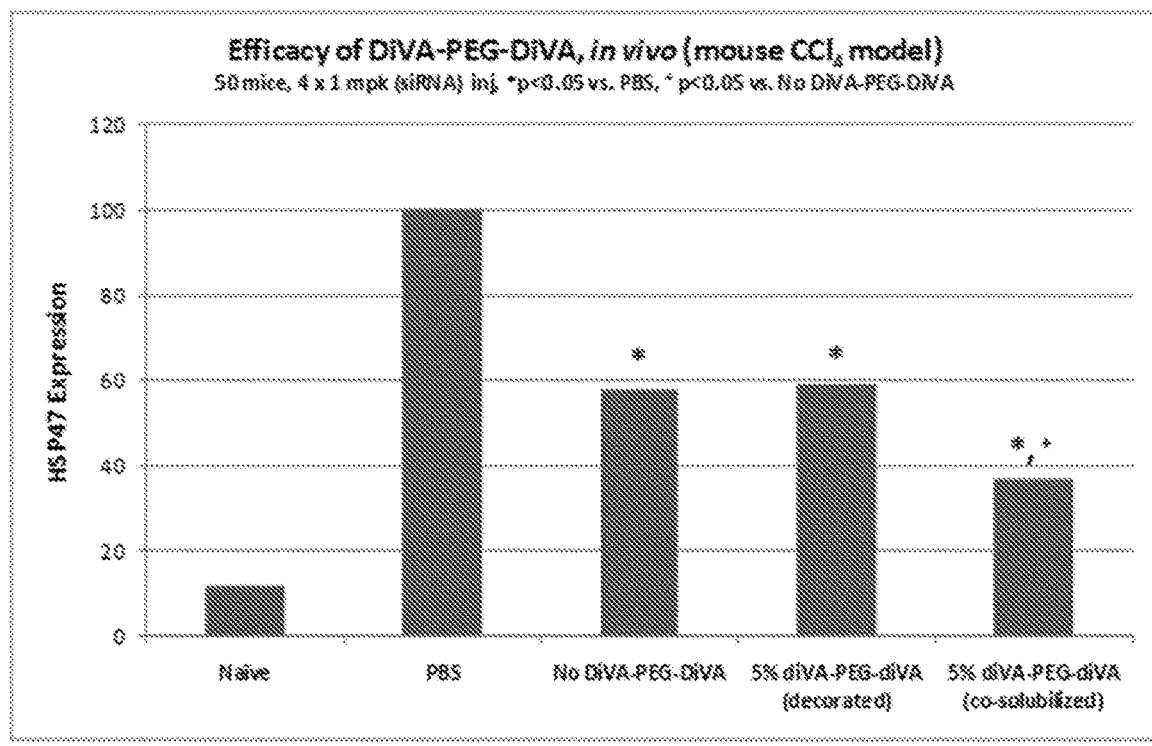
FIG. 7 shows in vivo efficacy of decorated vs. co-solubilized retinoid conjugates.

Total RNA from mouse livers was extracted using RNEASY® columns (Qiagen) according to the manufacturer's protocol. 20 ng of total RNA was used for quantitative RT-PCR for measuring HSP47 expression. HSP47 and GAPDH TAQMAN® assays and One-Step RT-PCR master mix were purchased from Applied Biosystems. Each PCR reaction contained the following composition: One-step RT-PCR mix 5 µl, TAQMAN® RT enzyme mix 0.25 µl, TAQMAN® gene expression assay probe (HSP47) 0.25 µl, TAQMAN® gene expression assay probe (GAPDH) 0.5 µl, RNase-free water 3.25 µl, RNA 0.75 µl, Total volume of 10 µl. GAPDH was used as endogenous control for the relative quantification of HSP47 mRNA levels. Quantitative RT- PCR was performed in VIIA™ 7 real time PCR system (Applied Biosciences) using an in-built Relative Quantification method. All values were normalized to the average HSP47 expression of the naïve animal group and expressed as percentage of HSP47 expression compared to naïve group (FIGS. 6 and 7).

Example 15 Synthesis of satDiVA

Preparation of N1,N19-bis((16S)-16-(3,7-dimethyl-9-(2,6,6-trimethylcyclohex-1-en-1-yl)nonanamido)-24,28-dimethyl-15,22-dioxo-30-(2,6,6-trimethylcyclohex-1-en-1-yl)-4,7,10-trioxa-14,21-diazatriacontyl)-4,7,10,13,16-pentaoxanonadecane-1,19-diamide (satDIVA)

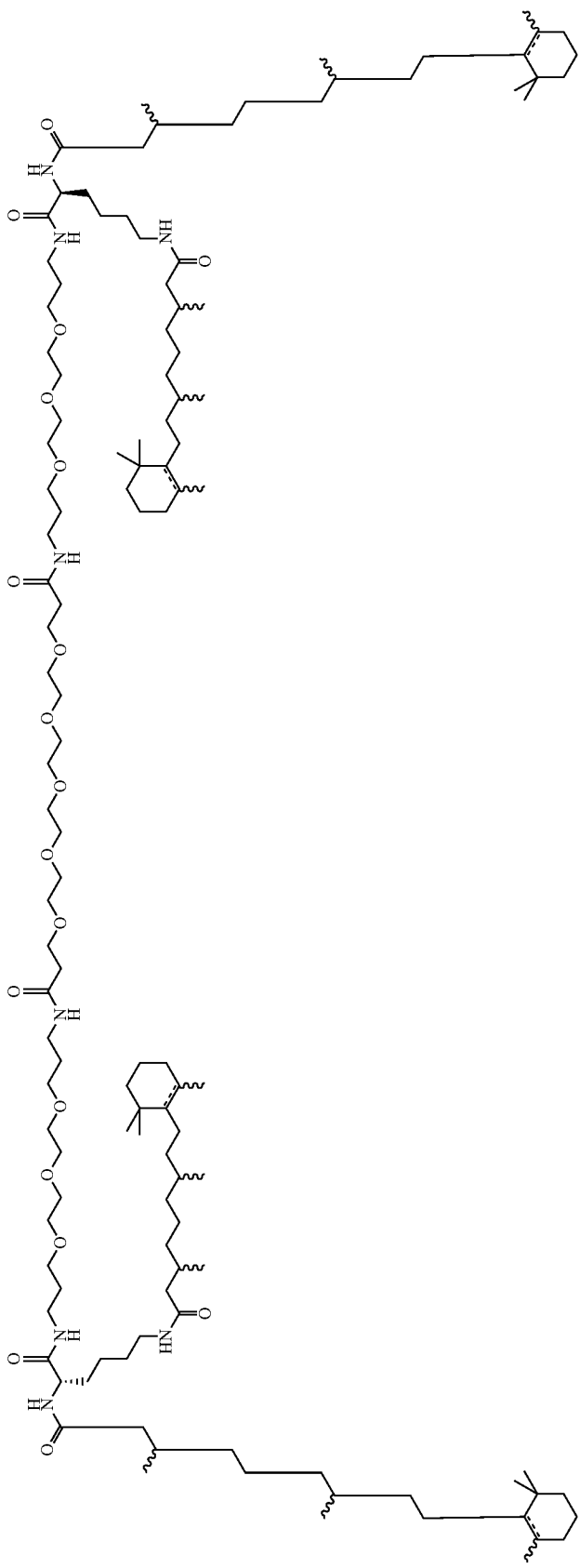

Preparation of Intermediate 1: 3,7-dimethyl-9-(2,6,6-trimethylcyclohex-1-en-1-yl)nonanoic acid

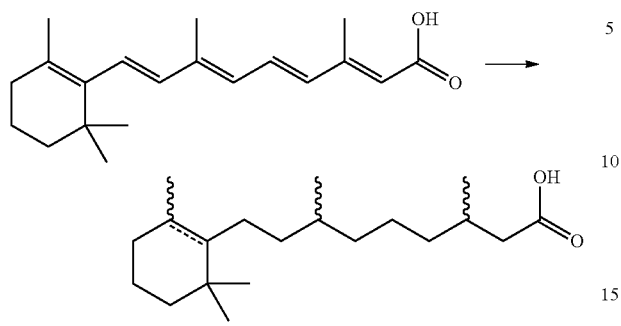

All-trans retinoic acid (2000 mg, 6.66 mmol) was dissolved in hexanes/IPA (3:1, 40 mL) with the aid of sonication. Material was placed in a Parr-shaker bottle and flushed with inert gas. 10% Pd/C (200 mg) was added and the vessel was once again flushed with inert gas. Material was placed on the Parr-Shaker for 12 hours with >70 psi hydrogen gas. The reaction mixture was then filtered through a pad of CELITE® and concentrated to yield 3,7-dimethyl-9-(2,6,6-trimethylcyclohex-1-en-1-yl)nonanoic acid (2 g).

Preparation of satDIVA: N1,N19-bis((16S)-16-(3,7-dimethyl-9-(2,6,6-trimethylcyclohex-1-en-1-yl)nonanamido)-24,28-dimethyl-15,22-dioxo-30-(2,6,6-trimethylcyclohex-1-en-1-yl)-4,7,10-trioxa-14,21-diazatriacontyl)-4,7,10,13,16-pentaoxanonadecane-1,19-diamide

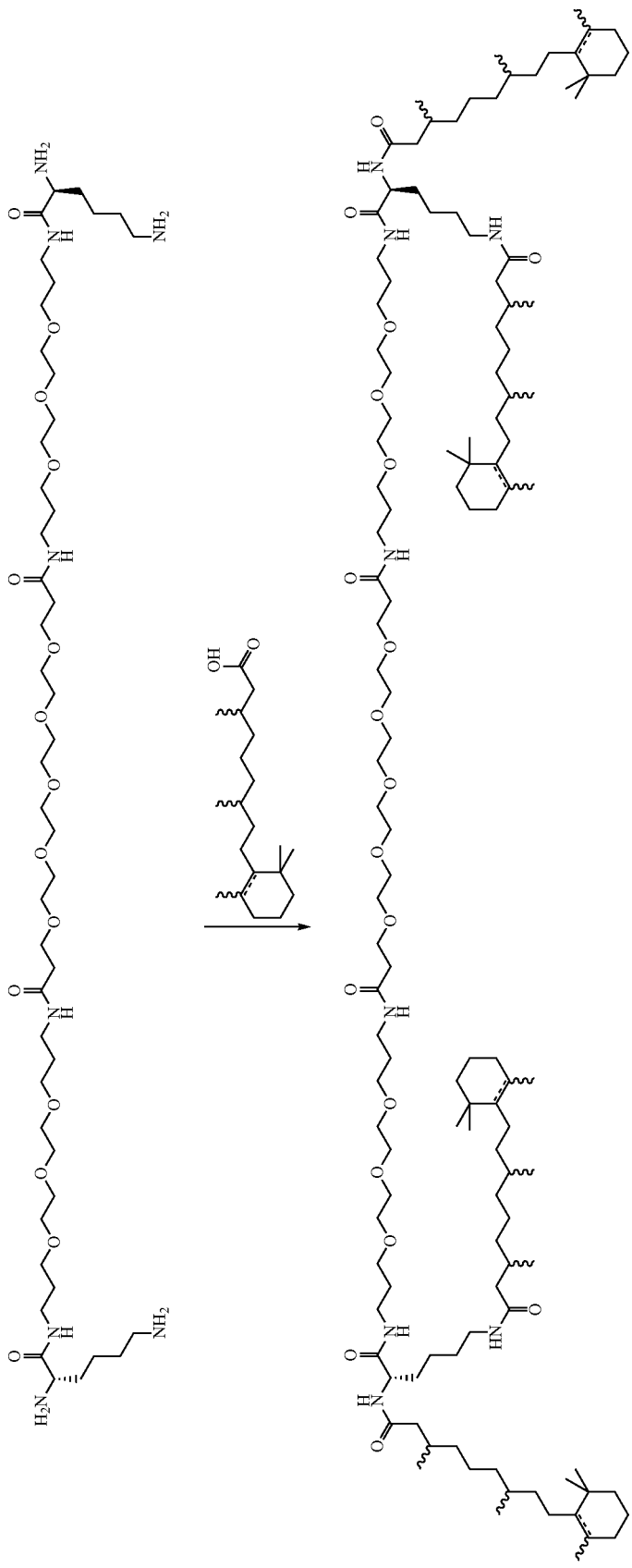

N1,N19-bis((16S)-16-(3,7-dimethyl-9-(2,6,6-trimethylcyclohex-1-en-1-yl)nonanamido)-24,28-dimethyl-15,22-dioxo-30-(2,6,6-trimethylcyclohex-1-en-1-yl)-4,7,10-trioxa-14,21-diazatriacontyl)-4,7,10,13,16-pentaoxanonadecane-1,19-diamide (satDIVA) was prepared in similar fashion as diva-PEG-diVA from previously described N1,N19-bis((S)-16,20-diamino-15-oxo-4,7,10-trioxa-14-azaicosyl)-4,7,10,13,16-pentaoxanonadecane-1,19-diamide with the substitution of 3,7-dimethyl-9-(2,6,6-trimethylcyclohex-1-en-1-yl)nonanoic acid for all-trans retinoic acid. QTOF MS ESI+: m/z 2161, 2163, 2165 and 2167 (M+H+)

Example 16 Synthesis of simDiVA

Preparation of N1,N19-bis((S)-15,22-dioxo-30-(2,6,6-trimethylcyclohex-1-en-1-yl)-16-(9-(2,6,6-trimethylcyclohex-1-en-1-yl)nonanamido)-4,7,10-trioxa-14,21-diazatriacontyl)-4,7,10,13,16-pentaoxanonadecane-1,19-diamide (simDiVA)

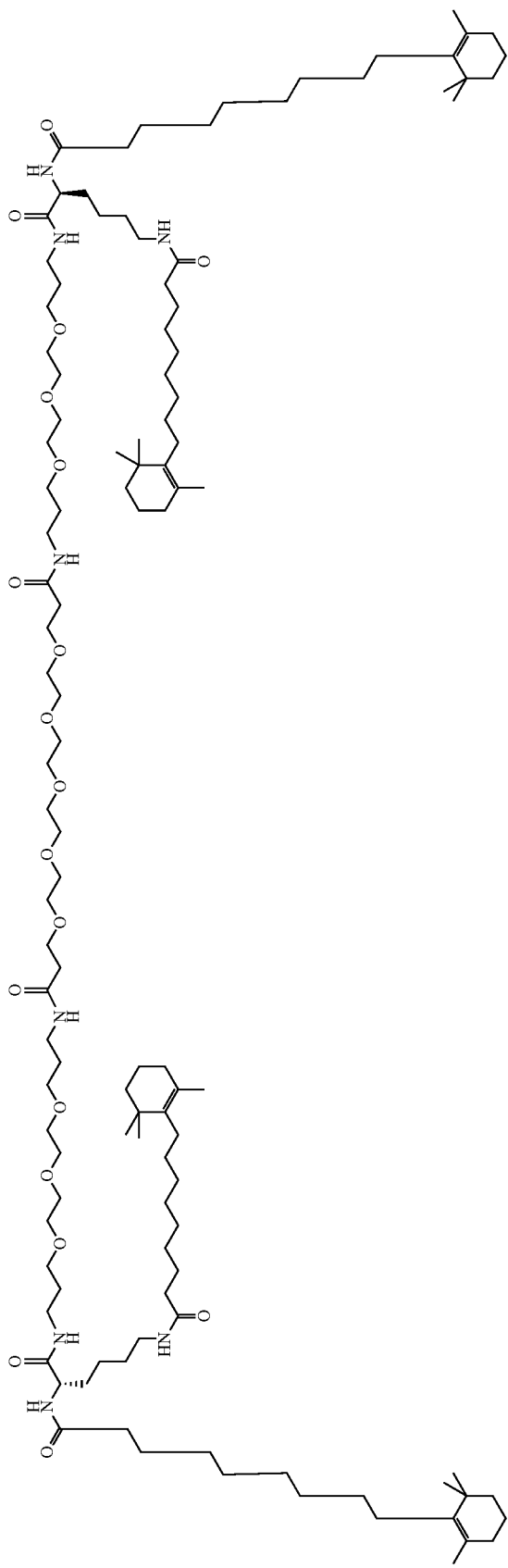

Preparation of Intermediate 1: 2,6,6-trimethylcyclohex-1-en-1-yl trifluoromethanesulfonate

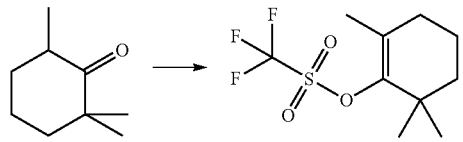

To a solution of 2,2,6-trimethylcyclohexanone in dry THF at −78° C. under nitrogen was added dropwise a 2 M lithium diisopropylamide solution. The mixture was stirred at −78° C. for 3 h. A solution of N-phenyl-bis(trifluoromethanesulfonimide) in THF was then added dropwise (at −78° C.). The reaction flask was packed in dry-ice and stirred for 12 hours. The stirring was continued at room temperature for 3 h under which time all material had dissolved. The reaction mixture was concentrated and the residue was added slowly to hexane (350 mL) under vigorous stirring. The solid material was removed by filtration and washed with hexane (2×50 mL). The filtrate was concentrated and more hexane (150 mL) was added. The solid material was removed by filtration and the filtrate was concentrated. The precipitation was repeated one more time after which the residue was purified by flash chromatography (silica, hexane) to give 2,6,6-trimethylcyclohex-1-en-1-yl trifluoromethanesulfonate as a colorless oil (23.2 g, 60% yield).

Preparation of Intermediate 2: ethyl 9-(bromozincio)nonanoate

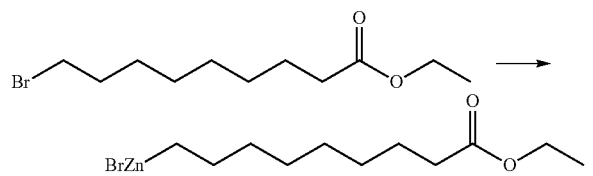

In a dry reaction tube under nitrogen were charged zinc dust (3.70 g, 56.6 mmol), iodine (479 mg, 1.89 mmol) and dry DMA (20 mL). The mixture was stirred at room temperature until the color of iodine disappeared. Ethyl 9-bromononanoate was added, and the mixture was stirred at 80° C. for 4 hours and then at room temperature for 12 hours. (Completion of the zinc insertion reaction was checked by GCMS analysis of the hydrolyzed reaction mixture.) The reaction mixture was used without further treatment in the subsequent step. GCMS m/z 186 [M]+(ethyl nonanoate).

Preparation of Intermediate 3: ethyl 9-(2,6,6-trimethylcyclohex-1-en-1-yl)nonanoate

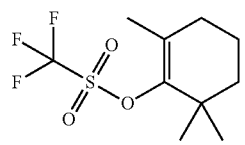

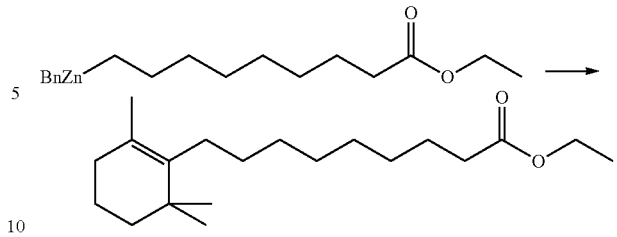

To ethyl 9-(bromozincio)nonanoate (37.7 mmol) in dimethylacetamide under nitrogen was added 2,6,6-trimethylcyclohex-1-en-1-yltrifluoromethanesulfonate (10.8 g, 39.6 mmol) followed by tetrakis(triphenylphosphine)palladium (0) (872 mg, 0.754 mmol). The mixture was stirred at 95° C. for 2 hours. The reaction mixture was allowed to cool and was then poured into diethyl ether (100 mL). The upper layer was decanted and the lower layer was washed twice with diethyl ether (2×25 mL). The combined ether layers were washed with sat NH$_4$Cl and brine, dried (MgSO$_4$) and concentrated to give crude material (~12 g). The material was purified by flash chromatography (silica, 0 to 1.5% EtOAc in hexane). The obtained oil was stirred under vacuum for 8 hours in order to remove the side-product, ethyl nonanoate, and was then purified by a second flash chromatography (silica, 0 to 15% toluene in hexane). The fractions were analyzed by LCMS and GCMS. The purest fractions were collected and concentrated at a temperature below 25° C. to give ethyl 9-(2,6,6-trimethylcyclohex-1-en-1-yl)nonanoate as a colorless oil (6.16 g, 53% yield over two steps). LCMS ESI+m/z 309 [M+H]+; GCMS m/z 308 [M]+.

Preparation of Intermediate 4: 9-(2,6,6-trimethylcyclohex-1-en-1-yl)nonanoic acid

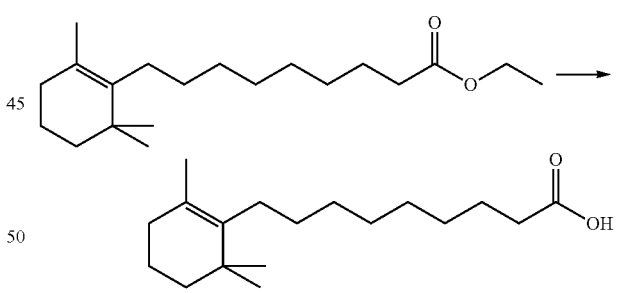

To ethyl 9-(2,6,6-trimethylcyclohex-1-en-1-yl)nonanoate (13.2 g, 42.9 mmol) in ethanol (80 mL) was added 4 M KOH (43 mL). The mixture was stirred at room temperature for 1.5 hours. Water (350 mL) was added and the solution was washed with tert-butyl methyl ether (2×100 mL). The SimVA, aqueous phase was cooled, acidified with 4 M HCl (~45 mL) and extracted with pentane (3×100 mL). The combined pentane extracts were washed with water (200 mL), dried (MgSO4), filtered, concentrated and dried under high vacuum. The material was redissolved in pentane (100 mL), concentrated and dried under high vacuum to give 9-(2,6,6-trimethylcyclohex-1-en-1-yl)nonanoic acid as a colorless oil (11.1 g, 92% yield). MS ESI-m/z 279 [M−H]−.

Preparation of simdiVA: N1,N19-bis((S)-15,22-dioxo-30-(2,6,6-trimethylcyclohex-1-en-1-yl)-16-(9-(2,6,6-trimethylcyclohex-1-en-1-yl)nonanamido)-4,7,10-trioxa-14,21-diazatriacontyl)-4,7,10,13,16-pentaoxanonad

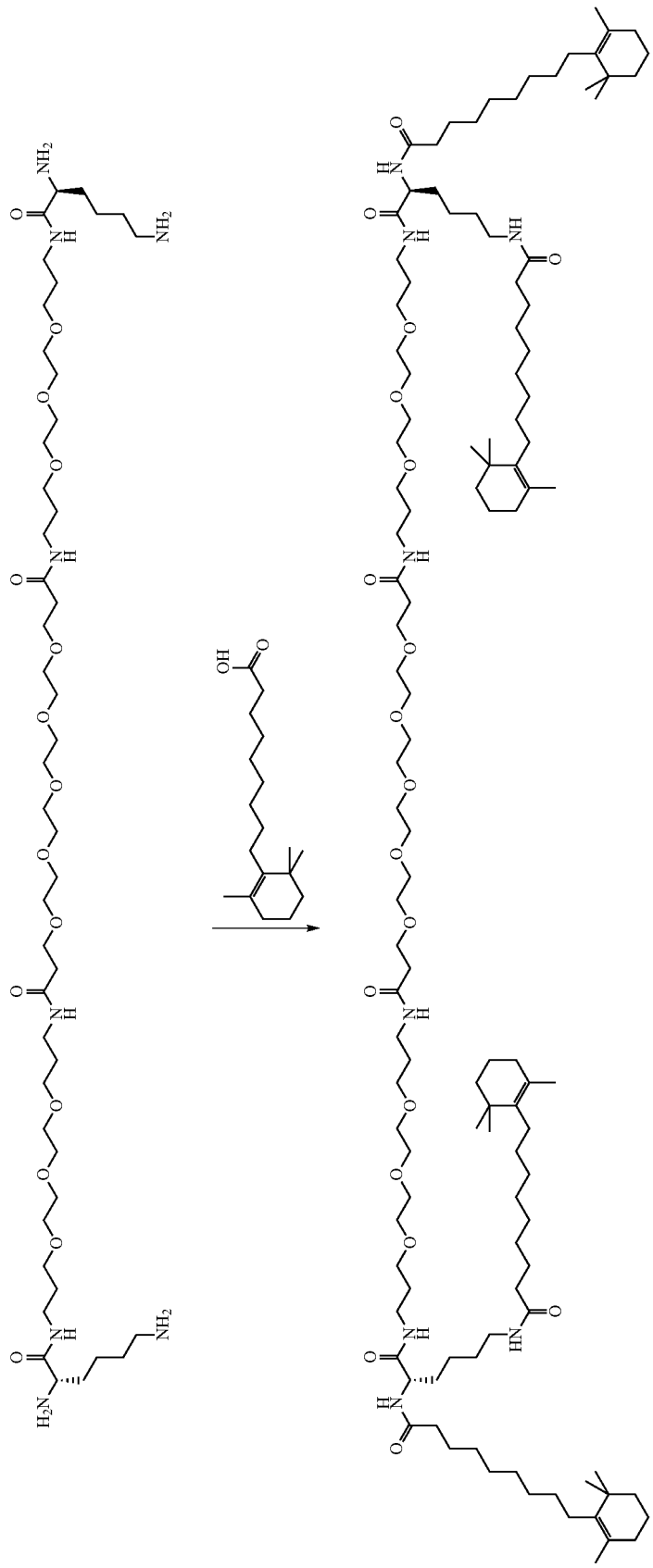

simDIVA was prepared in similar fashion as diVA from previously described N1,N19-bis((S)-16,20-diamino-15-oxo-4,7,10-trioxa-14-azaicosyl)-4,7,10,13,16-pentaoxanonadecane-1,19-diamide with the substitution of 9-(2,6,6-trimethylcyclohex-1-en-1-yl)nonanoic acid for all-trans retinoic acid. QTOF MS ESI+: m/z 2050 (M+H+)

Example 17 Synthesis of DiVA-PEG18

Preparation of (2E,2'E,2"E,4E,4'E,4"E,6E,6'E,6"E, 8E,8'E,8"E)-N,N',N"-((5R,69R,76E,78E,80E,82E)-77,81-dimethyl-6,68,75-trioxo-83-(2,6,6-trimethylcyclohex-1-en-1-yl)-10,13,16,19,22,25,28,31,34,37,40,43,46,49,52,55,58,61,64-nonadecaoxa-7,67,74-triazatrioctaconta-76,78,80,82-tetraene-1,5,69-triyl) tris(3,7-dimethyl-9-(2,6,6-trimethylcyclohex-1-en-1-yl)nona-2,4,6,8-tetraenamide) (DIVA-PEG18)

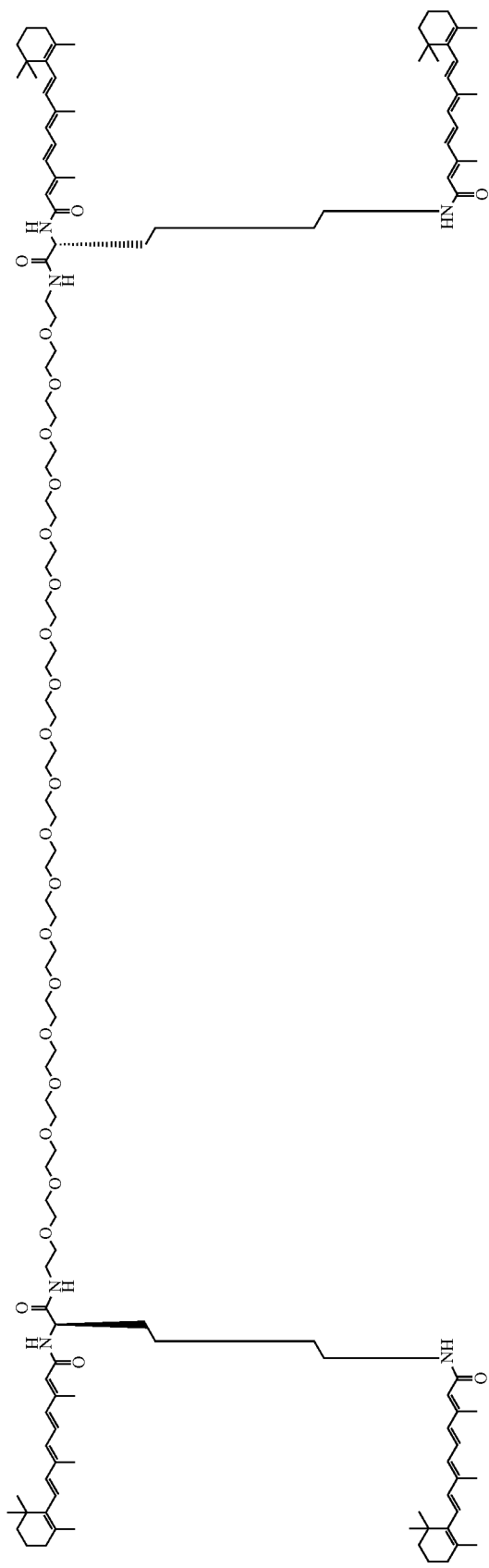

(2E,2'E,2"E,4E,4'E,4"E,6E,6'E,6"E,8E,8'E,8"E)-N,N',N"-((5R,69R,76E,78E,80E,82E)-77,81-dimethyl-6,68,75-trioxo-83-(2,6,6-trimethylcyclohex-1-en-1-yl)-10,13,16,19,22,25,28,31,34,37,40,43,46,49,52,55,58,61,64-nonadecaoxa-7,67,74-triazatrioctaconta-76,78,80,82-tetraene-1,5,69-triyl)tris(3,7-dimethyl-9-(2,6,6-trimethylcyclohex-1-en-1-yl)nona-2,4,6,8-tetraenamide) (DIVA-PEG18) was prepared in similar fashion as diVA with the substitution of $PEG_{18}$ diamine for diamido-$dPEG_{11}$-diamine. LCMS ESI+: m/z 2305 (M+Na).

Example 18 Synthesis OF TriVA

Preparation of TriVA

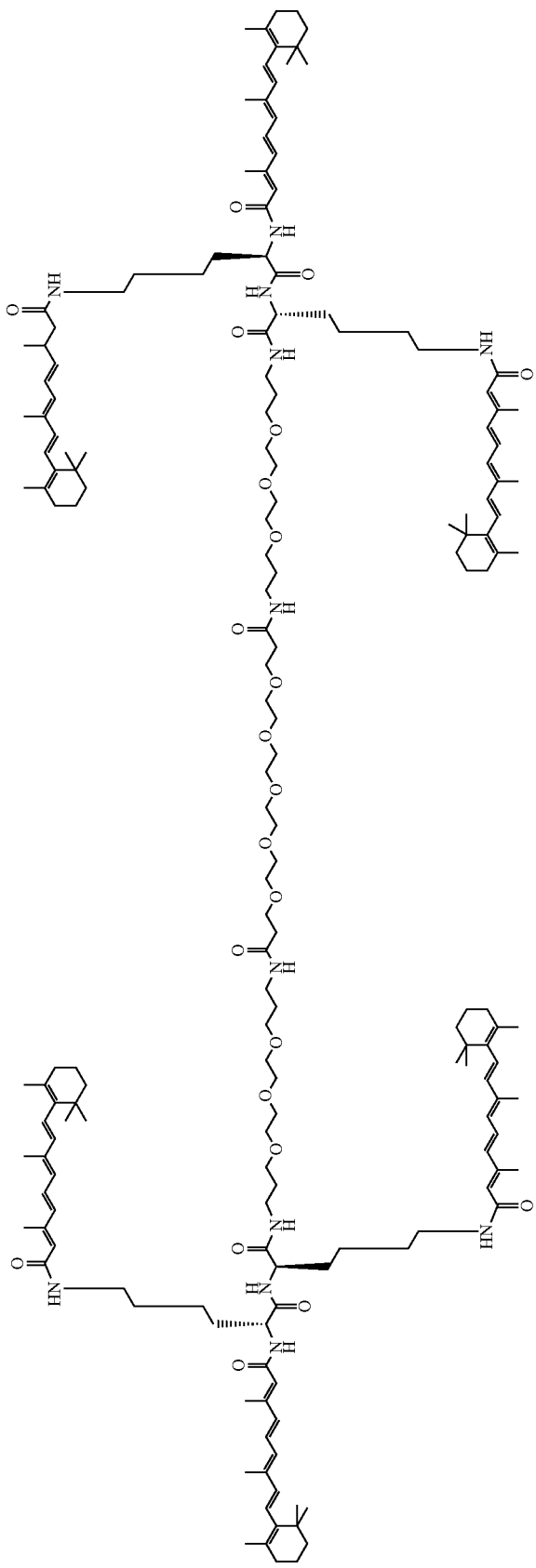

111

Preparation of Intermediate 1: (S)-methyl 6-(((benzyloxy)carbonyl)amino)-2-((S)-2,6-bis(((benzyloxy)carbonyl)amino)hexanamido) hexanoate

112

Preparation of Intermediate 2: (S)-6-(((benzyloxy)carbonyl)amino)-2-((S)-2,6-bis(((benzyloxy)carbonyl)amino)hexanamido)hexanoic acid

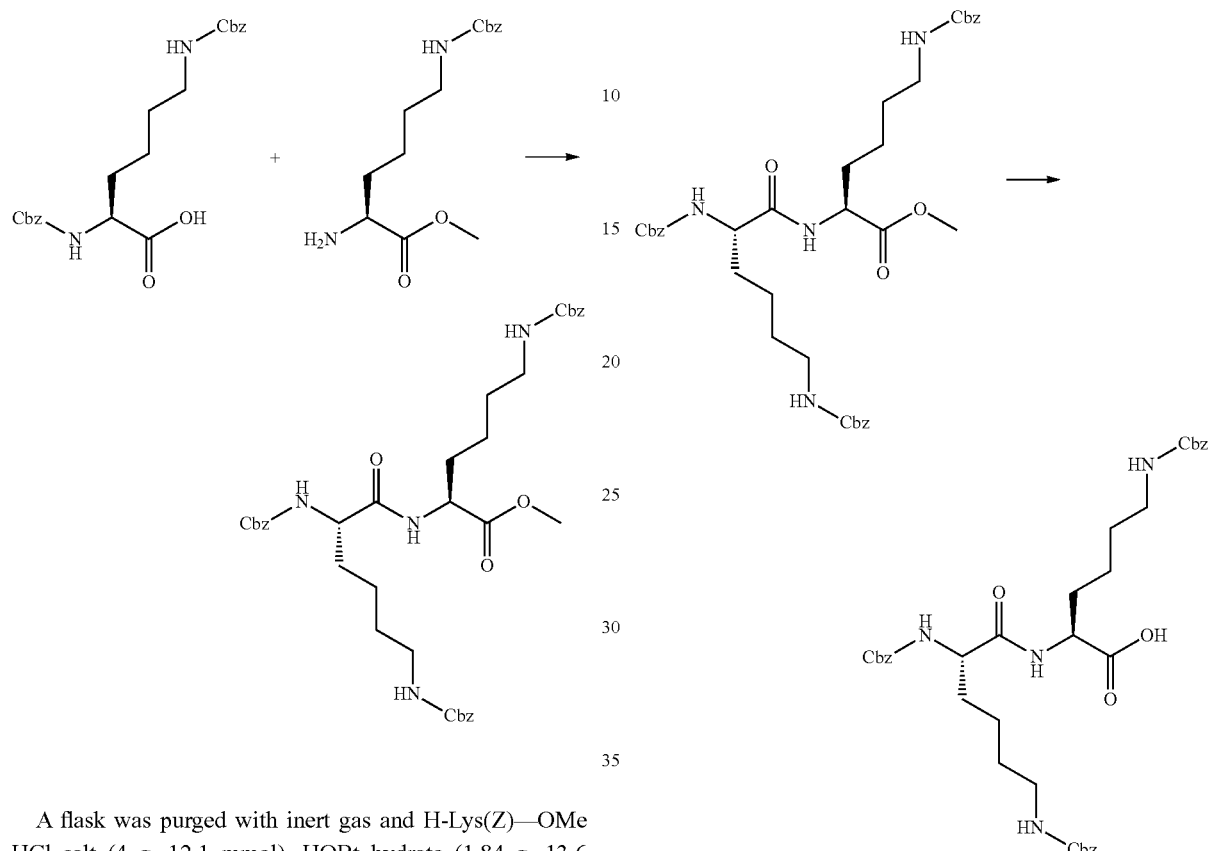

A flask was purged with inert gas and H-Lys(Z)—OMe HCl salt (4 g, 12.1 mmol), HOBt hydrate (1.84 g, 13.6 mmol), Z-Lys(Z)—OH (5.64 g, 13.6 mmol) are suspended in dichloromethane (50 mL). NMM (1.5 mL, 13.6 mmol) was added to the suspension and the solution became clear. A suspension EDC HCl salt (4.01 g, 20.9 mmol) and NMM (2.0 mL, 18.2 mmol) in dichloromethane (50 mL) was added over a period of 10 minutes. The reaction was stirred for 12 hours at room temperature, then washed with 1M HCl (100 mL), H₂O (100 mL), saturated bicarbonate solution (100 mL) and saturated brine solution (100 mL). All aqueous washes were back extracted with dichloromethane (50 mL). Dried organics with Na₂SO₄, filtered and concentrated. Material was purified by silica gel chromatography with a dichloromethane/methanol gradient to yield (S)-methyl 6-(((benzyloxy)carbonyl)amino)-2-((S)-2,6-bis(((benzyloxy)carbonyl)amino)hexanamido) hexanoate (6.91 g).

6-(((benzyloxy)carbonyl)amino)-2-((S)-2,6-bis(((benzyloxy)carbonyl)amino)hexanamido) hexanoate (6.91 g, 10 mmol) was dissolved with methanol (50 mL). Added KOH (2.24 g, 40 mmol) and stirred at 35° C. After 2 hours, quenched reaction by adding H₂O (200 mL) and washed mixture with diethyl ether (50 mL). Afterwards, adjusted the pH to ~2 with 1 M HCl acid. Extracted product with dichloromethane (3×100 mL), dried with Na₂SO₄, filtered and concentrated to yield (S)-6-(((benzyloxy)carbonyl)amino)-2-((S)-2,6-bis(((benzyloxy)carbonyl)amino)hexanamido)hexanoic acid (4 g).

Preparation of Intermediate 3: (Cbz)₆-protected N1,N19-bis((16S,19S)-19,23-diamino-16-(4-aminobutyl)-15,18-dioxo-4,7,10-trioxa-14,17-diazatricosyl)-4,7,10,13,16-pentaoxanonadecane-1,19-diamide

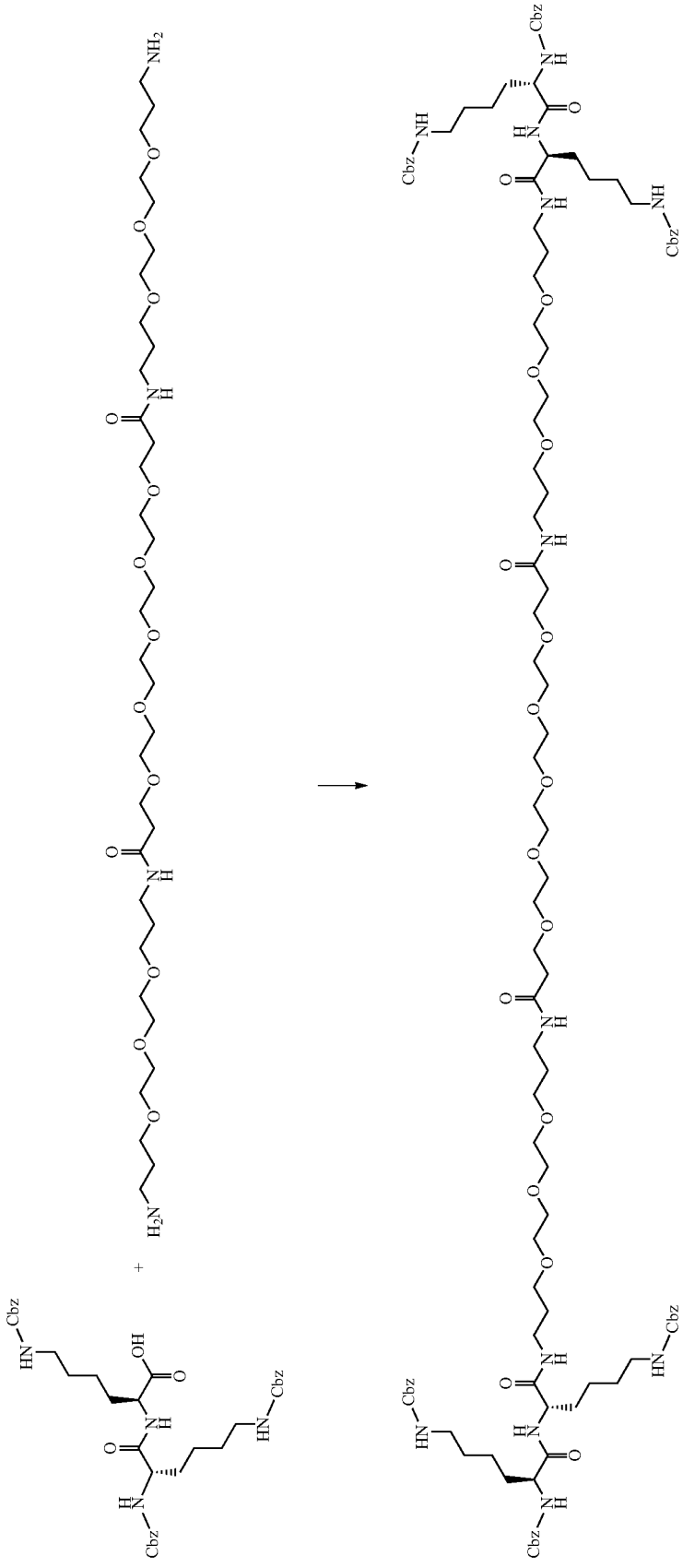

A flask was purged with inert gas and diamido-dPEG$_{11}$-diamine (1 g, 1.35 mmol), (S)-6-(((benzyloxy)carbonyl)amino)-2-((S)-2,6-bis(((benzyloxy)carbonyl)amino)hexanamido)hexanoic acid (2.05 g, 3.03 mmol), HOBt hydrate (409 mg, 3.03 mmol) are suspended in dichloromethane (25 mL). NMM (333 uL, 3.03 mmol) was added to the suspension and the solution became clear. A suspension EDC HCl salt (893 mg, 4.66 mmol) and NMM (445 μL, 4.05 mmol) in dichloromethane (25 mL) was added over a period of 10 minutes. The reaction was stirred for 12 hours at room temperature, then washed with 1M HCl (100 mL), water (100 mL), saturated bicarbonate solution (100 mL) and saturated brine solution (100 mL). All aqueous washes were back extracted with dichloromethane (50 mL). Dried organics with Na$_2$SO$_4$, filtered and concentrated. Material was purified by silica gel chromatography with a dichloromethane/methanol gradient to yield (Cbz)$_6$-protected N1,N19-bis((16S,19S)-19,23-diamino-16-(4-aminobutyl)-15,18-dioxo-4,7,10-trioxa-14,17-diazatricosyl)-4,7,10,13,16-pentaoxanonadecane-1,19-diamide (480 mg).

Preparation of Intermediate 4: N1,N19-bis((16S,19S)-19,23-diamino-16-(4-aminobutyl)-15,18-dioxo-4,7,10-trioxa-14,17-diazatricosyl)-4,7,10,13,16-pentaoxanonadecane-1,19-diamide

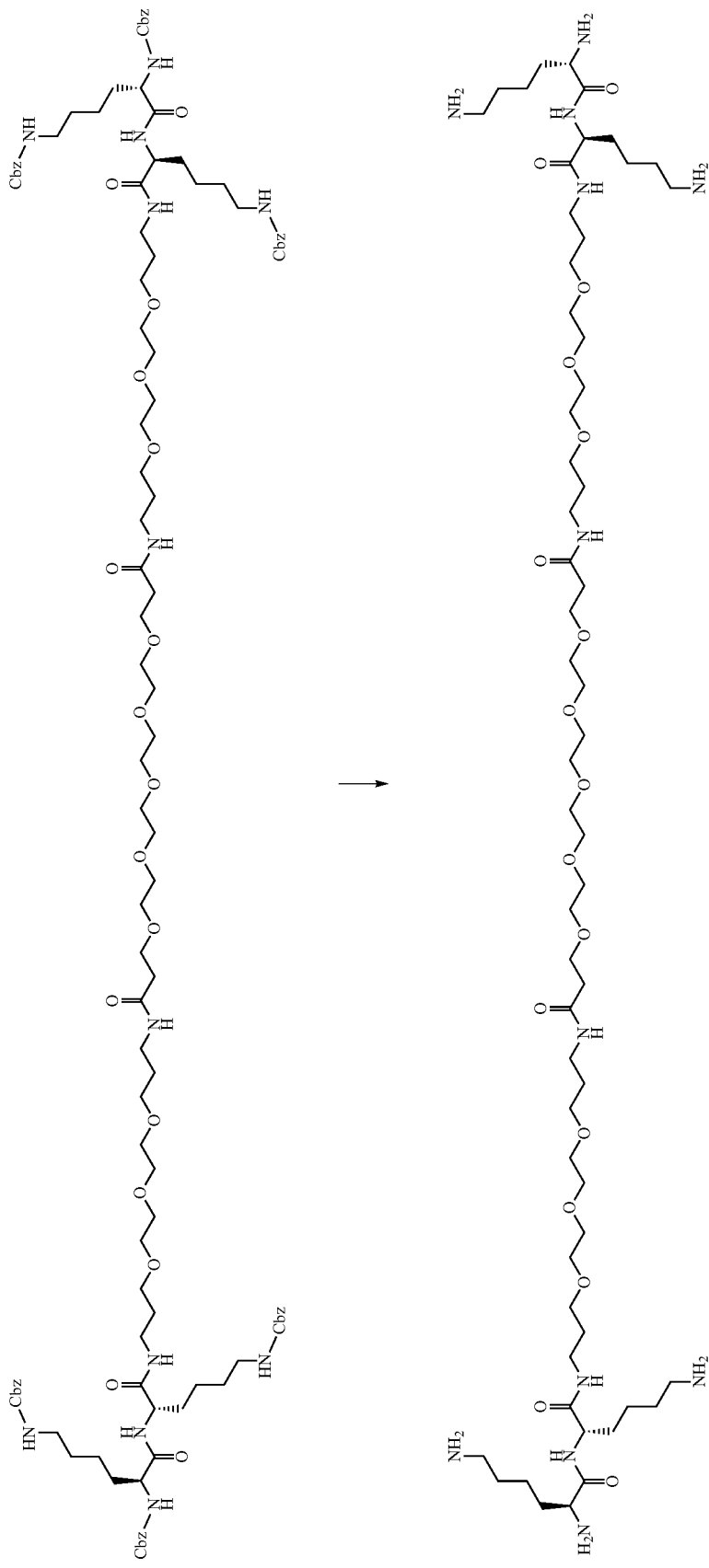

(Cbz)$_6$-protected N1,N19-bis((16S,19S)-19,23-diamino-16-(4-aminobutyl)-15,18-dioxo-4,7,10-trioxa-14,17-diazatricosyl)-4,7,10,13,16-pentaoxanonadecane-1,19-diamide was dissolved in methanol (30 mL) in a flask and flushed with an inert gas. 10% Pd/C (135 mg) was added and the flask was once again flushed with inert gas and then all air was removed via vacuum pump. An 8 inch H$_2$ balloon was added and the reaction was allowed to stir at room temperature. After 2 hours, the Pd/C was removed by filtering through a pad of CELITE® washing with methanol, and concentrated to yield N1,N19-bis((16S,19S)-19,23-diamino-16-(4-aminobutyl)-15,18-dioxo-4,7,10-trioxa-14,17-diazatricosyl)-4,7,10,13,16-pentaoxanonadecane-1,19-diamide (823 mg).

Preparation of TriVA

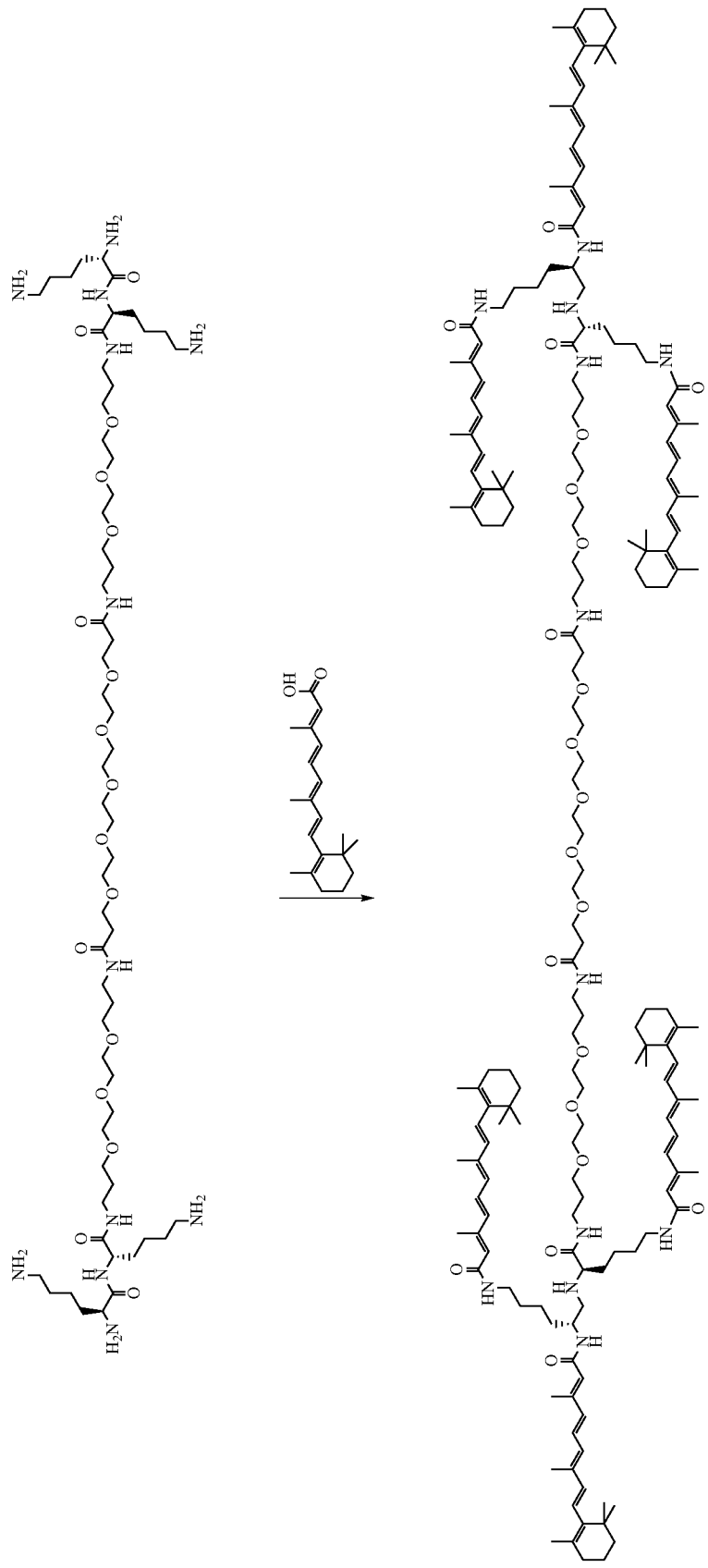

N1,N19-bis((16S,19S)-19,23-diamino-16-(4-aminobutyl)-15,18-dioxo-4,7,10-trioxa-14,17-diazatricosyl)-4,7,10,13,16-pentaoxanonadecane-1,19-diamide was stirred in dichloromethane and DMAP and retinoic acid was added. NMM was added and the solution was stirred in an aluminum foil covered flask flushed with inert gas at room temperature. A suspension of EDC HCl salt and NMM in dichloromethane (20 mL) was slowly added to reaction over a period of 10 minutes. Reaction was stirred for 12 hours at room temperature. Diluted with dichloromethane to 100 mL. Washed with $H_2O$ (100 mL), saturated bicarbonate solution (100 mL) and saturated brine solution (100 mL). All aqueous washes were back extracted with dichloromethane (50 mL). Dried organics with $Na_2SO_4$, filtered and concentrated. Material was purified by basic alumina chromatography eluting with dichloromethane/ethanol gradient to yield TriVA (780 mg). LCMS ESI+: m/z 2972 (M+Na).

Example 19 Synthesis of 4TTNPB

Preparation of 4TTNPB: N1,N19-bis((R)-1,8-dioxo-7-(4-((E)-2-(5,5,8,8-tetramethyl-5,6,7,8-tetrahydronaphthalen-2-yl)prop-1-en-1-yl)benzamido)-1-(4-((E)-2-(5,5,8,8-tetramethyl-5,6,7,8-tetrahydronaphthalen-2-yl)prop-1-en-1-yl)phenyl)-13,16,19-trioxa-2,9-diazadocosan-22-yl)-4,7,10,13,16-pentaoxanonadecane-1,19-diamide

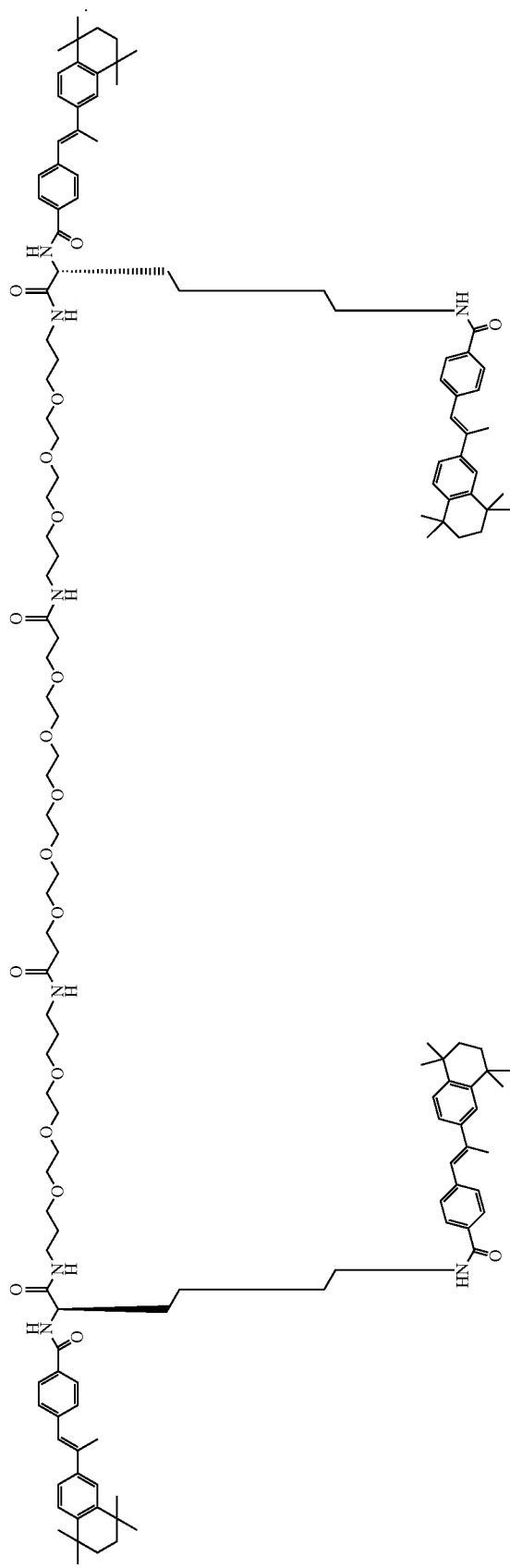

N1,N19-bis((R)-1,8-dioxo-7-(4-4E)-2-(5,5,8,8-tetramethyl-5,6,7,8-tetrahydro-naphthalen-2-yl)prop-1-en-1-yl)benzamido)-1-(4-((E)-2-(5,5,8,8-tetramethyl-5,6,7,8-tetrahydronaphthalen-2-yl)prop-1-en-1-yl)phenyl)-13,16,19-trioxa-2,9-diazadocosan-22-yl)-4,7,10,13,16-pentaoxanonadecane-1,19-diamide (4TTNPB), was prepared in similar fashion as N1,N19-bis((S,23E,25E,27E,29E)-16-((2E,4E,6E,8E)-3,7-dimethyl-9-(2,6,6-trimethyl-cyclo-hex-1-en-1-yl)nona-2,4,6,8-tetraenamido)-24,28-dimethyl-15,22-dioxo-30-(2,6,6-trimethylcyclohex-1-en-1-yl)-4,7,10-trioxa-14,21-diazatriaconta-23,25,27,29-tetraen-1-yl)-4,7,10,13,16-pentaoxanonadecane-1,19-diamide, referred to herein as diVA, from N1,N19-bis((S)-16,20-diamino-15-oxo-4,7,10-trioxa-14-azaicosyl)-4,7,10,13,16-pentaoxanonadecane-1,19-diamide with the substitution of TTNPB for all-trans retinoic acid. LCMS ESI+: m/z 2343 (M+Na).

Example 20 Synthesis of 4Myr

Preparation of 4Myr: N1,N19-bis((R)-15,22-dioxo-16-tetradecanamido-4,7,10-trioxa-14,21-diazapentatriacontyl)-4,7,10,13,16-pentaoxanonadecane-1,19-diamide

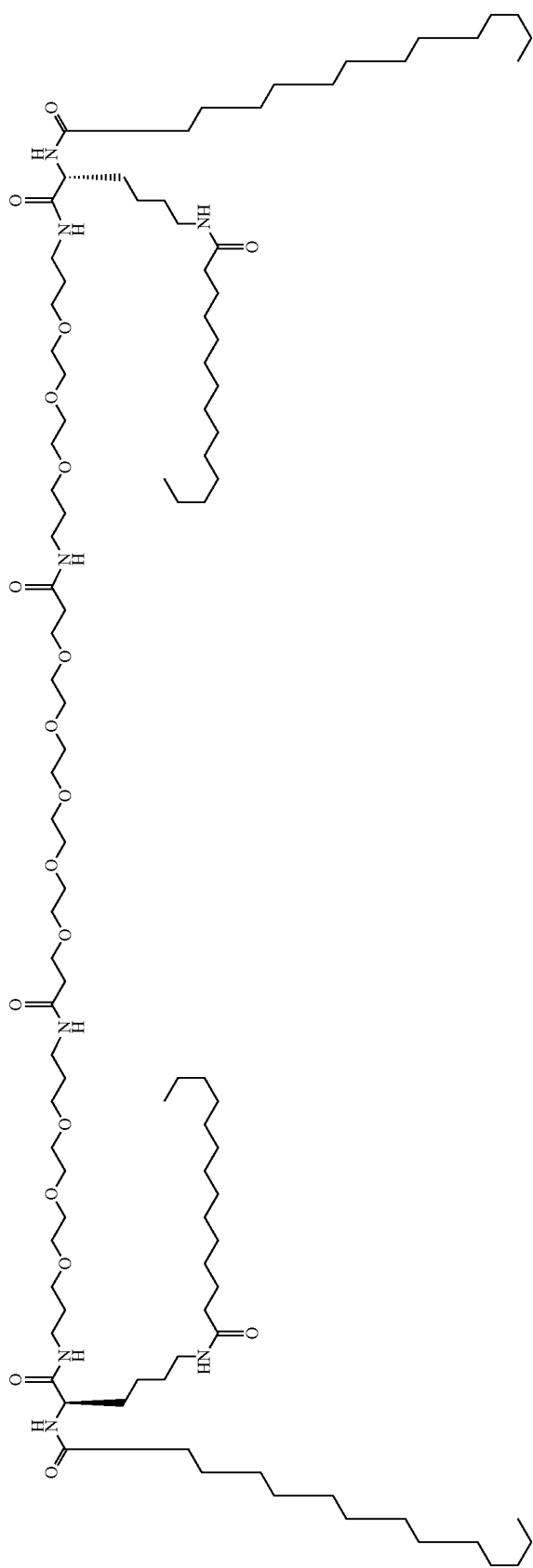

N1,N19-bis((R)-15,22-dioxo-16-tetradecanamido-4,7,10-trioxa-14,21-diaza-penta-triacontyl)-4,7,10,13,16-pentaoxanonadecane-1,19-diamide

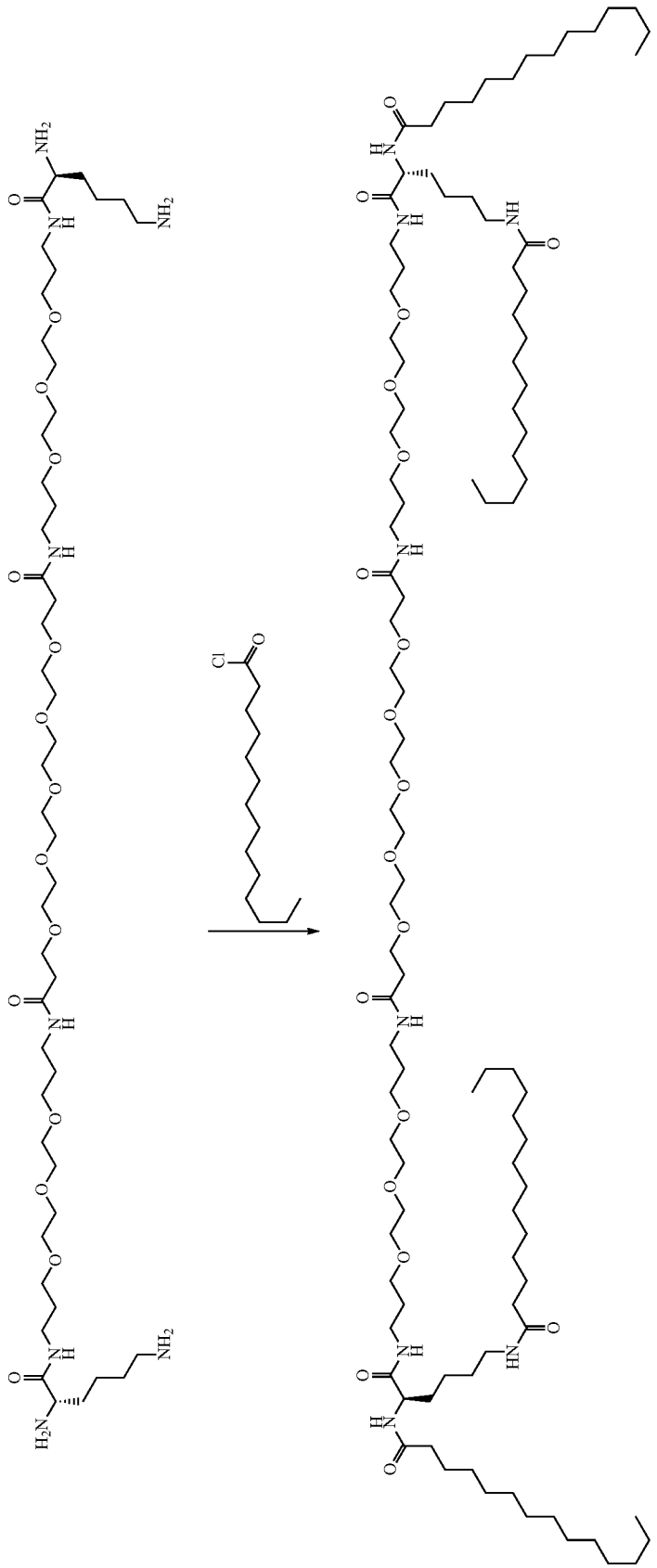

N1,N19-bis((S)-16,20-diamino-15-oxo-4,7,10-trioxa-14-azaicosyl)-4,7,10,13,16-pentaoxanonadecane-1,19-diamide (synthesis previously described) was dissolved in dichloromethane and placed in an ice-bath. Myristoyl chloride was added followed by triethylamine. The ice-bath was removed and the reaction was allowed to stir for 12 hours at room temperature under a blanket of inert gas. Diluted with dichloromethane to 100 mL and washed with 1M HCl (75 mL), water (75 mL), saturated bicarbonate solution (75 mL) and saturated brine solution (75 mL). Back extracted all aqueous washes with dichloromethane (25 mL). Dried organics with $MgSO_4$, filtered and concentrated. Purification by silica gel chromatography with a dichloromethane/methanol gradient yielded N1,N19-bis((R)-15,22-dioxo-16-tetradecanamido-4,7,10-trioxa-14,21-diaza-penta-triacontyl)-4,7,10,13,16-pentaoxanonadecane-1,19-diamide (410 mg). LCMS ESI+: m/z 1841 (M+H).

Example 21 Synthesis of DiVA-242

Preparation of DIVA-242: N1,N16-bis((R,18E,20E,22E,24E)-11-((2E,4E,6E,8E)-3,7-dimethyl-9-(2,6,6-trimethyl-cyclohex-1-en-1-yl)nona-2,4,6,8-tetraenamido)-19,23-dimethyl-10,17-dioxo-25-(2,6,6-trimethylcyclohex-1-en-1-yl)-3,6-dioxa-9,16-diazapentacosa-18,20,22,24-tetraen-1-yl)-4,7,10,13-tetraoxahexadecane-1,16-diamide

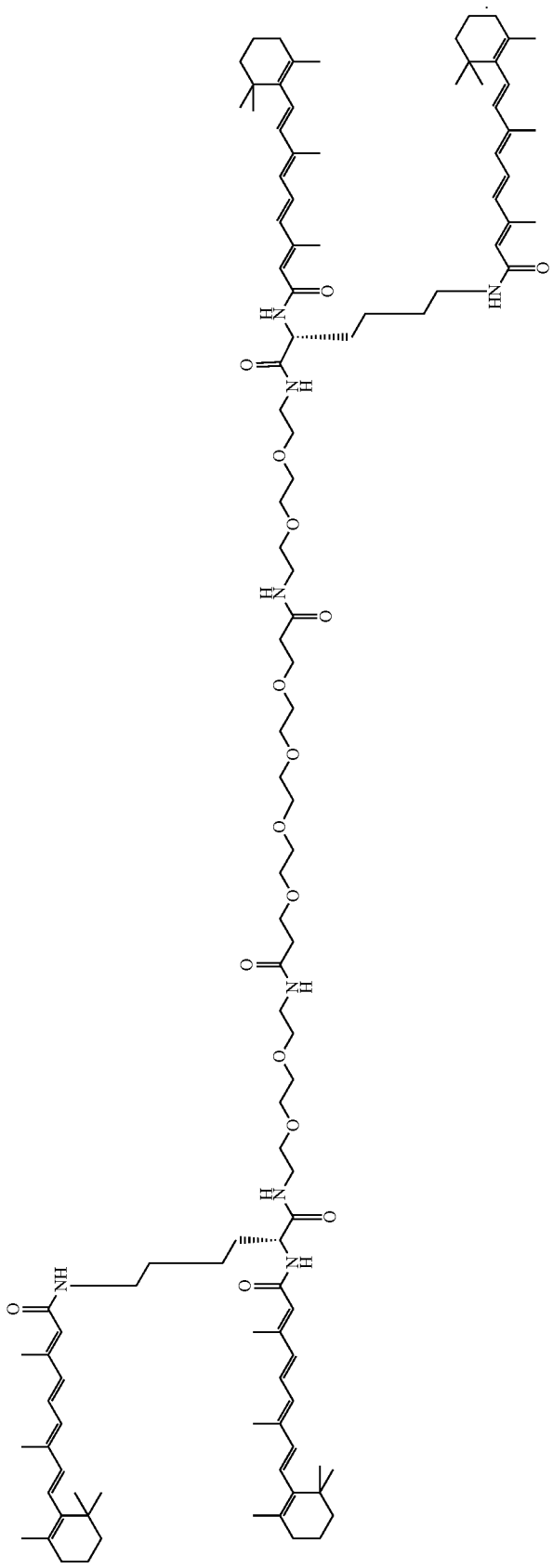

Preparation of Intermediate 1: di-tert-butyl (10,25-dioxo-3,6,13,16,19,22,29,32-octaoxa-9,26-diazatetratriacontane-1,34-diyl)dicarbamate

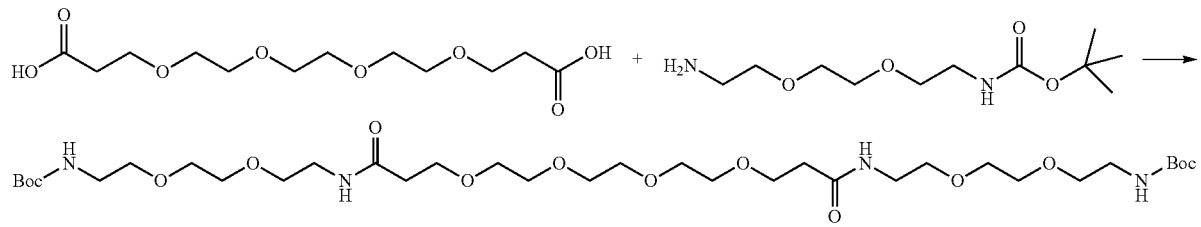

A flask containing dichloromethane (25 mL) was purged with inert gas and Bis-dPeg$_4$ acid (1000 mg, 3.40 mmol), N-Boc-3,6-dioxa-1,8-octane diamine (1816 μL, 7.65 mmol) and HOBt hydrate (1034 mg, 7.65 mmol) were added. NMM (841 μL, 7.65 mmol) was added to the suspension and the solution became clear. A suspension of EDC HCl salt (2249 mg, 11.7 mmol) and NMM (1121 uL, 10.2 mmol) in dichloromethane (25 mL) was added followed by DMAP (62 mg, 0.51 mmol). The reaction was stirred for 12 hours at room temperature. It was then diluted with dichloromethane to 100 mL and washed with H$_2$O (100 mL), 10% K$_2$CO$_3$ (100 mL) and saturated brine solution (100 mL), back extracted all aqueous washes with dichloromethane (30 mL), dried with MgSO$_4$, filtered and concentrated. Purification by silica gel chromatography with a dichloromethane/methanol gradient yielded di-tert-butyl (10,25-dioxo-3,6,13,16,19,22,29,32-octaoxa-9,26-diazatetratriacontane-1,34-diyl)dicarbamate (2.57 g).

Preparation of intermediate 2: N1,N16-bis(2-(2-(2-aminoethoxy)ethoxy)ethyl)-4,7,10,13-tetraoxahexadecane-1,16-diamide TFA salt

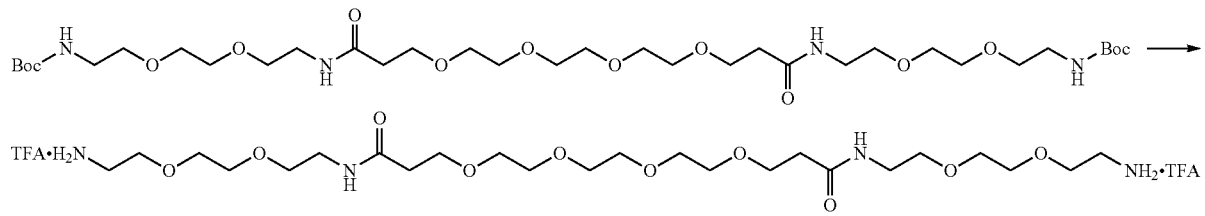

di-tert-butyl (10,25-dioxo-3,6,13,16,19,22,29,32-octaoxa-9,26-diazatetratriacontane-1,34-diyl) dicarbamate was dissolved in dichloromethane (15 mL) and placed into an ice bath, The round bottom flask was flushed with inert gas and TFA (15 mL) was added. Mixture was stirred for 20 minutes. Afterwards, the reaction mixture was concentrated to yield N1,N16-bis(2-(2-(2-aminoethoxy)ethoxy)ethyl)-4,7,10,13-tetraoxahexadecane-1,16-diamide TFA salt (1885 mg).

Preparation of DIVA-242: N1,N16-bis((R,18E,20E,22E,24E)-11-((2E,4E,6E,8E)-3,7-dimethyl-9-(2,6,6-trimethylcyclohex-1-en-1-yl)nona-2,4,6,8-tetraenamido)-19,23-dimethyl-10,17-dioxo-25-(2,6,6-trimethylcyclohex-1-en-1-yl)-3,6-dioxa-9,16-diazapentacosa-18,20,22,24-tetraen-1-yl)-4,7,10,13-tetraoxahexadecane-1,16-diamide

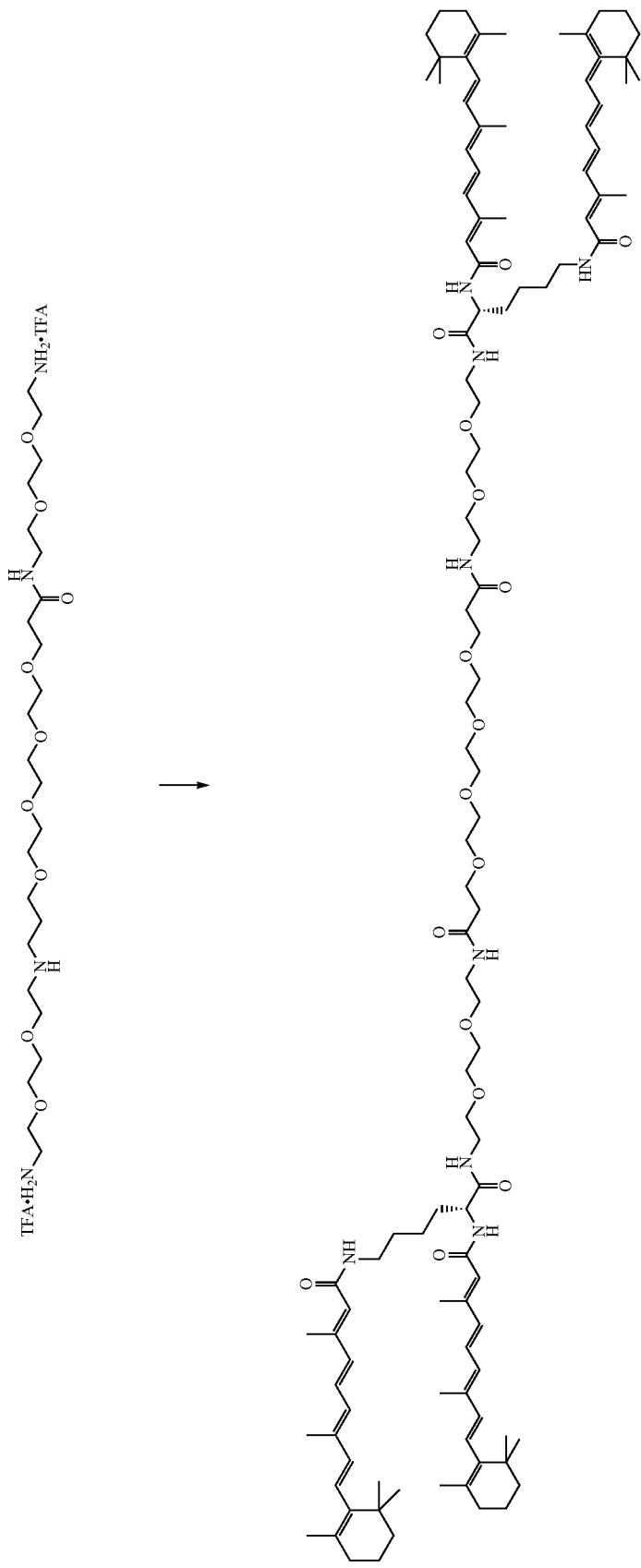

Synthesis of N1,N16-bis((R,18E,20E,22E,24E)-11-((2E,4E,6E,8E)-3,7-dimethyl-9-(2,6,6-trimethylcyclohex-1-en-1-yl)nona-2,4,6,8-tetraenamido)-19,23-dimethyl-10,17-dioxo-25-(2,6,6-trimethylcyclohex-1-en-1-yl)-3,6-dioxa-9,16-diazapentacosa-18,20,22,24-tetraen-1-yl)-4,7,10,13-tetraoxahexadecane-1,16-diamide (DIVA-242) follows the same protocol as diVA from N1,N16-bis(2-(2-(2-aminoethoxy)ethoxy)ethyl)-4,7,10,13-tetraoxahexadecane-1,16-diamide TFA salt. LCMS ESI+: m/z 1940 (M+H).

Example 22 In Vitro Efficacy of Fat-Soluble Vitamin Targeting Conjugate

Liposome formulations with 50 nM siRNA were tested. The liposomes were either: HEDC:S104:DOPE:Chol:PEG-DMPE:DiVA (+DiVA) or controls lacking vitamin A moieties (−DiVA) and were incubated in 96-well culture plates containing rat hepatic stellate cells for 30 minutes. After 30 minutes, medium was replaced with fresh growth medium. Forty eight hours later, cells were lysed and gp46 and GAPDH mRNA levels measured by quantitative RT-PCR (TAQMAN®) assay, and gp46 levels were normalized to GAPDH levels.

Figure 8:
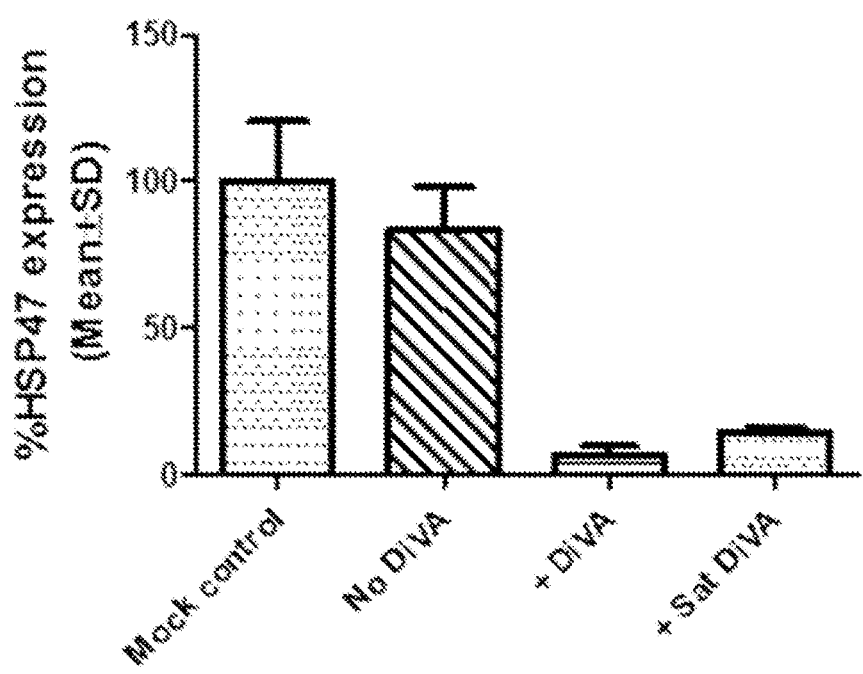
FIG. 8 shows in vitro efficacy in cell cultures (pHSC), and the effect of retinoid conjugates in liposome formulations.

As shown in FIG. 8, in vitro efficacy (pHSC), effect of 2% DiVA siRNA was efficacious with 2% diVA and had an $EC_{50}$ of 14 nM. This figure shows pHSCs in 96-well plate were incubated with formulation that lacked vitamin A moieties for targeting (−DiVA), or formulation that included vitamin A moieties (+DiVA) at 50 nM siRNA. After 30 minutes, medium was replaced with fresh growth medium. Forty eight hours later, cells were lysed and gp46 and GAPDH mRNA levels measured by quantitative RT-PCR (TAQMAN®) assay, and gp46 levels were normalized to GAPDH levels. Normalized gp46 levels were expressed as percent of mock control cells. Error bars indicate standard deviations (n=3). The mean gp46 level following DiVA containing treatment is significantly different from the mock control treatment (P<0.001) based on one-tailed t-test.

Comparison of DiVA and satDiVA

Liposome formulations were transfected into rat pHSCs for 30 min in 96-well plates. After 48 hours, the cells were processed using CELLS-TO-CT® lysis reagents (Applied Biosystems) and HSP47 mRNA levels were quantified by qRT-PCR. HSP47 expression was normalized mock control. $EC_{50}$ was determined by measuring HSP47 knockdown (KD) at six half-log doses of siRNA and fitting the data to the "Classic sigmoidal dose response function" in GRAPHPAD PRISM® 5.04.

Results shown that both DiVA and Sat DiVA increased KD efficacy (Table below, and FIG. 8). The $EC_{50}$ is 12 nM for DiVA and the $EC_{50}$ is 14 nM for SatDiVA.

| Compound (Type of Conjugate) | Formulation | in vitro (pHSC) $EC_{50}$ or % KD |
|---|---|---|
| DiVA (retinoid) | 20: 20 HEDC: S104 with 2% DiVA | 74% @ 50 nM |
| satDiVA (retinoid) | 20: 20 HEDC: S104 with 2% satDiVA | 73% @ 50 nM |
| 4TTNPB (non-retinoid) | 20: 20 HEDC: S104 with 2% 4TTNPB | 34% @ 50 nM |
| 4Myr (non-retinoid) | 20: 20 HEDC: S104 with 2% 4Myr | 27% @5 0 nM |

Example 23 In Vivo Efficacy of Fat-Soluble Vitamin Targeting Conjugate HEDC:S104:DOPE:Chol:PEG-DMPE:Diva In vivo activity of target formulation was evaluated in the short-term liver damage model (referred to as the Quick Model, DMNQ). In this model, short-term liver damage is induced by treatment with a hepatotoxic agent such as dimethylnitrosamine (DMN), and is accompanied by the elevation of gp46 mRNA levels. To induce these changes, male Sprague-Dawley rats were injected intraperitoneally with DMN on six consecutive days. At the end of the DMN treatment period, the animals were randomized to groups based upon individual animal body weight. Formulations were administered as a single IV dose, and given one hour after the last injection of DMN. Twenty four hours later, liver lobes were excised and both gp46 and MRPL19 mRNA levels were determined by quantitative RT-PCR (TAQMAN®) assay. mRNA levels for gp46 were normalized to MRPL19 levels.

Figure 9:
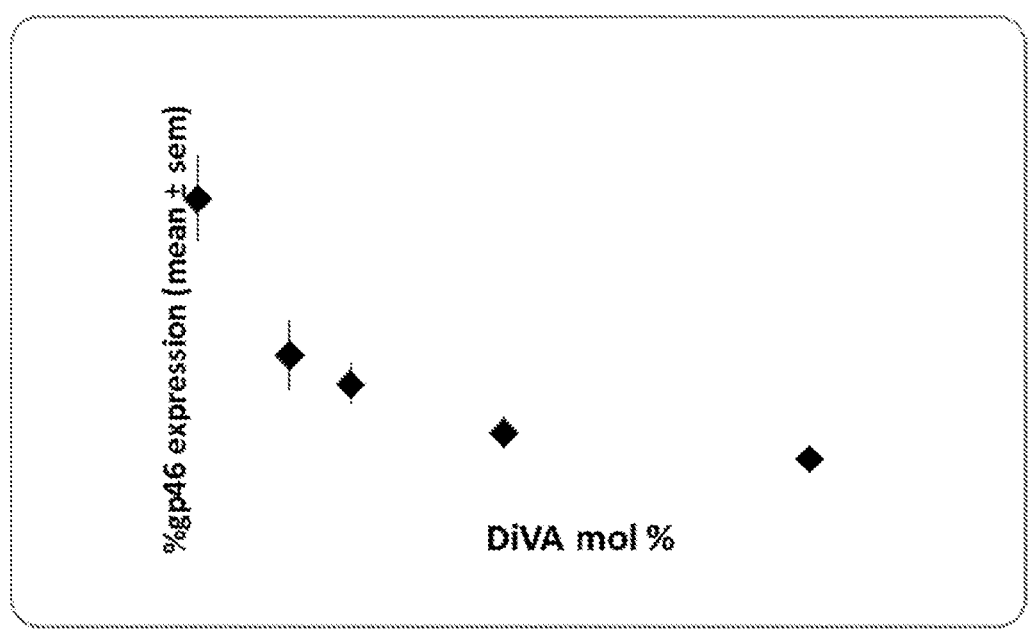
FIG. 9 correlates retinoid conjugate content (mol %) to in vivo (rat DMNQ) efficacy. Male Sprague-Dawley rats were injected intravenously either with formulations containing 0, 0.25, 0.5, 1, and 2% DiVA at a dose of 0.75 mg/kg siRNA, or PBS (vehicle), one hour after the last injection of dimethylnitrosamine (DMN).

The results (FIG. 9) show a correlation between the amount of retinoid conjugate and efficacy is evident. Only 0.25 mol % is required to see a significant effect in the rat DMNQ model. With 2 mol % DiVA a robust knockdown of gp46 expression is observed. FIG. 9 shows male Sprague-Dawley rats that were treated with DMN at 10 mg/kg on day 1, 2, 3 and 5 mg/kg on day 4, 5, 6 through intraperitoneal dosing to induce liver damage. Animals (n=eight/group) were injected intravenously either with formulations containing 0, 0.25, 0.5, 1, and 2% DiVA at a dose of 0.75 mg/kg siRNA, or PBS (vehicle), one hour after the last injection of DMN. Twenty four hours later, total siRNA was purified from a section of the right liver lobe from each animal and stored at 4° C. until RNA isolation. Control groups included a PBS vehicle group (DMN-treated) and naïve (untreated; no DMN) group. After subtracting background gp46 mRNA levels determined from the naïve group, all test group values were normalized to the average gp46 mRNA of the vehicle group (expressed as a percent of the vehicle group).

Male Sprague Dawley rats (130-160 g) were treated DMN through intraperitoneal dosing to induce liver fibrosis. The DMN treatment regimen was 3 times each week (Mon, Wed,

| Retinoid Conjugate | Formulation | in vitro (pHSC) $EC_{50}$ or % KD | in vivo (rat DMNQ) % KD |
|---|---|---|---|
| DIVA | 20: 20 HEDC: S104 with 2% DiVA | $EC_{50}$ = 12 nM | 60% @ 0.75 mpk |
| satDiVA | 20: 20 HEDC: S104 with 2% satDiVA | $EC_{50}$ = 14 nM | 74% @ 0.75 mpk |

Retinoid Conjugate Vs Non-Retinoid Conjugate

Retinoid conjugates were found to be consistently more potent in vitro relative to the non-retinoid equivalents (see 4TTNBB and 4MYR vs. the retinoid conjugate equivalents satDiVA and DiVA).

and Fri) with 10 mg/kg (i.e., 5.0 mg/mL of DMN at a dose of 2.0 mL/kg body weight) for first 3 weeks and half dose of 5 mg/kg (i.e., 5 mg/mL of DMN at a dose of 1.0 mL/kg) from day 22 to 57. The sham group animals were injected with PBS (solvent for DMN) using the same schedule. On Day 22, 24 h post the last DMN treatment, blood samples were collected and assayed for liver disease biomarkers to confirm the effectiveness of the DMN treatment. DMN treated animals were assigned to different treatment groups based on body weight and ensure that the mean body weights and the range of body weights of the animals in each group have no significant difference. Animals from pretreatment group were sacrificed on day 25 to evaluate the disease progression stage prior to treatment begins. Treatments with formulations containing gp46 siRNA were started at day 25 with two treatments/week at a specified siRNA dose for 10 times. On day 59, 48 hours after last formulation treatment and 72 hours after last DMN treatment, animals were sacrificed by $CO_2$ inhalation. Liver lobes were excised and both gp46 and MRPL19 mRNA levels were determined by quantitative RT-PCR (TAQMAN) assay. mRNA levels for gp46 were normalized to MRPL19 levels.

What is claimed:

1. A compound, consisting of the structure (lipid)$_m$-linker-(retinoid)$_n$ wherein m is 1, 2, or 3, and n is 1, 2, 3, 4 or 6; and wherein the linker comprises a polyethylene glycol (PEG), glutarate (Glu), hexyl, Gly$_3$, 4-aminobutanoate, or GluNH.

2. The compound of claim 1, wherein the lipid is selected from one or more of the group consisting of DODC, HEDODC, 1,2-distearoyl-sn-glycero-3-phosphoethanolamine (DSPE), 1,2-dioleoyl-sn-glycero-3-phosphoethanolamine (DOPE), and (6-(14-azanyl)hexanoyl)azanediyl) bis(ethane-2,1-diyl) ditetradecanoate (DC-6-14)

3. The compound of claim 2, wherein the retinoid is selected from the group consisting of vitamin A, retinoic acid, tretinoin, adapalene, 4-hydroxy(phenyl)retinamide, retinyl palmitate, retinal, saturated retinoic acid, and saturated, demethylated retinoic acid.

4. The compound of claim 2, wherein the linker comprises bis-amido-PEG, tris-amido-PEG, tetra-amido-PEG, Lys-bis-amido-PEG Lys, Lys-tris-amido-PEG-Lys, Lys-tetra-amido-PEG-Lys, Lys-PEG-Lys, PEG2000, PEG1250, PEG1000, PEG750, PEG550, Glu, PEG-Glu, hexyl, Gly$_3$, 4-aminobutanoate, or Glu-NH.

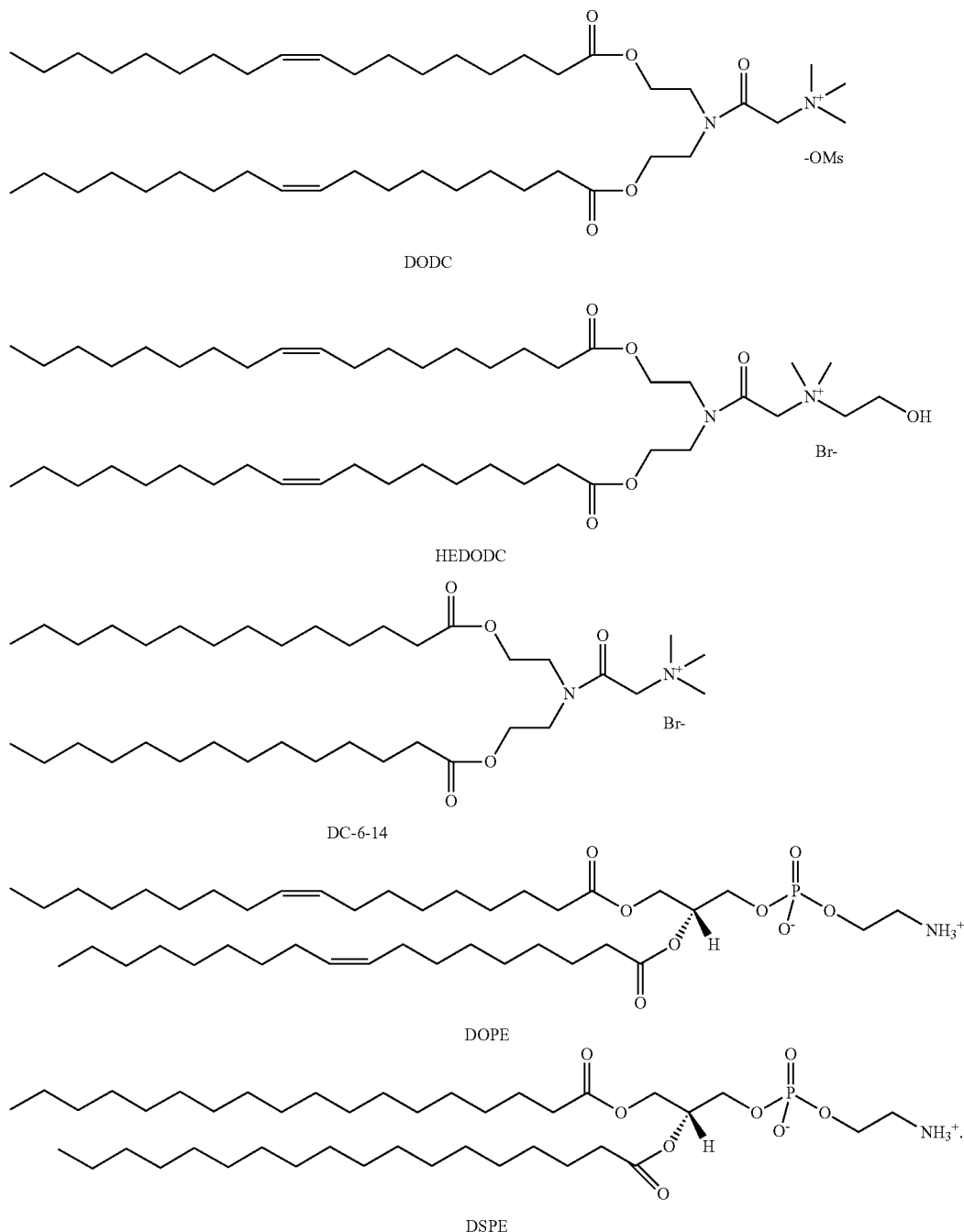

5. The compound of claim 4, selected from the group consisting of DSPE-PEG-VA, DSPE-PEG2000-Glu-VA, DSPE-PEG550-VA, DOPE-Glu-VA, DOPE-Glu-NH-VA, and DOPE-Gly$_3$-VA.

6. A composition comprising the compound of claim 1.

7. The composition of claim 6, further comprising additional lipid molecules.

8. The composition of claim 7, in the form of a liposomal composition.

9. The composition of claim 8, wherein the compound is at least partially exposed on the exterior of the liposomal composition.

10. The composition of claim 8, wherein the compound is 0.2 mol % to 20 mol % of the lipid molecules.

11. The composition of claim 7, wherein the lipid molecules comprise one or more lipids selected from the group consisting of HEDC, DODC, HEDC, HEDODC, 1,2-distearoyl-sn-glycero-3-phosphoethanolamine (DSPE), 1,2-dioleoyl-sn-glycero-3-phosphoethanolamine (DOPE), and (6-(14-azanyl)hexanoyl)azanediyl)bis(ethane-2,1-diyl) ditetradecanoate (DC-6-14)

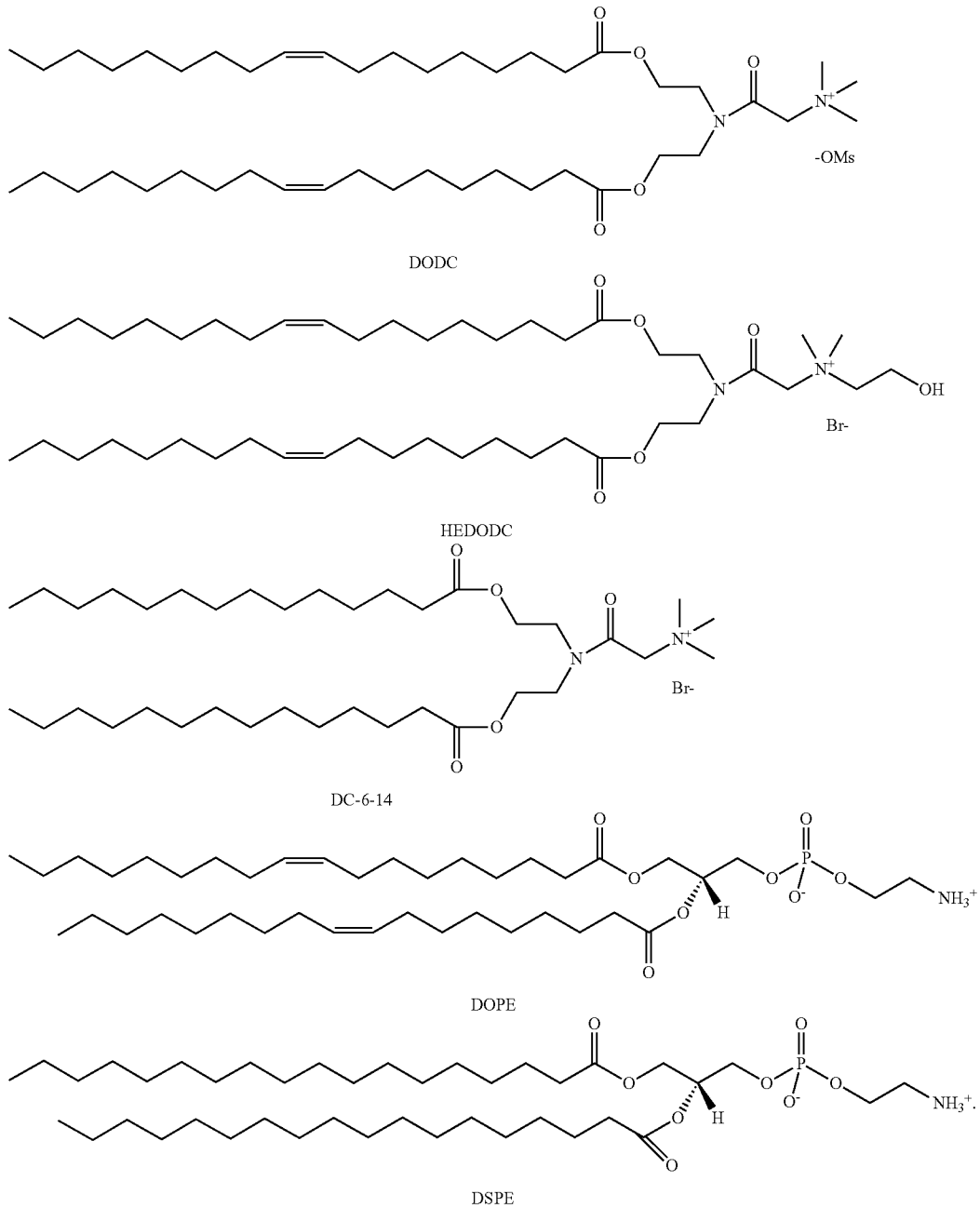

12. The composition of claim 11, wherein the lipid molecules further comprise S104

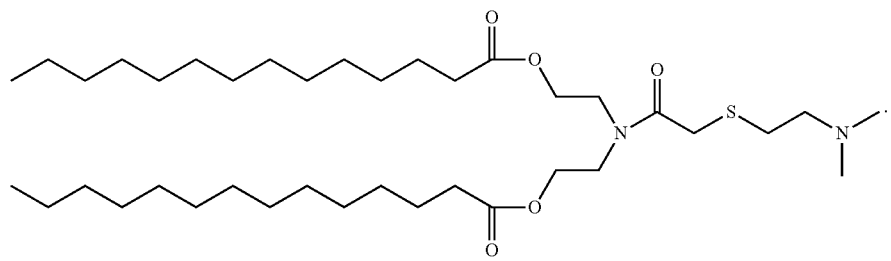

S104

13. The composition of claim 7, further comprising a nucleic acid.

14. The composition of claim 13, wherein the nucleic acid is an siRNA that is capable of knocking down expression of hsp47 mRNA in the stellate cell.

15. The composition of claim 6, wherein the linker comprises bis-amido-PEG, tris-amido-PEG, tetra-amido-PEG, Lys-bis-amido-PEG Lys, Lys-tris-amido-PEG-Lys, Lys-tetra-amido-PEG-Lys, Lys-PEG-Lys, PEG2000, PEG1250, PEG1000, PEG750, PEG550, Glu, PEG-Glu, hexyl, Gly$_3$ or 4-aminobutanoate.

16. The composition of claim 15, wherein the compound is selected from the group consisting of DSPE-PEG-VA, DSPE-PEG2000-Glu-VA, DSPE-PEG550-VA, DOPE-Glu-VA, DOPE-Glu-NH-VA, and DOPE-Gly$_3$-VA.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
ggacaggccu cuacaacuat t                                           21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
uaguuguaga ggccugucct t                                           21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
ggacaggccu guacaacuat t                                           21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
uaguuguaca ggccugucct t                                           21
```